(12) United States Patent
Kang et al.

(10) Patent No.: US 9,825,242 B2
(45) Date of Patent: Nov. 21, 2017

(54) COMPOUND FOR ORGANIC OPTOELECTRIC DEVICE, ORGANIC LIGHT-EMITTING DIODE INCLUDING SAME, DISPLAY DEVICE INCLUDING ORGANIC LIGHT-EMITTING DIODE

(71) Applicant: CHEIL INDUSTRIES INC., Gumi-si, Gyeongsangbuk-do (KR)

(72) Inventors: Dong-Min Kang, Suwon-si (KR); Hyun-Jung Kim, Suwon-si (KR); Chang-Ju Shin, Suwon-si (KR); Jong-Woo Won, Suwon-si (KR); Nam-Heon Lee, Suwon-si (KR); Soo-Young Jeong, Suwon-si (KR); Woo-Seok Jeong, Suwon-si (KR); Ho-Kuk Jung, Suwon-si (KR); Mi-Young Chae, Suwon-si (KR)

(73) Assignee: Cheil Industries, Inc., Gumi-si, Gyeongsangbuk-do (KR)

( * ) Notice: Subject to any disclaimer, the term of this patent is extended or adjusted under 35 U.S.C. 154(b) by 79 days.

(21) Appl. No.: 14/770,721

(22) PCT Filed: Aug. 12, 2013

(86) PCT No.: PCT/KR2013/007247
§ 371 (c)(1),
(2) Date: Aug. 26, 2015

(87) PCT Pub. No.: WO2014/185592
PCT Pub. Date: Nov. 20, 2014

(65) Prior Publication Data
US 2016/0056391 A1   Feb. 25, 2016

(30) Foreign Application Priority Data

May 13, 2013 (KR) .................. 10-2013-0054001

(51) Int. Cl.
*H01L 51/00* (2006.01)
*C07D 401/14* (2006.01)
(Continued)

(52) U.S. Cl.
CPC ........ *H01L 51/0072* (2013.01); *C07D 215/12* (2013.01); *C07D 401/10* (2013.01);
(Continued)

(58) Field of Classification Search
None
See application file for complete search history.

(56) References Cited

U.S. PATENT DOCUMENTS

2011/0272684 A1* 11/2011 Parham ................ C07D 209/94
257/40

FOREIGN PATENT DOCUMENTS

| CN | 102625806 A | 8/2012 |
| CN | 102703059 A | 10/2012 |

(Continued)

OTHER PUBLICATIONS

Chinese Search Report dated Jul. 15, 2016 in Corresponding Chinese Patent Application No. 201380076557.7.
(Continued)

*Primary Examiner* — J. L. Yang
(74) *Attorney, Agent, or Firm* — Lee & Morse, P.C.

(57) ABSTRACT

Provided are a compound for an organic optoelectric device represented by Chemical Formula 1, an organic light emitting diode including the same, and a display device including the organic light emitting diode. The structure of the compound for an organic optoelectric device represented by Chemical Formula 1 is described in the specification. The compound for an organic photoelectric device provides an organic light emitting diode having excellent electrochemical and thermal stability and improved life-span character-
(Continued)

istics, and high luminous efficiency at a low driving voltage, and the compound for an organic photoelectric device may be appropriate for a solution process.

12 Claims, 2 Drawing Sheets

(51) Int. Cl.
    *H01L 27/32*     (2006.01)
    *C07D 401/10*     (2006.01)
    *C09K 11/02*     (2006.01)
    *C09K 11/06*     (2006.01)
    *C07D 215/12*     (2006.01)
    *C07D 403/10*     (2006.01)
    *C07D 403/14*     (2006.01)
    *H01L 51/50*     (2006.01)

(52) U.S. Cl.
    CPC ......... *C07D 401/14* (2013.01); *C07D 403/10* (2013.01); *C07D 403/14* (2013.01); *C09K 11/025* (2013.01); *C09K 11/06* (2013.01); *H01L 27/3244* (2013.01); *H01L 51/0052* (2013.01); *H01L 51/0058* (2013.01); *H01L 51/0067* (2013.01); *H01L 51/0071* (2013.01); *C09K 2211/1007* (2013.01); *C09K 2211/1011* (2013.01); *C09K 2211/1029* (2013.01); *C09K 2211/1033* (2013.01); *C09K 2211/1044* (2013.01); *C09K 2211/1059* (2013.01); *H01L 51/5012* (2013.01); *H01L 51/5072* (2013.01); *H01L 51/5092* (2013.01)

(56) References Cited

FOREIGN PATENT DOCUMENTS

| | | |
|---|---|---|
| EP | 2 508 585 A1 | 10/2012 |
| JP | 2006-525357 A | 11/2006 |
| JP | 2007-015993 A | 1/2007 |
| JP | 2007-223928 A | 9/2007 |
| JP | 4048780 B2 | 2/2008 |
| JP | 2009-227663 A | 10/2009 |
| JP | 2010-275255 A | 12/2010 |
| JP | 2013-032343 A | 2/2013 |
| KR | 10-0933226 B1 | 12/2009 |
| KR | 10-2010-0001274 * | 1/2010 |
| KR | 10-2011-0005666 A | 1/2011 |
| KR | 10-2011-0013220 A | 2/2011 |
| KR | 10-2011-0076488 A | 7/2011 |
| KR | 10-2011-0096453 A | 8/2011 |
| KR | 10-1075215 B1 | 10/2011 |
| KR | 10-2012-0027600 A | 3/2012 |
| KR | 10-2012-0038060 A | 4/2012 |
| KR | 10-1531615 B1 | 6/2015 |
| WO | WO 01/42218 A1 | 6/2001 |
| WO | WO 2004 081009 A1 | 9/2004 |
| WO | WO 2004-099159 A1 | 11/2004 |
| WO | WO 2011/014039 A1 | 2/2011 |
| WO | WO 2012/024132 A2 | 2/2012 |
| WO | WO 2012/036482 A1 | 3/2012 |
| WO | WO 2012/050347 A1 | 4/2012 |
| WO | WO 2012/134124 A1 | 10/2012 |
| WO | WO 2013-003586 A1 | 1/2013 |
| WO | WO 2013/162148 A1 | 10/2013 |
| WO | WO 2016/104118 A1 | 6/2016 |

OTHER PUBLICATIONS

Extended European Search Report dated Nov. 4, 2016 in corresponding European Patent Application No. 13884807.2, Lee.
Chihaya Adachi, et al., "Electroluminescence in Organic Films with Three-Layer Structure", Japanese Journal of Applied Physics, vol. 27, No. 2, Feb. 1988, pp. L269-L271.
Sebastian Scholz, et al., "Photochemical reactions in organic semiconductor thin films", Organic Electronics, 8, 709 (2007).
Search Report dated Apr. 10, 2017, of the corresponding Chinese Patent Application No. 201380076557.7.

* cited by examiner

[Figure 1]
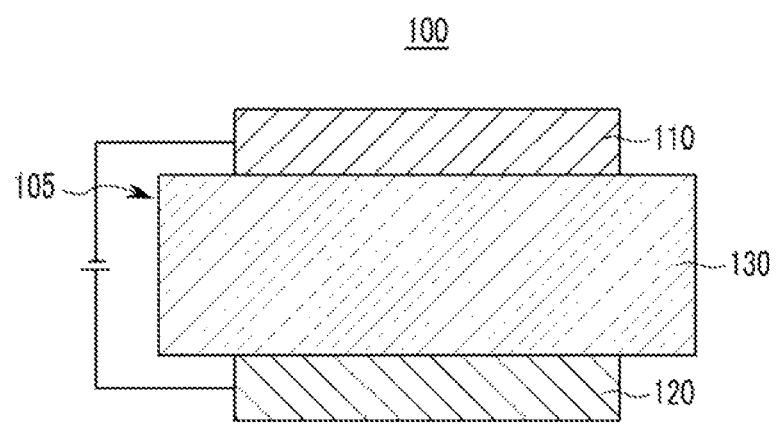

[Figure 2]
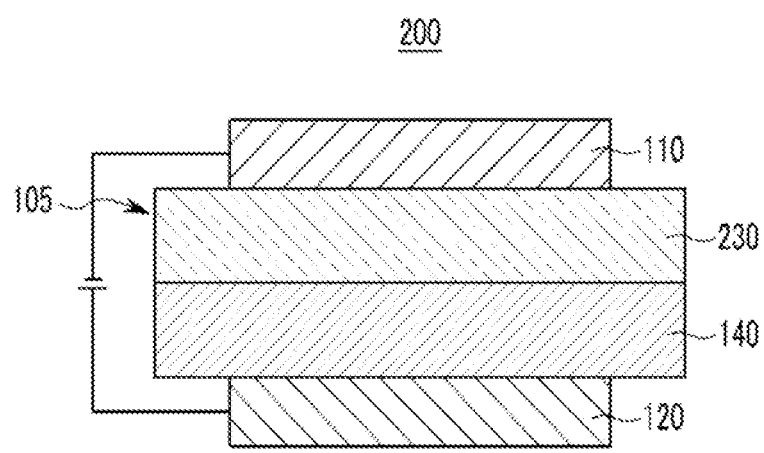

COMPOUND FOR ORGANIC OPTOELECTRIC DEVICE, ORGANIC LIGHT-EMITTING DIODE INCLUDING SAME, DISPLAY DEVICE INCLUDING ORGANIC LIGHT-EMITTING DIODE

CROSS REFERENCE TO RELATED APPLICATIONS

This is the U.S. national phase application based on PCT Application No. PCT/KR2013/007247, filed Aug. 12, 2013, which is based on Korean Patent Application No. 10-2013-0054001, filed May 13, 2013, the entire contents of all of which are hereby incorporated by reference.

TECHNICAL FIELD

A compound for an organic optoelectric device, an organic light emitting diode including the same, and a display device including the organic light emitting diode are disclosed.

BACKGROUND ART

An organic optoelectric device is a device requiring a charge exchange between an electrode and an organic material by using holes or electrons.

An organic optoelectric device may be classified as follows in accordance with its driving principles. A first organic optoelectric device is an electronic device driven as follows: excitons are generated in an organic material layer by photons from an external light source; the excitons are separated into electrons and holes; and the electrons and holes are transferred to different electrodes as a current source (voltage source).

A second organic optoelectric device is an electronic device driven as follows: a voltage or a current is applied to at least two electrodes to inject holes and/or electrons into an organic material semiconductor positioned at an interface of the electrodes, and the device is driven by the injected electrons and holes.

Examples of the organic optoelectric device includes organic photoelectric device, an organic light emitting diode, an organic solar cell, an organic photo conductor drum, and an organic transistor, and the like, which requires a hole injecting or transport material, an electron injecting or transport material, or a light emitting material.

Particularly, an organic light emitting diode (OLED) has recently drawn attention due to an increasing demand for a flat panel display. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer includes a multi-layer including different materials, for example a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material can be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect, and therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectric devices.

The low molecular organic light emitting diode is manufactured as a thin film in a vacuum deposition method and can have good efficiency and life-span performance. A polymer organic light emitting diode is manufactured in an Inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristic compared with a conventional LCD (liquid crystal display) and have an advantage of decreasing thickness and weight of LCD up to a third, because they do not need a backlight.

In addition, since they have a response speed of a microsecond unit, which is 1000 time faster than LCD, they can realize a perfect motion picture without after-image. Based on these advantages, they have been remarkably developed to have 80 times efficiency and more than 100 times life-span since they come out for the first time in the late 1980s and recently, they keep being rapidly larger such as a 40-inch organic light emitting diode panel.

They are simultaneously required to have improved luminous efficiency and life-span in order to be larger. Therefore, a stable and efficient organic material layer material for an organic light emitting diode needs to be developed.

DISCLOSURE

Technical Problem

One embodiment provides a compound being capable of providing an organic optoelectric device having high efficiency and long life-span.

Another embodiment provides an organic light emitting diode including the compound and a display device including the organic light emitting diode.

Technical Solution

In one embodiment of the present invention, a compound represented by Chemical Formula 1 for an organic optoelectric device is provided.

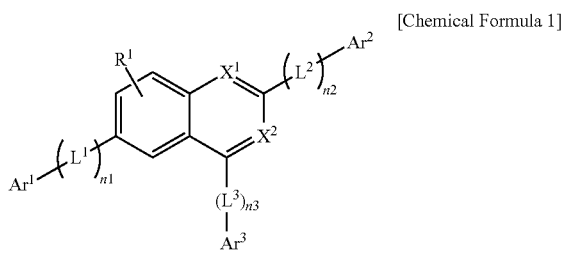

[Chemical Formula 1]

In Chemical Formula 1, $X^1$ and $X^2$ are each independently N or CR', at least one of $X^1$ and $X^2$ is N, $Ar^3$ is a substituted or unsubstituted C2 to C30 heteroaryl group, $Ar^1$ and $Ar^2$ are each independently a substituted or unsubstituted C6 to C30 aryl group, or a substituted or unsubstituted C2 to C30 heteroaryl group, $L^1$ to $L^3$ are each independently a substituted or unsubstituted C6 to C30 arylene group or a substituted or unsubstituted C2 to C30 heteroarylene group, n1 to n3 are 0 or 1, $R^1$ and R' are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group or a substituted or unsubstituted silyl group.

In another embodiment of the present invention, provided is an organic light emitting diode that includes an anode, a cathode and at least one organic thin layer between the anode and the cathode, wherein at least one layer of the organic thin layer includes the compound according to the embodiment of the present invention.

In yet another embodiment of the present invention, a display device including the organic light emitting diode according to the embodiment of the present invention is provided.

Advantageous Effects

An organic optoelectric device including the compound according to the embodiment of the present invention has excellent electrochemical and thermal stability, improved life-span characteristics, and high luminous efficiency at a low driving voltage. In addition, the compound may be appropriate for a solution process.

DESCRIPTION OF THE DRAWINGS

FIGS. 1 and 2 are cross-sectional views showing various embodiments of organic light emitting diodes according to embodiments of the present invention.

<Description of Reference Numerals Indicating Primary Elements in the Drawings>

| | |
|---|---|
| 100, 200: organic light emitting diode | 105: organic layer |
| 110: cathode | 120: anode |
| 130, 230: emission layer | 140: hole auxiliary layer |

[Mode For Invention]

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a substituent selected from deuterium deuterium, a halogen, hydroxy group, an amino group, a substituted or unsubstituted C1 to C30 amine group, a nitro group, a substituted or unsubstituted C1 to C40 silyl group, C1 to C30 alkyl group, C1 to C10 alkylsilyl group, C3 to C30 cycloalkyl group, C6 to C30 aryl group, C1 to C20 alkoxy group, a fluoro group, a C1 to C10 trifluoroalkyl group such as a trifluoromethyl group or cyano group instead of at least one hydrogen of a functional group.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused with each other to form a ring.

In the present specification, when specific definition is not otherwise provided, the term "hetero" refers to one including 1 to 3 hetero atoms selected from N, O, S, and P, and remaining carbons in one compound or substituent.

In the present specification, when a definition is not otherwise provided, the term "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C20 alkyl group. More specifically, the alkyl group may be a C1 to C10 alkyl group or a C1 to C6 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a cyclic substituent where all elements have p-orbitals, and these p-orbitals forms conjugation, and includes a monocyclic or fused ring polycyclic (i.e., rings sharing adjacent pairs of carbon atoms) functional group.

In the present specification, "heteroaryl group" refers to aryl group including 1 to 3 hetero atoms selected from N, O, S, and P, and remaining carbons. When the heteroaryl group is a fused ring, each ring may include 1 to 3 hetero atoms.

More specifically, the substituted or unsubstituted C6 to C30 aryl group and/or the substituted or unsubstituted C2 to C30 heteroaryl group refer to a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted fluorenyl group, a substituted or unsubstituted dibenzofuranyl group, a substituted or unsubstituted dibenzothiophenyl group, a substituted or unsubstituted carbazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but are not limited thereto.

In the present specification, hole characteristics refer to characteristics that holes formed in the anode is easily injected into the emission layer and transported in the emission layer due to conductive characteristics according to HOMO level. More specifically, it is similar to electron-repelling characteristics.

Electron characteristics refer to characteristics that electron formed in the cathode is easily injected into the emission layer and transported in the emission layer due to conductive characteristics according to LUMO level. More specifically, it is similar to electron-withdrawing characteristics.

In one embodiment of the present invention, a compound represented by Chemical Formula 1 for an organic optoelectric device is provided.

[Chemical Formula 1]

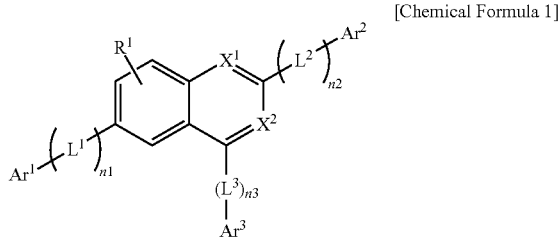

In Chemical Formula 1, $X^1$ and $X^2$ are each independently N or CR', at least one of $X^1$ and $X^2$ is N, $Ar^3$ is a substituted or unsubstituted C2 to C30 heteroaryl group, $Ar^1$ and $Ar^2$ are each independently a substituted or unsubstituted C6 to C30 aryl group, or a substituted or unsubstituted C2 to C30 heteroaryl group, $L^1$ to $L^3$ are each independently a substituted or unsubstituted C6 to C30 arylene group or a substituted or unsubstituted C2 to C30 heteroarylene group, n1 to n3 are independently 0 or 1, and $R^1$ and R' are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group.

The compound according to one embodiment of the present invention includes a substituted or unsubstituted C2 to C30 heteroaryl group at the $Ar^3$, which gives a steric effect and may improve amorphous properties. In addition, charge transport characteristics of the compound may be improved.

In addition, the compound represented by Chemical Formula 1 may have various energy bandgaps due to various substituents.

The compound may have an appropriate energy level depending on the substituents and thus, may fortify hole transport capability or electron transport capability of an organic optoelectric device and bring about excellent effects on efficiency and driving voltage and also, have excellent electrochemical and thermal stability and thus, improve life-span characteristics during the operation of the organic optoelectric device.

More specifically, the $Ar^3$ may be a substituent represented by Chemical Formula 2 or A.

[Chemical Formula 2]

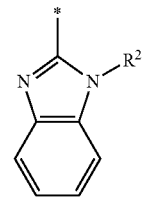

[Chemical Formula A]

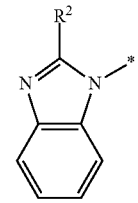

In Chemical Formulae 2 and A, $R^2$ is hydrogen, deuterium, a substituted to or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group or a substituted or unsubstituted silyl group.

The substituent such as Chemical Formula 2 has a high glass transition temperature such as a high thermal decomposition temperature and thus improves life-span characteristics.

Or, the $Ar^3$ may be a substituted or unsubstituted pyridinyl group, a substituted or unsubstituted pyrimidinyl group, a substituted or unsubstituted triazinyl group, a substituted or unsubstituted quinolinyl group, or a substituted or unsubstituted isoquinolinyl group. In this case, charge injection and charge mobility may be improved.

In one embodiment of the present invention, the $Ar^1$ and $Ar^2$ may be each independently a substituted or unsubstituted C6 to C30 aryl group. More specifically, the $Ar^1$ and $Ar^2$ may be a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group. In this case, hole and/or electron characteristics of the compound may be appropriately adjusted.

In one embodiment of the present invention, at least one of the $Ar^1$ and $Ar^2$ may be a substituted or unsubstituted carbazolyl group. In this case, charge mobility may be improved due to appropriate molecular energy and triplet energy, and the compound may have characteristics appropriate for an emission layer due to characteristics of the carbazolyl group.

For more specific examples, at least one of the $Ar^1$ and $Ar^2$ may be a substituent represented by Chemical Formula 3 or 4.

[Chemical Formula 3]

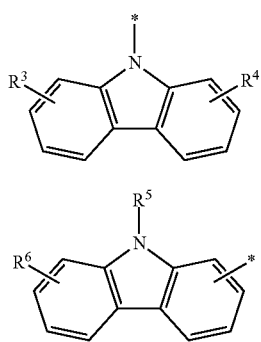

[Chemical Formula 4]

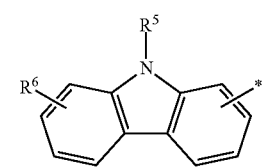

In Chemical Formulae 3 and 4, $R^3$ to $R^6$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group or a substituted or unsubstituted silyl group.

In one embodiment of the present invention, the $L^3$ may be a substituted or unsubstituted C2 to C30 heteroarylene group. In this case, electron characteristics of the compound may be fortified, and thus charge mobility increases and high efficiency may be provided.

For more specific examples, the $L^3$ may be a substituted or unsubstituted pyridinylene group, a substituted or unsubstituted pyrimidinylene group or a substituted or unsubstituted triazinylene group. But it is not limited thereto.

The $L^1$ to $L^3$ may be selectively adjusted to determine an entire conjugation length of the compound, and a triplet energy bandgap of the compound may be adjusted therefrom. Thereby, characteristics of a material required of an organic optoelectric device may be realized. In addition, the triplet energy bandgap may also be adjusted by changing a bonding position of ortho, para, and meta.

Simultaneously, the $L^1$ and $L^2$ may be a substituted or unsubstituted C6 to C30 arylene group, and in this case, the compound may have appropriate hole and electron characteristics.

Specific examples of the $L^1$ and $L^2$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted p-terphenyl group, a substituted or unsubstituted m-terphenyl group, a substituted or unsubstituted perylenyl group, and the like.

In one embodiment of the present invention, the $X^1$ may be N, and the $X^2$ may be CR'. But they are not limited thereto.

Specific examples of the compound according to one embodiment of the present invention are as follows, but are not limited thereto.

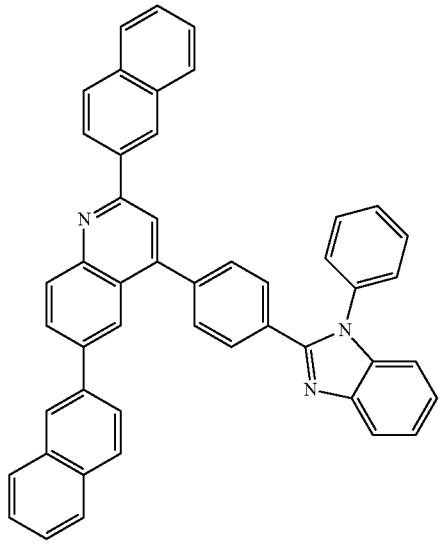

[A-1]

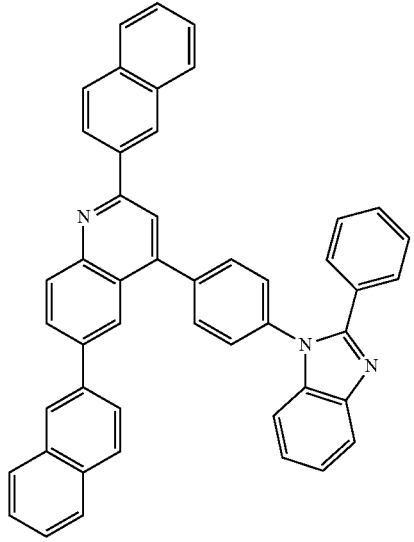

[A-2]

-continued
[A-3]
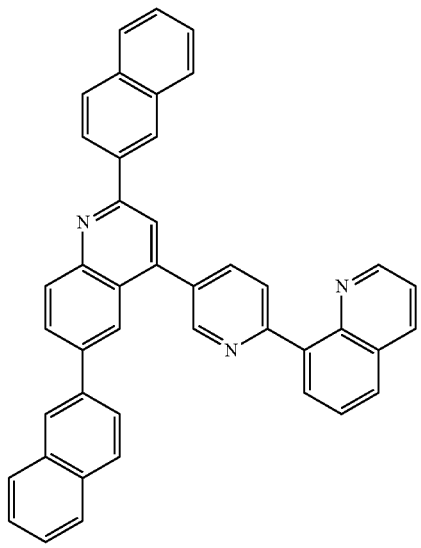
[A-4]
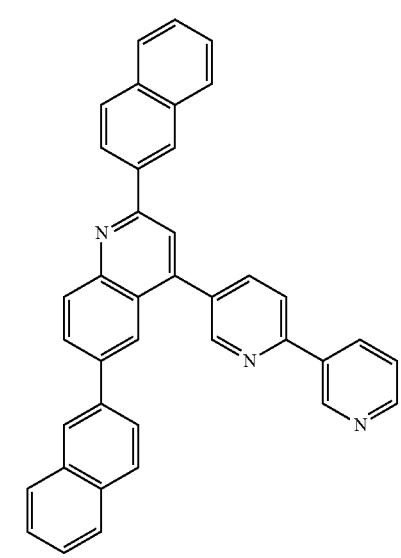
[A-5]
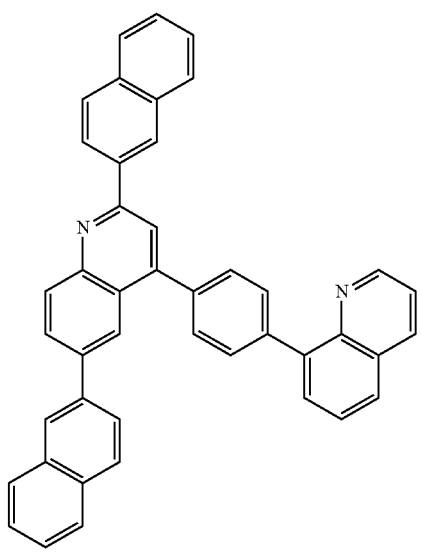
-continued
[A-6]
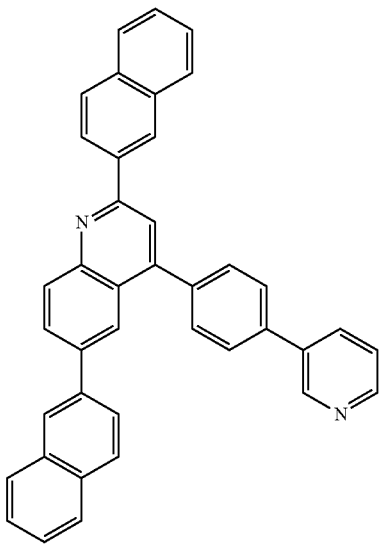
[A-7]
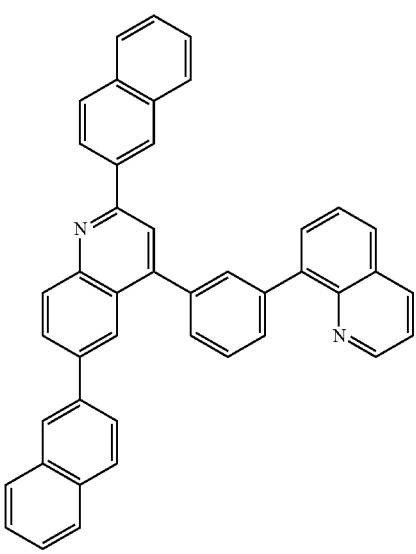
[A-8]
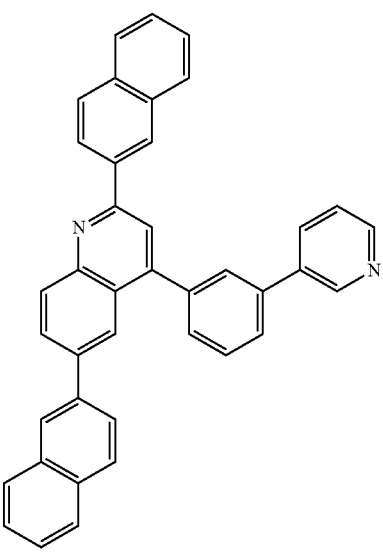

[A-9]
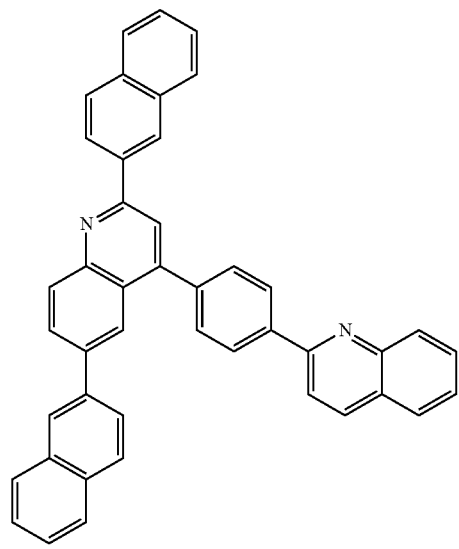
[A-12]
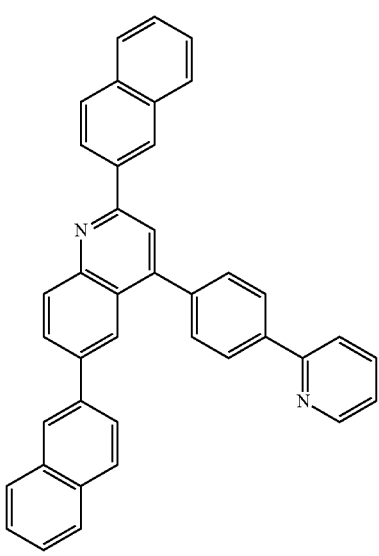
[A-10]
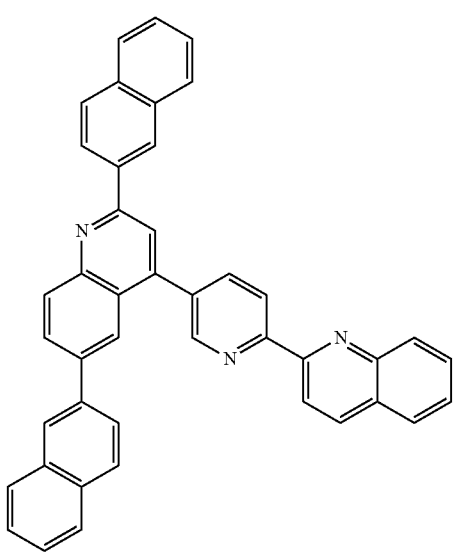
[A-13]
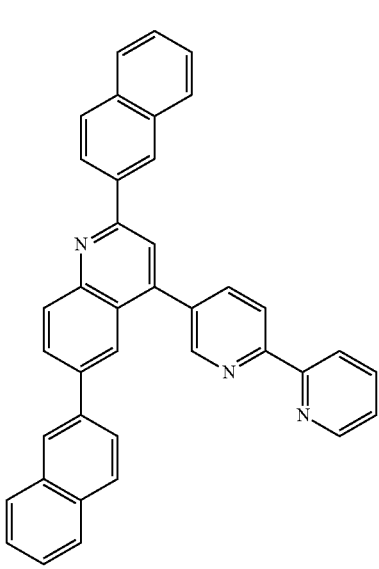
[A-11]
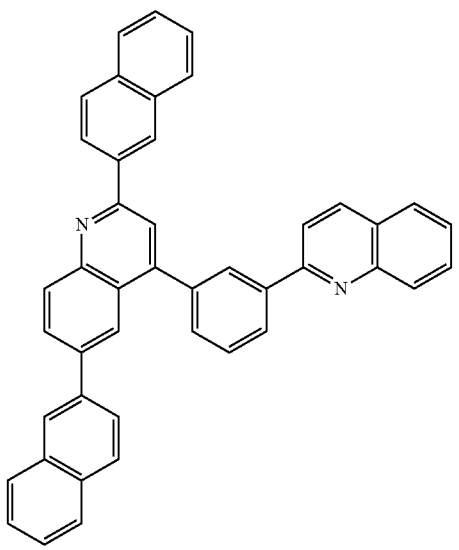
[A-14]
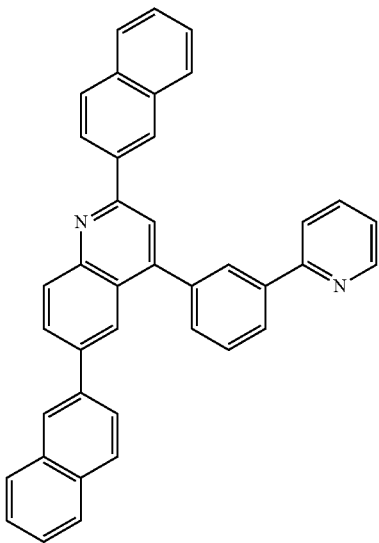

[A-15]
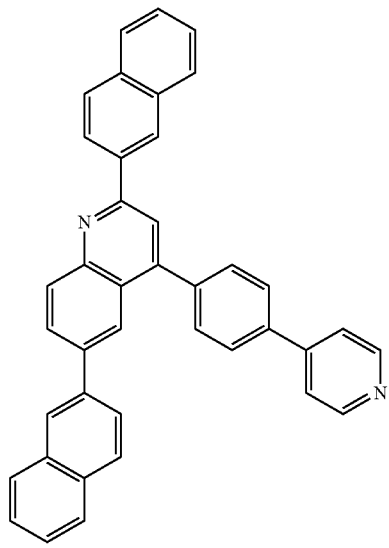
[A-18]
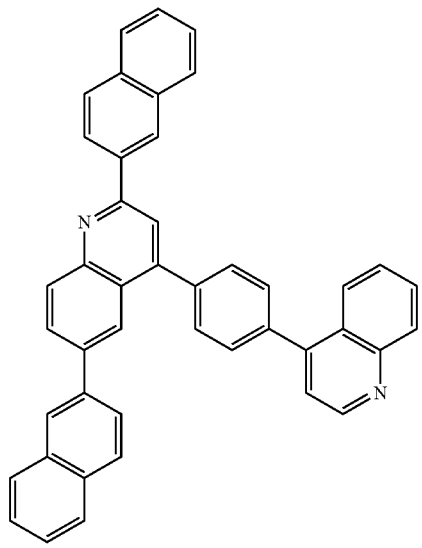
[A-16]
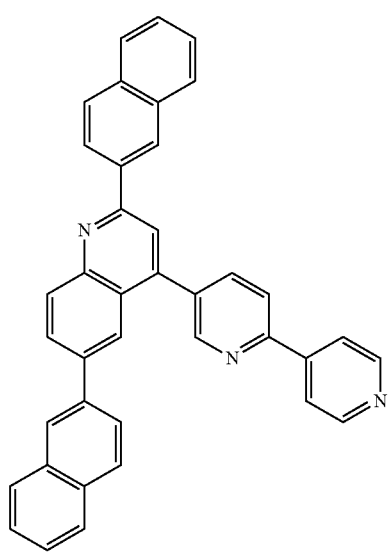
[A-19]
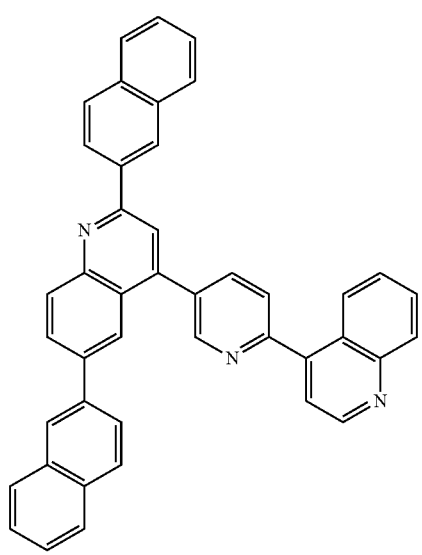
[A-17]
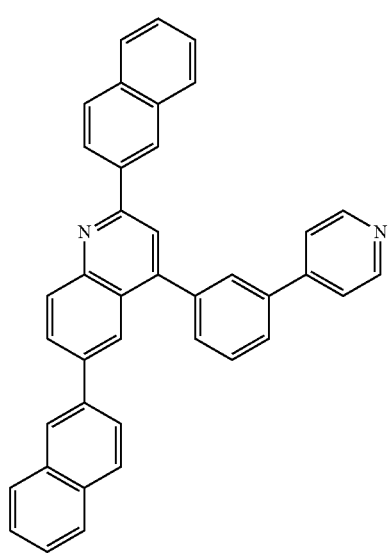
[A-20]
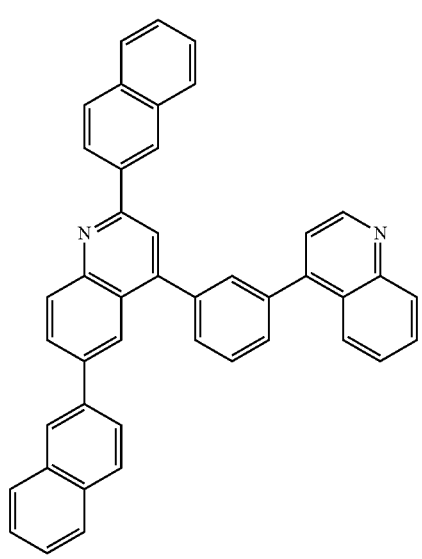

[A-21]
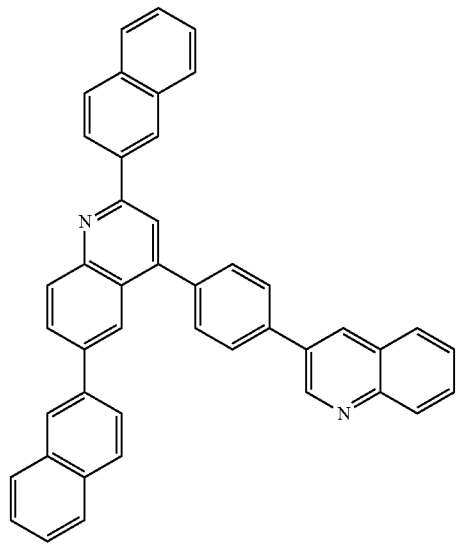
[A-24]
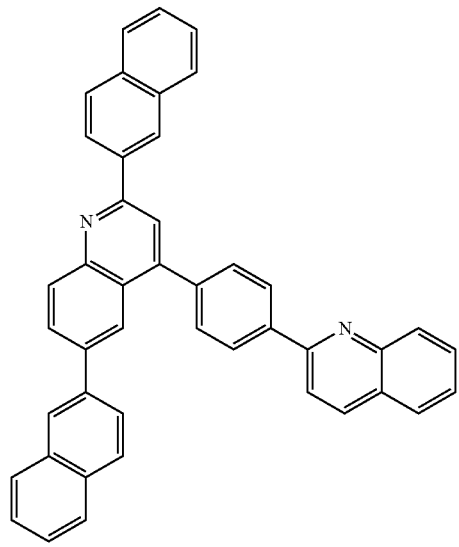
[A-22]
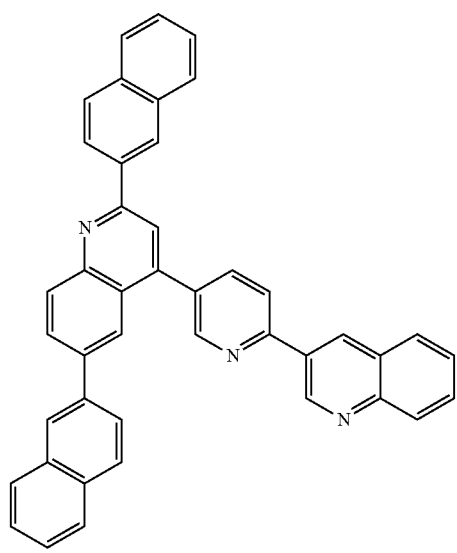
[A-25]
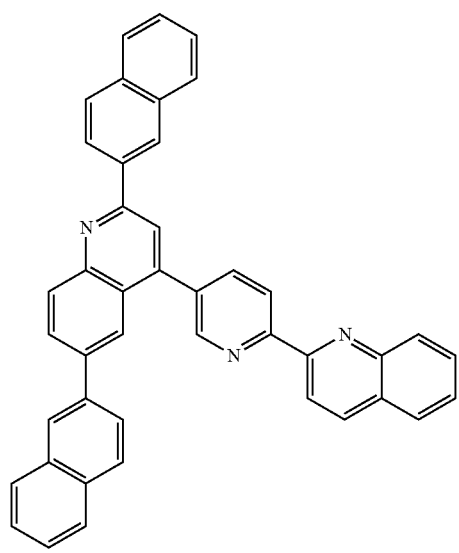
[A-23]
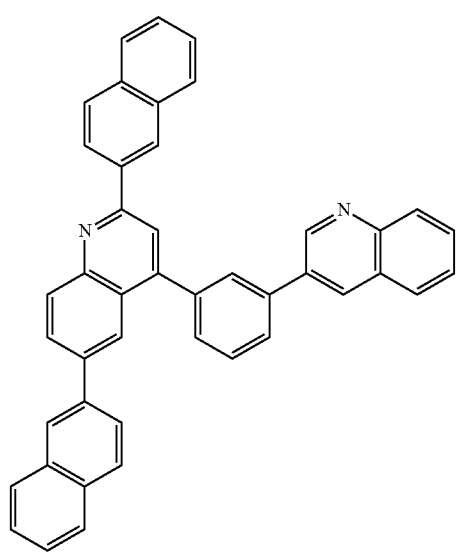
[A-26]
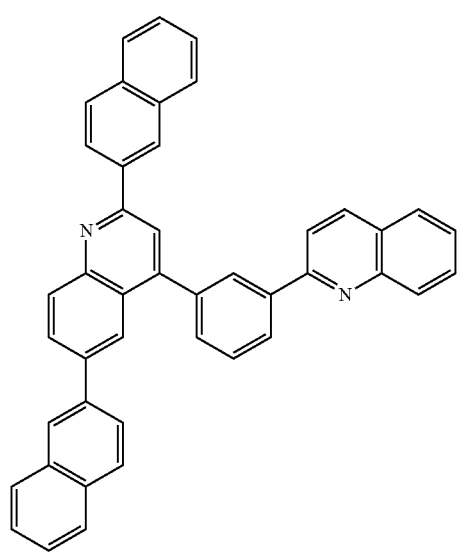

[A-27]
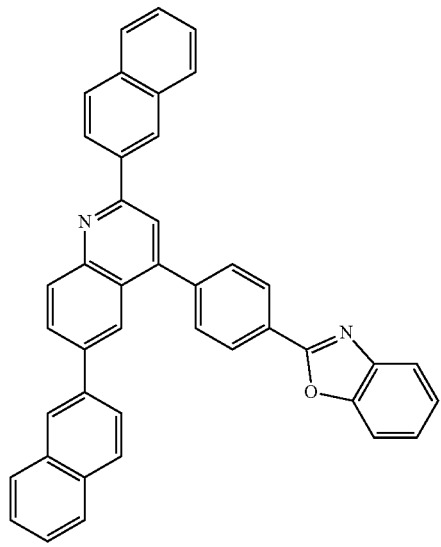
[A-30]
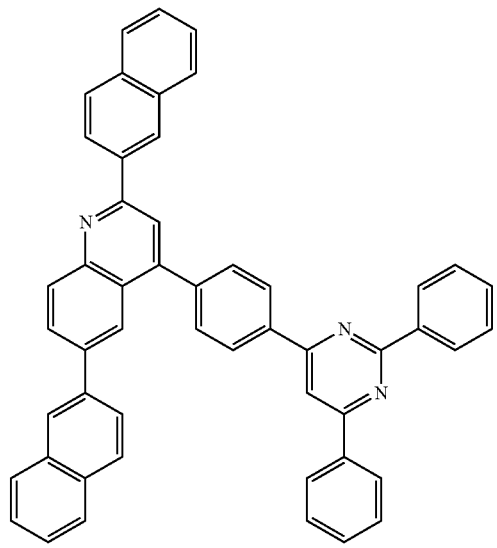
[A-28]
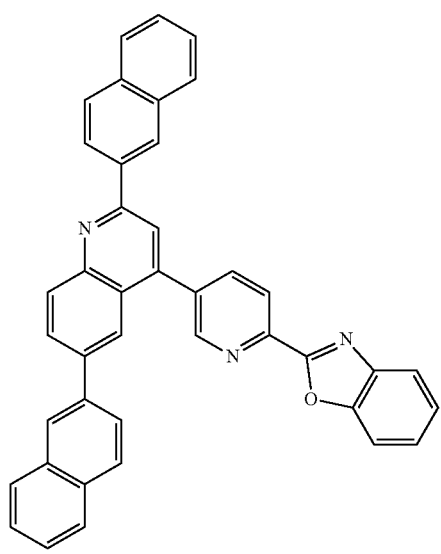
[A-31]
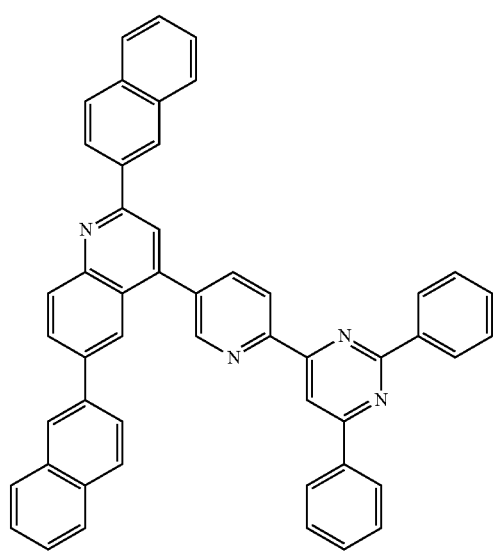
[A-29]
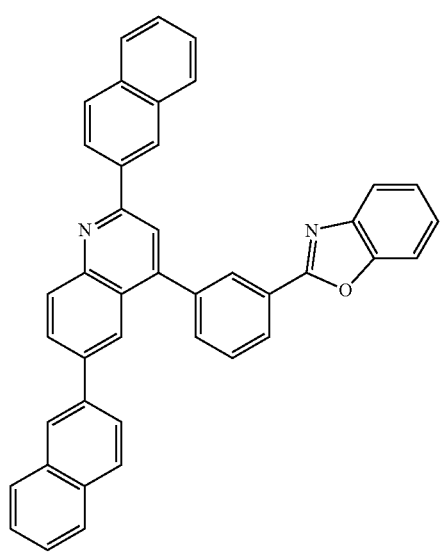
[A-32]
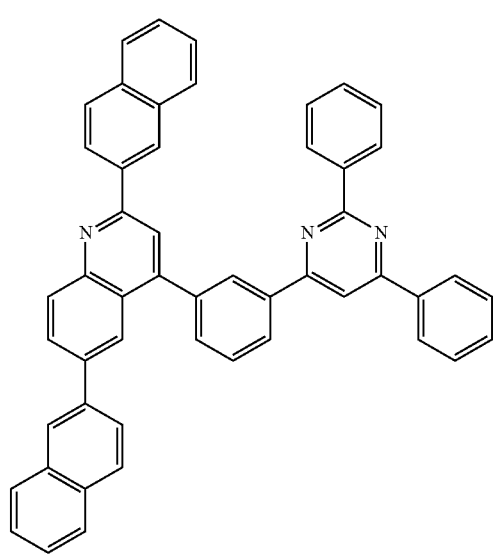

[A-33]
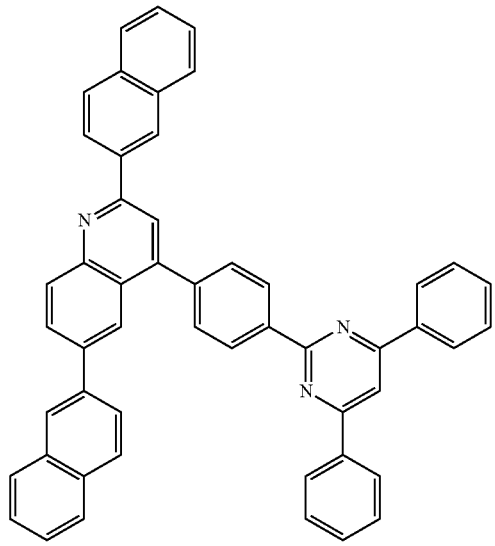
[A-36]
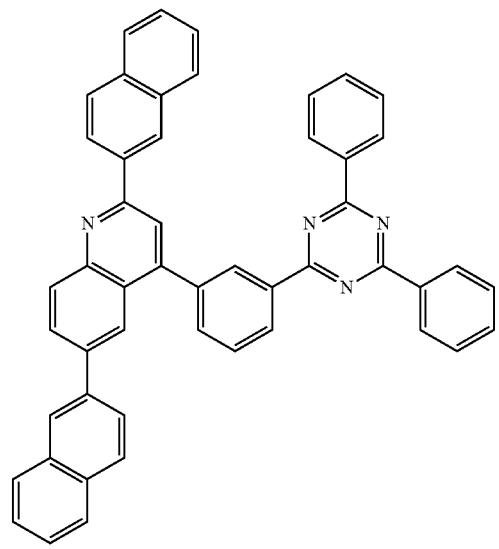
[A-34]
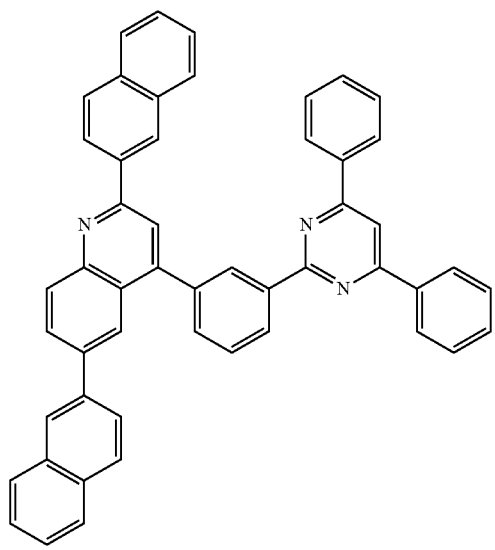
[A-37]
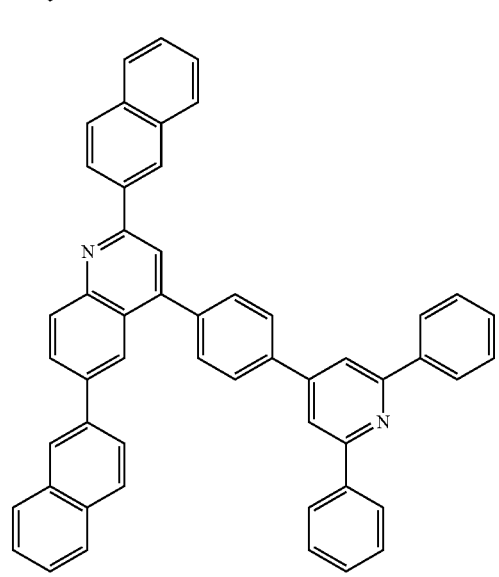
[A-35]
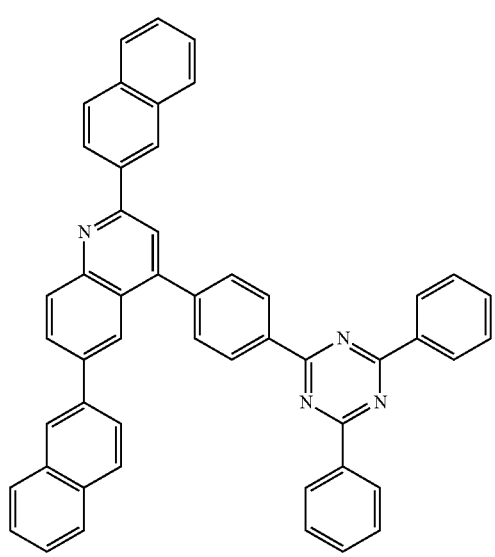
[A-38]

-continued
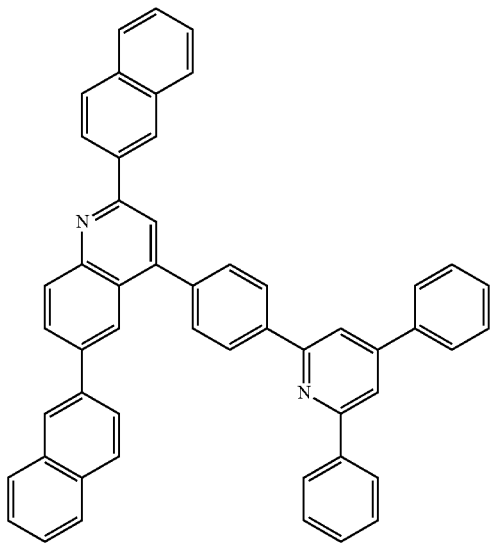
[A-39]
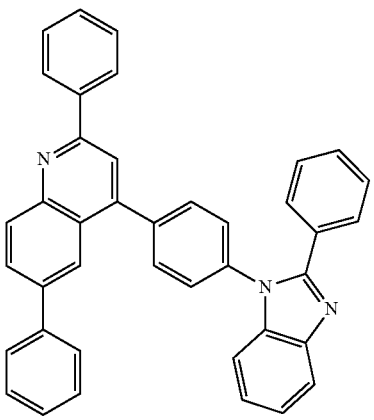
[A-42]
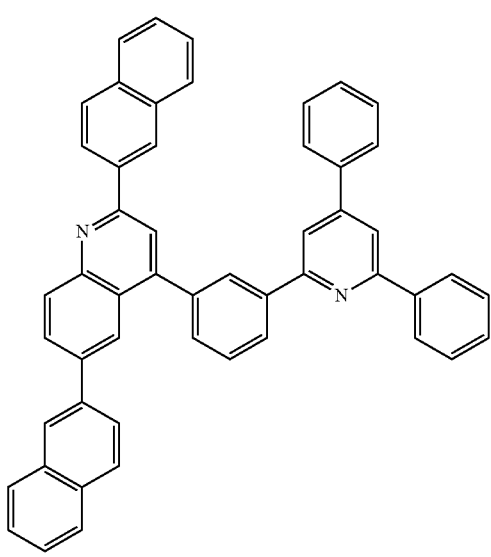
[A-40]
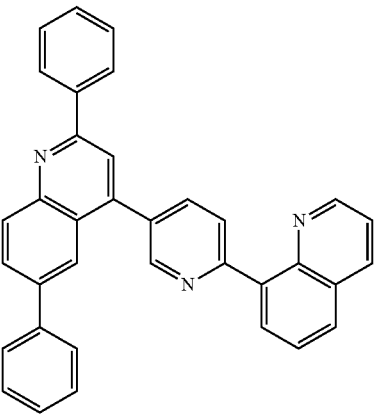
[A-43]
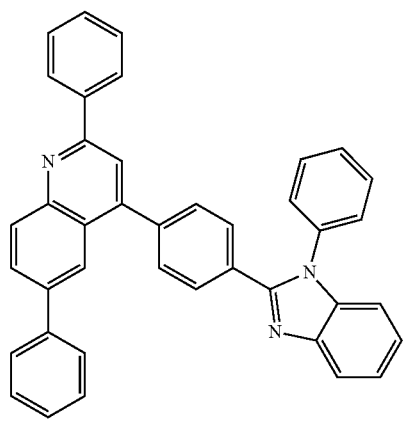
[A-41]
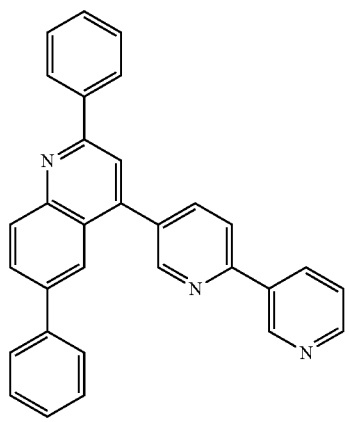
[A-44]

-continued
[A-45]
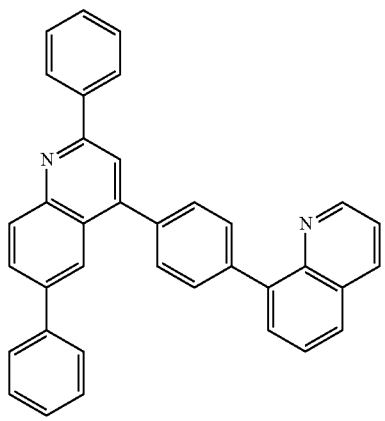
[A-46]
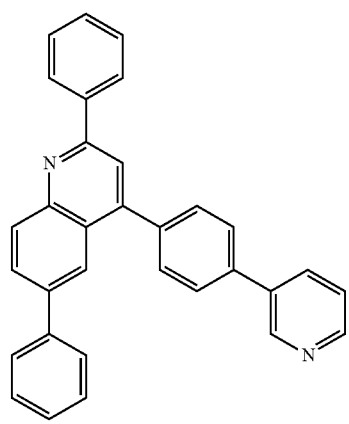
[A-47]
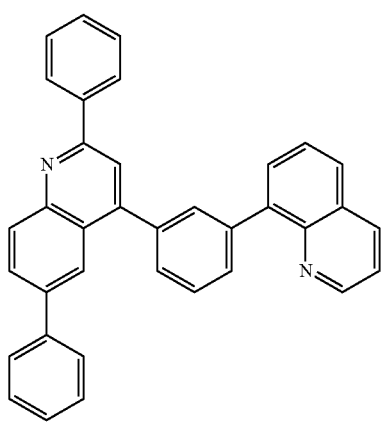
[A-48]
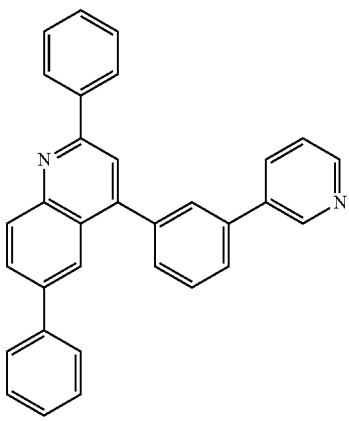
[A-49]
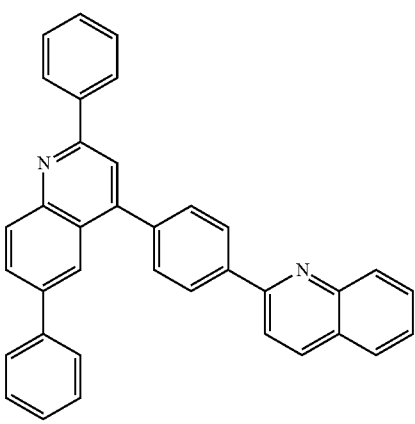
[A-50]
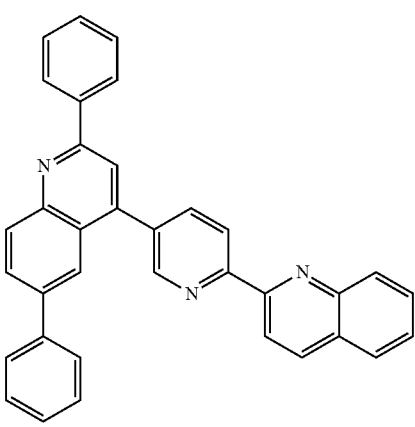

[A-51]
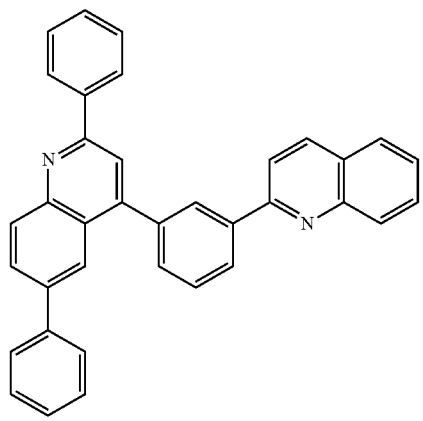
[A-52]
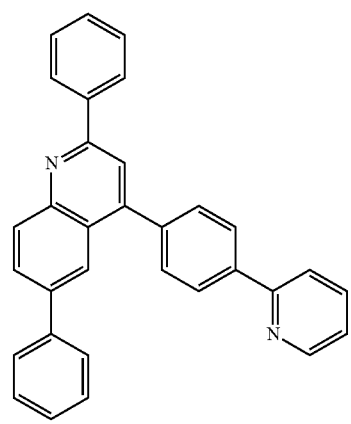
[A-53]
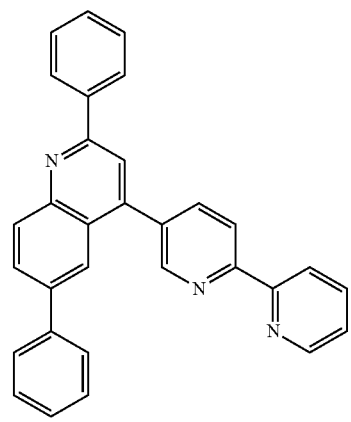
[A-54]
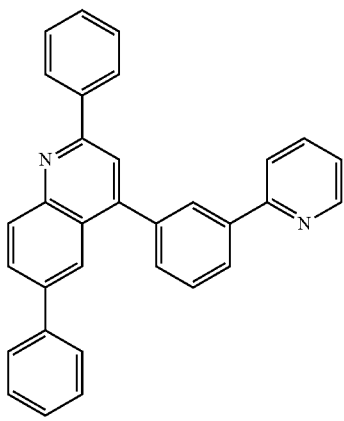
[A-55]
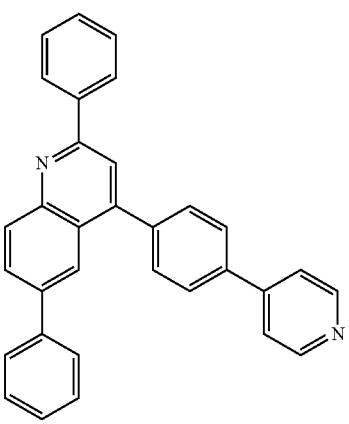
[A-56]
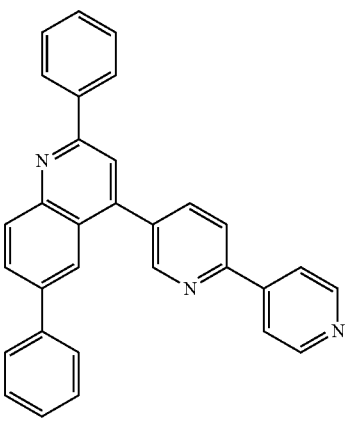

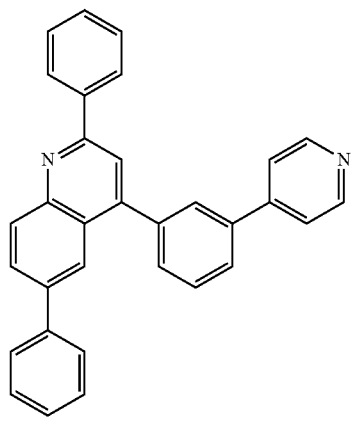
[A-57]
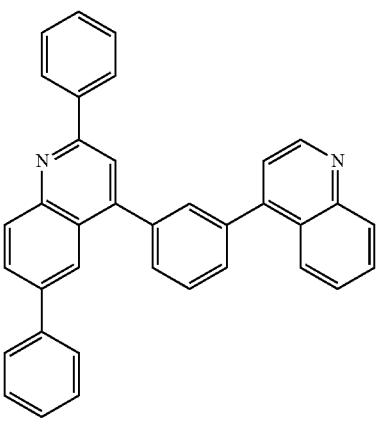
[A-60]
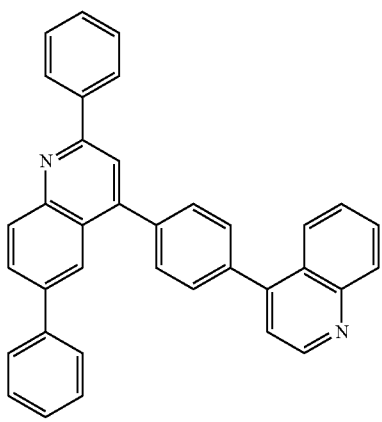
[A-58]
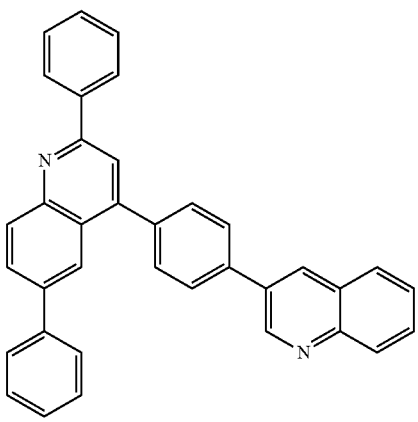
[A-61]
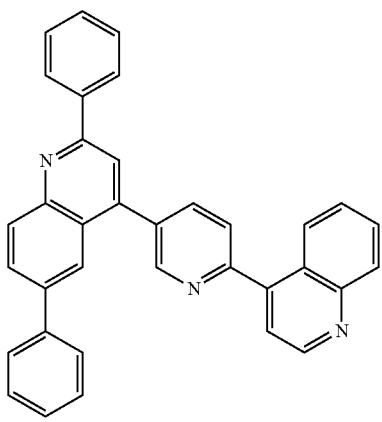
[A-59]
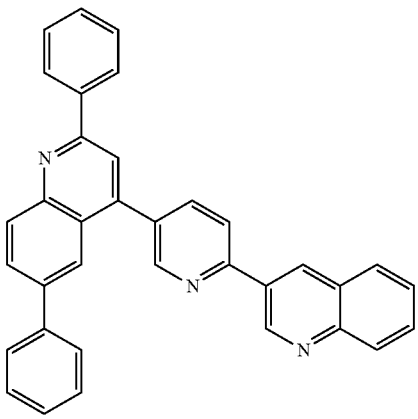
[A-62]

[A-63]
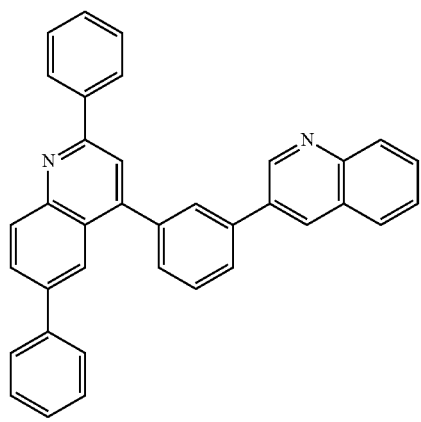
[A-66]
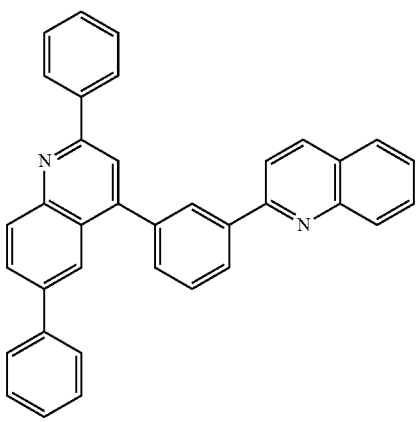
[A-64]
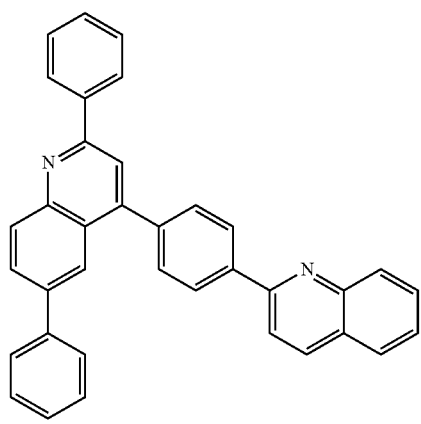
[A-67]
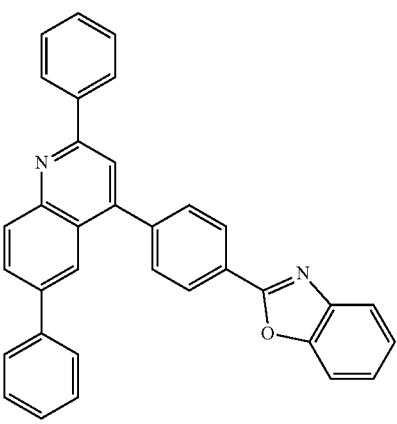
[A-65]
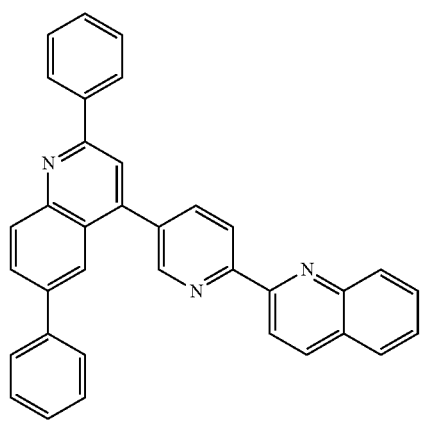
[A-68]
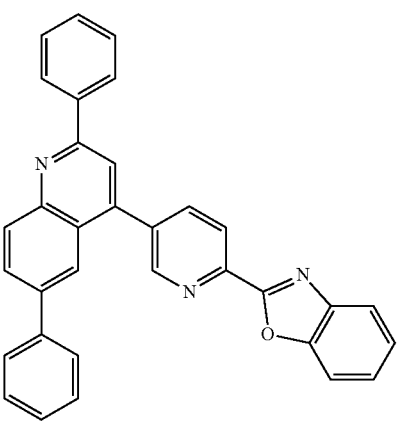

[A-69]
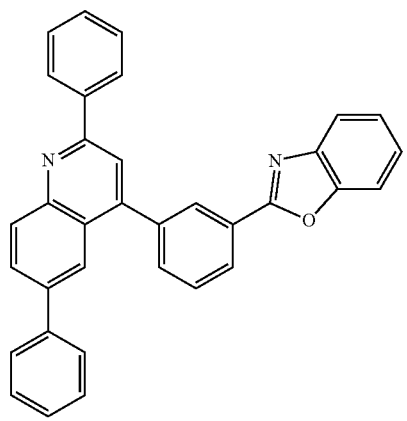
[A-72]
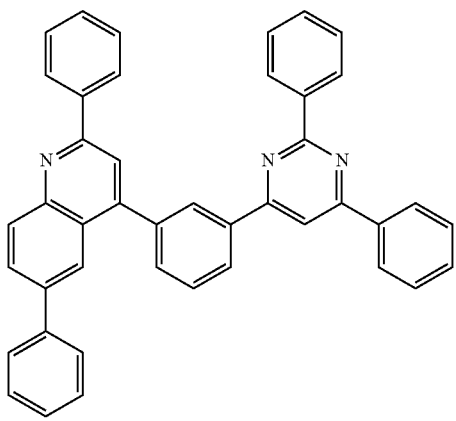
[A-70]
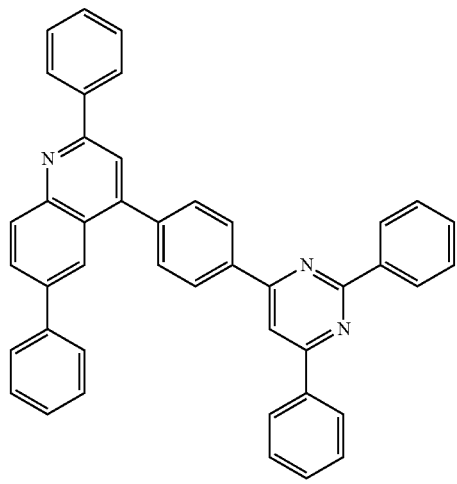
[A-73]
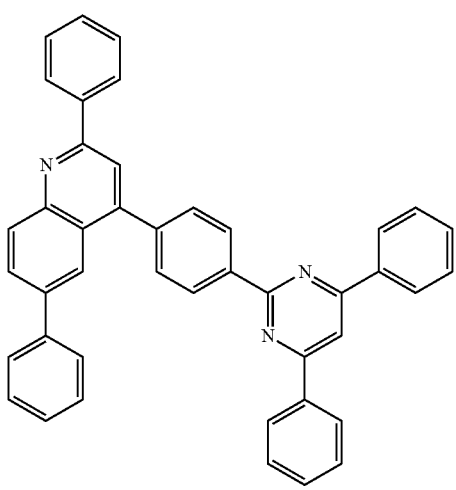
[A-71]
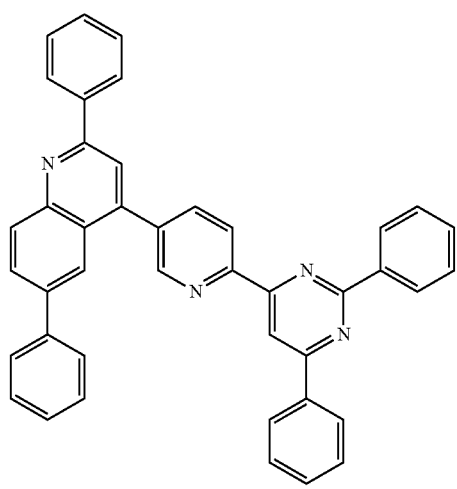
[A-74]
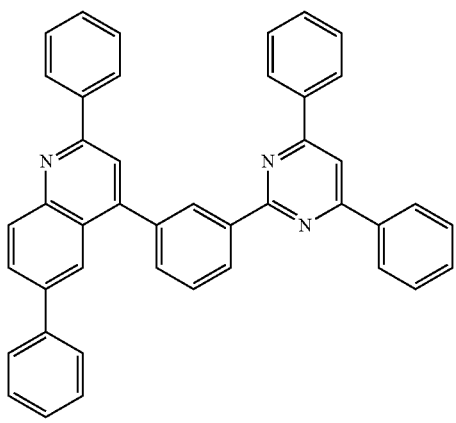

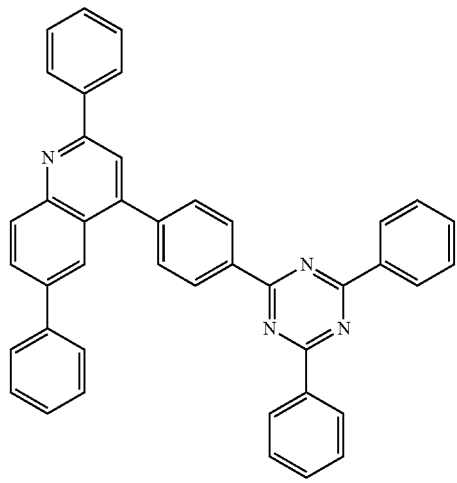
[A-75]
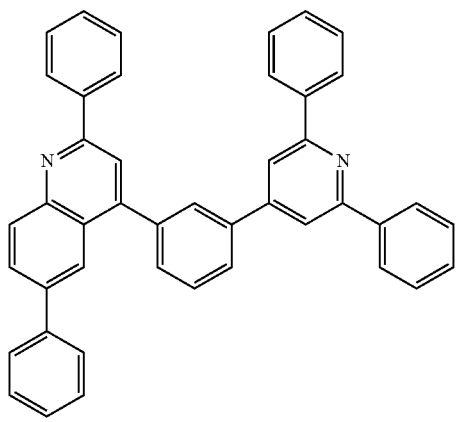
[A-78]
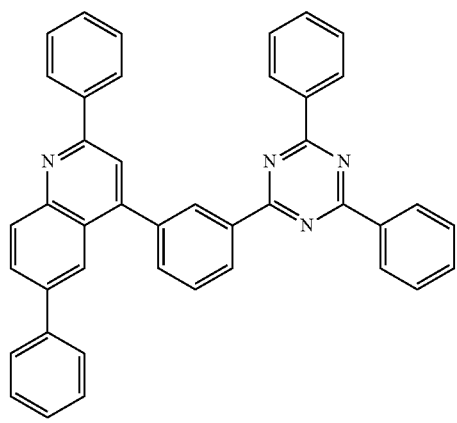
[A-76]
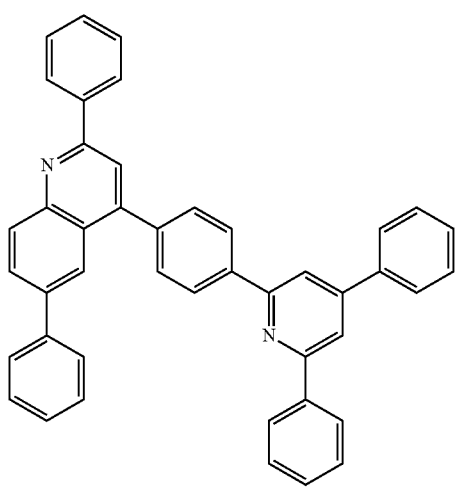
[A-79]
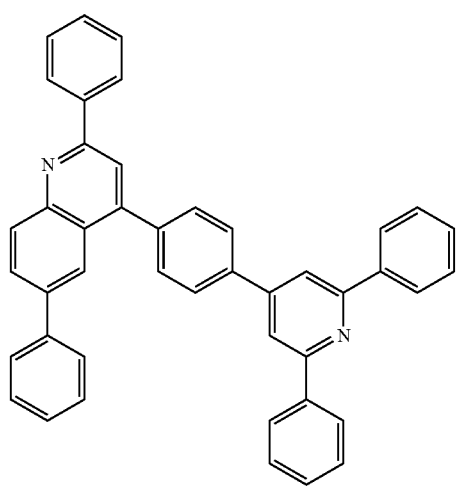
[A-77]
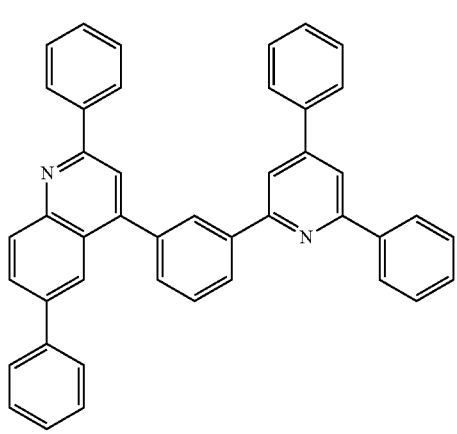
[A-80]

[A-81]
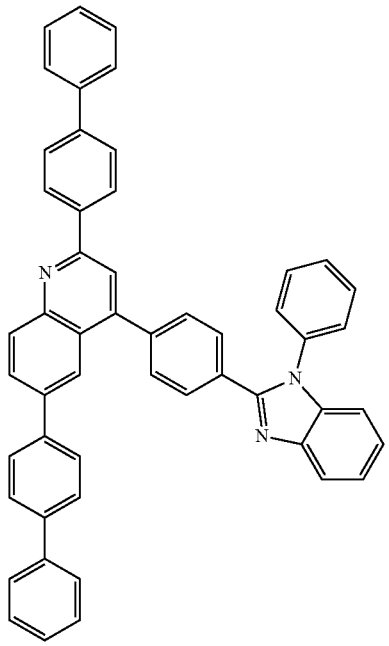
[A-83]
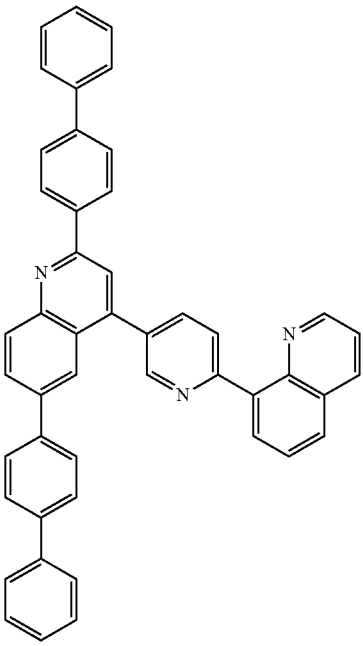
[A-82]
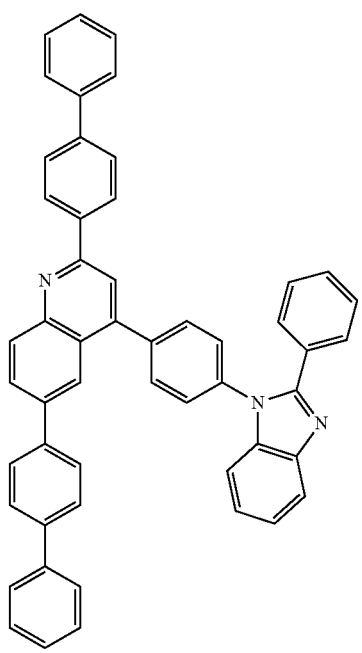
[A-84]
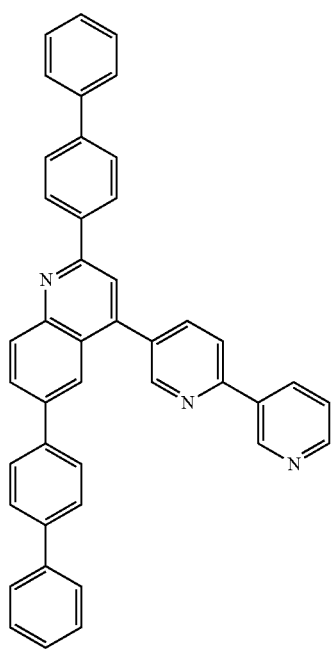

[A-85]
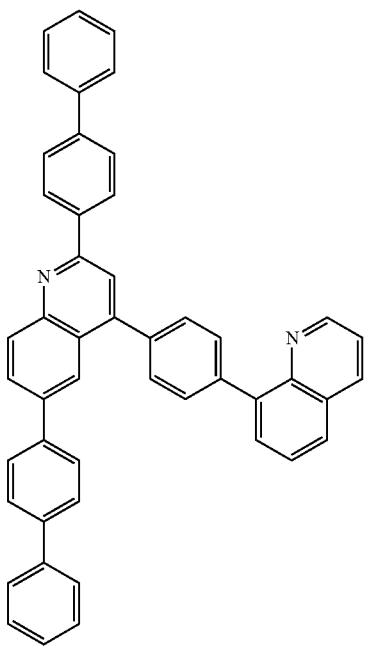
[A-87]
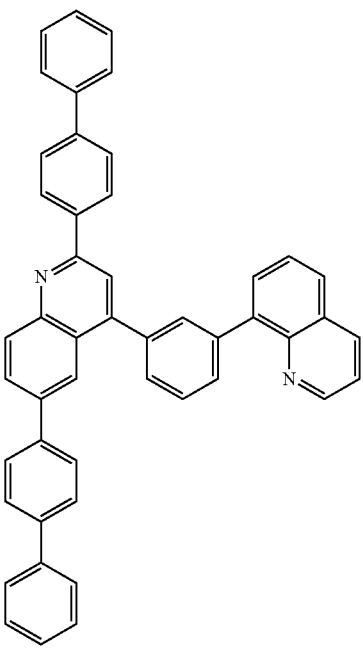
[A-86]
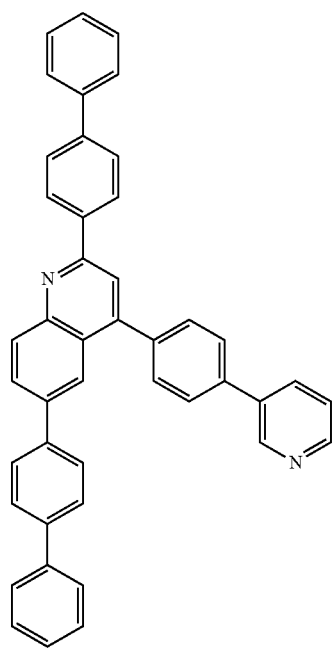
[A-88]
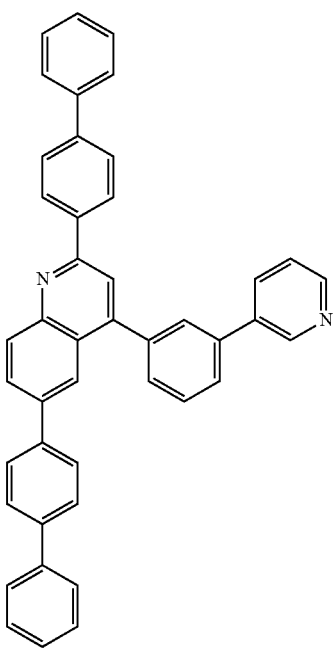

[A-89]
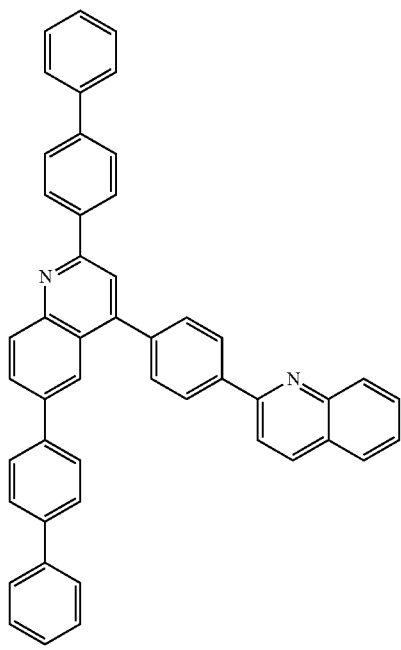
[A-91]
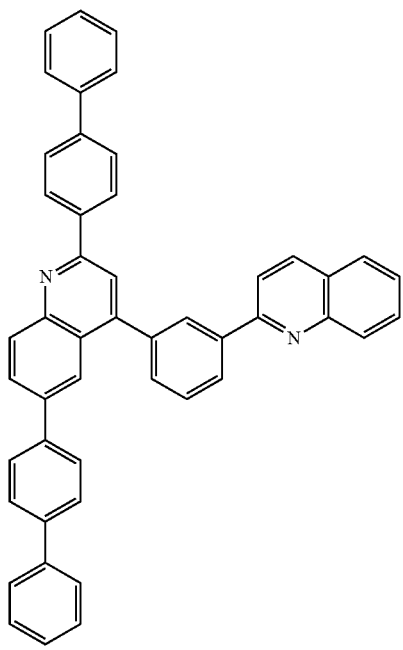
[A-90]
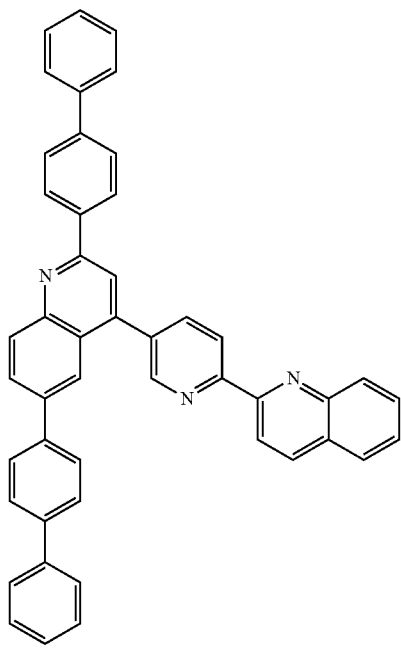
[A-92]
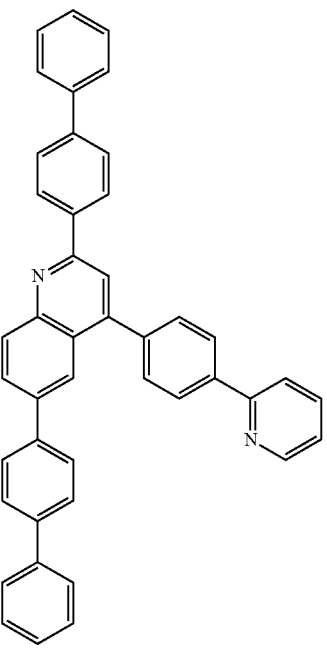

[A-93]
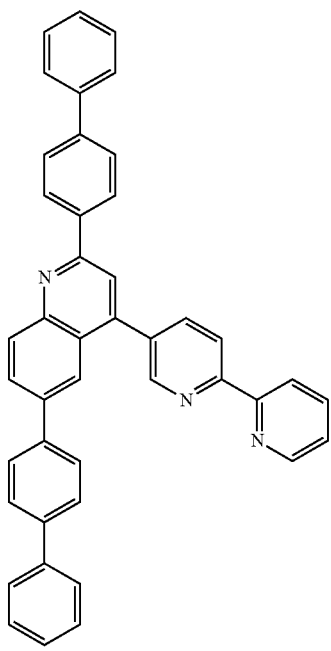
[A-94]
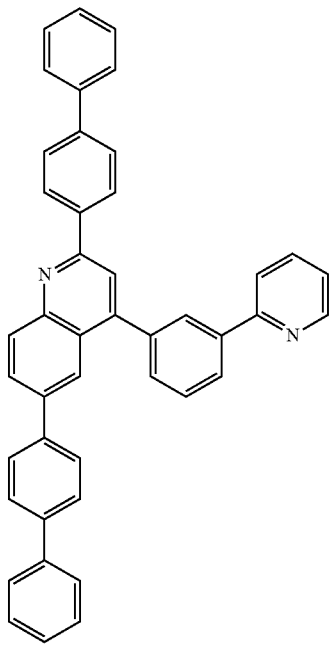
[A-95]
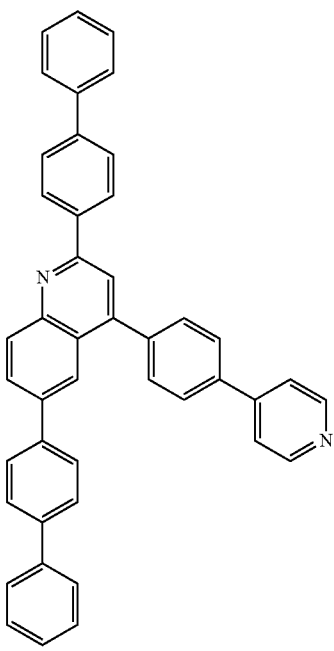
[A-96]
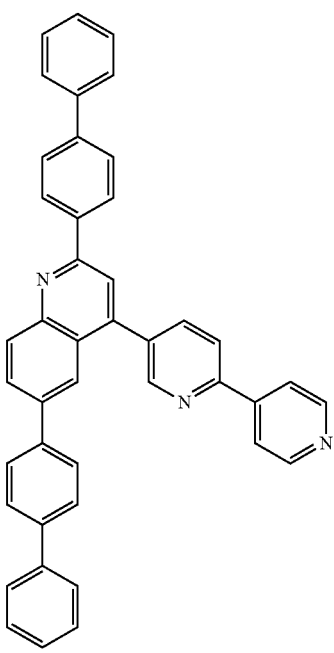

[A-97]
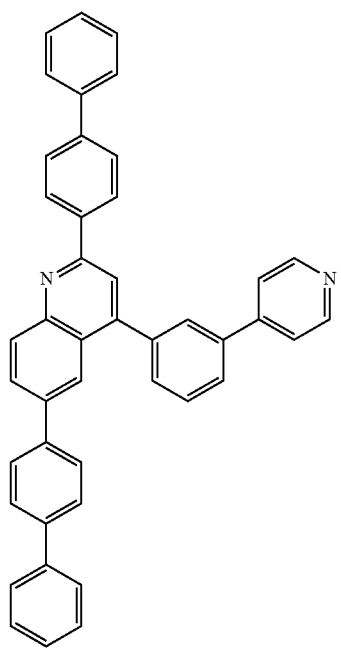
[A-99]
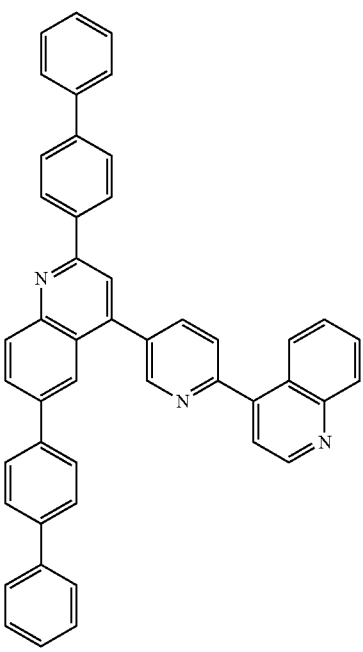
[A-98]
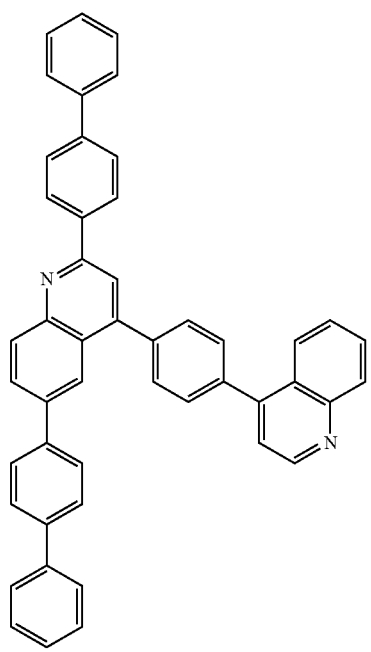
[A-100]
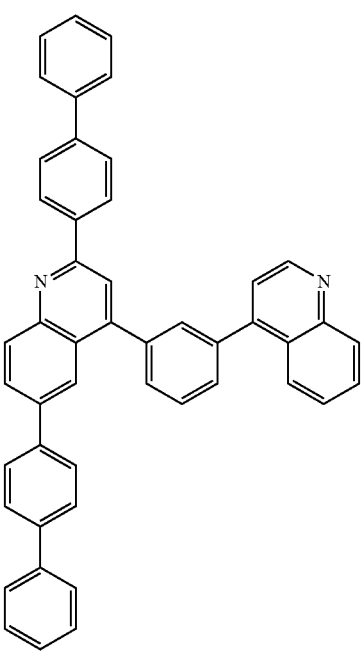

[A-101]
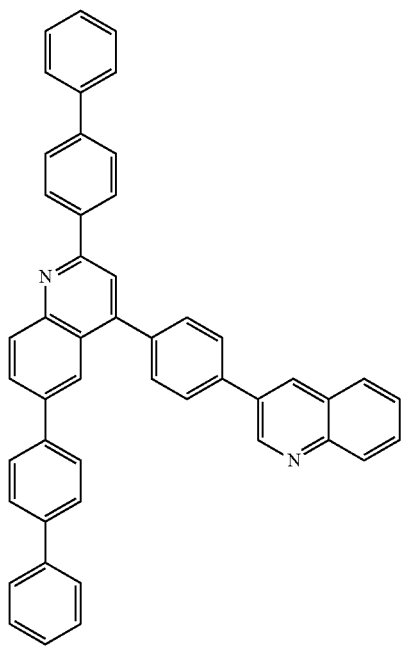
[A-102]
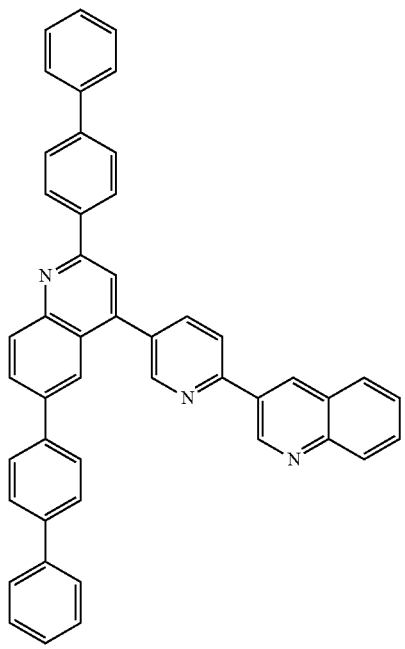
[A-103]
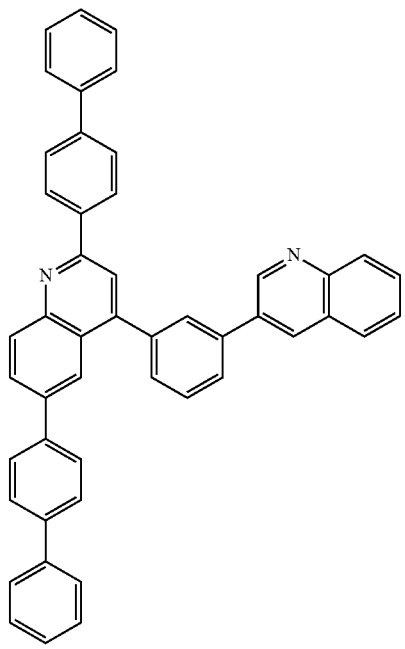
[A-104]
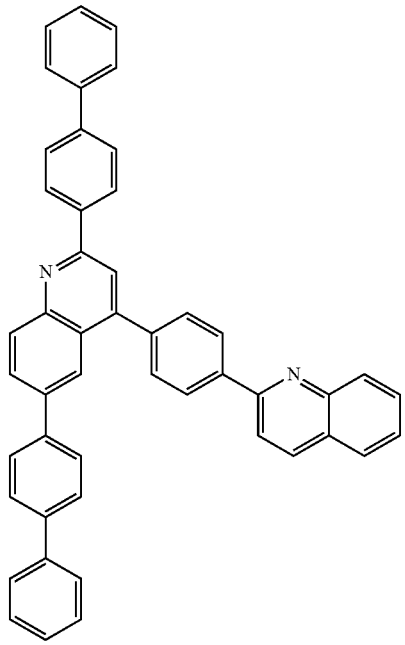

[A-105]
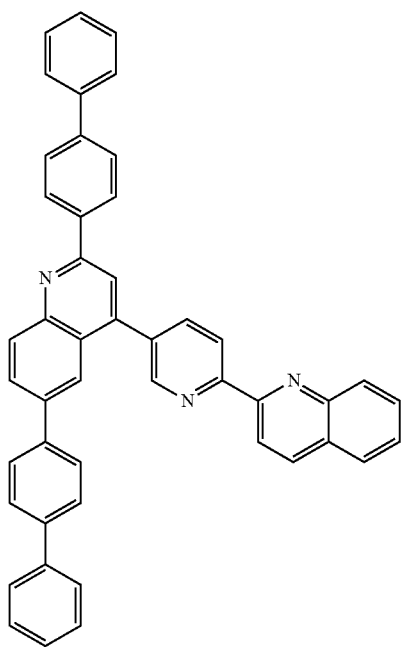
[A-107]
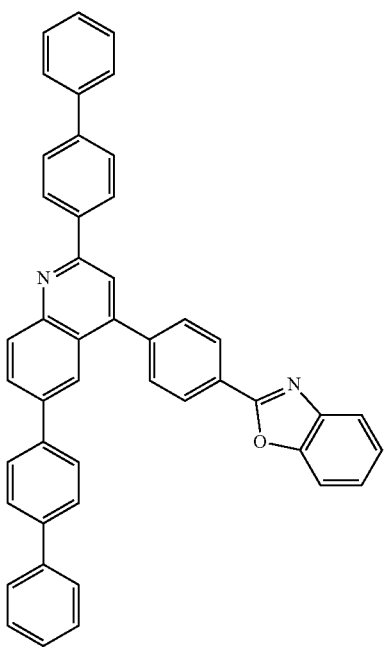
[A-106]
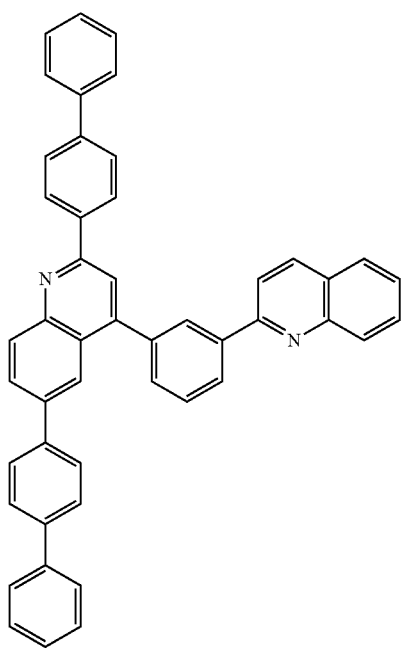
[A-108]
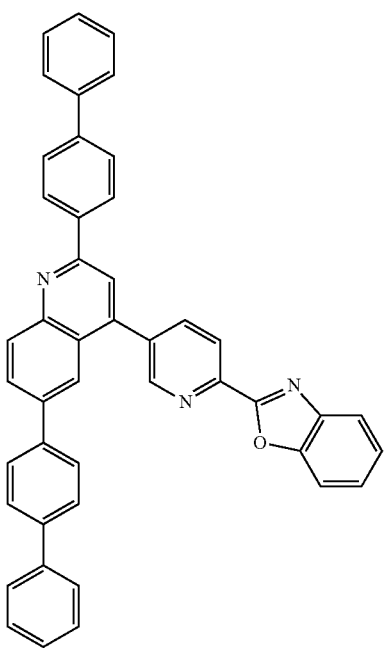

[A-109]
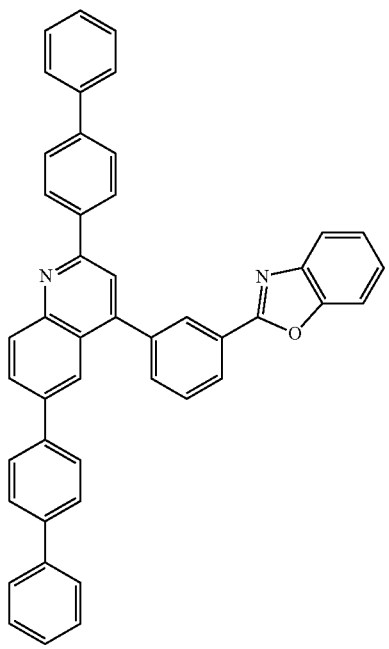
[A-110]
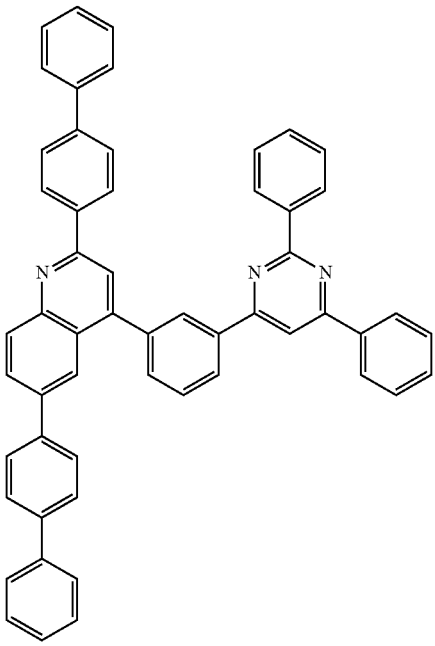
[A-111]
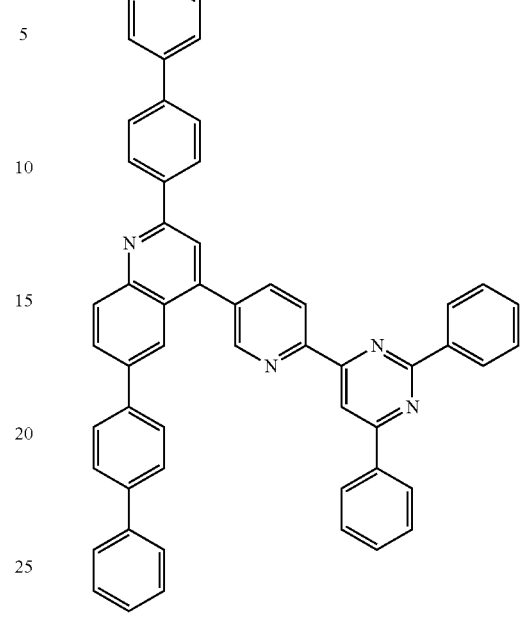
[A-112]

[A-113]
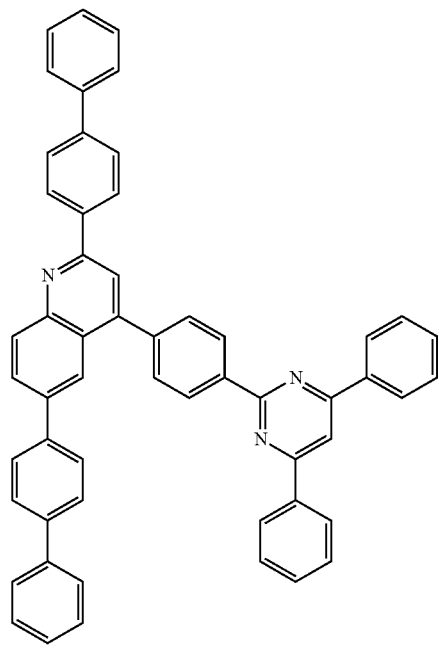
[A-115]
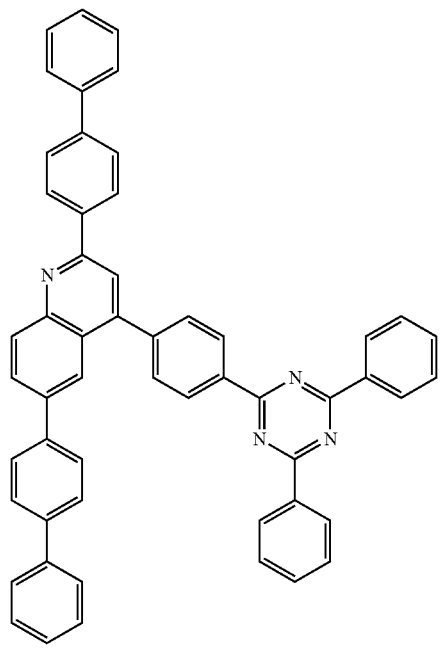
[A-114]
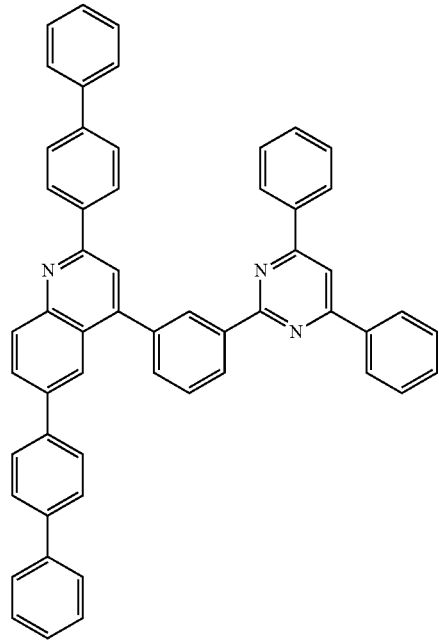
[A-116]
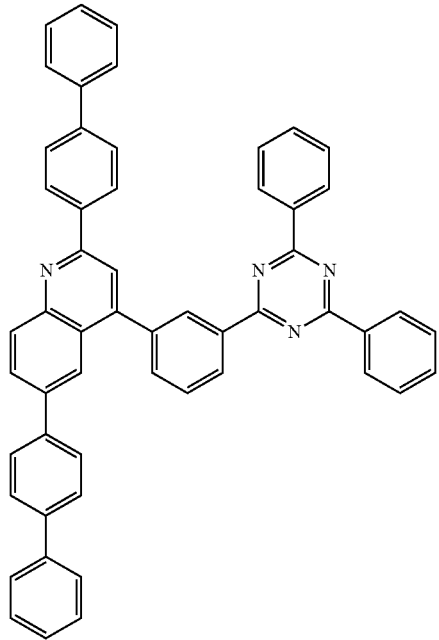

[A-117]
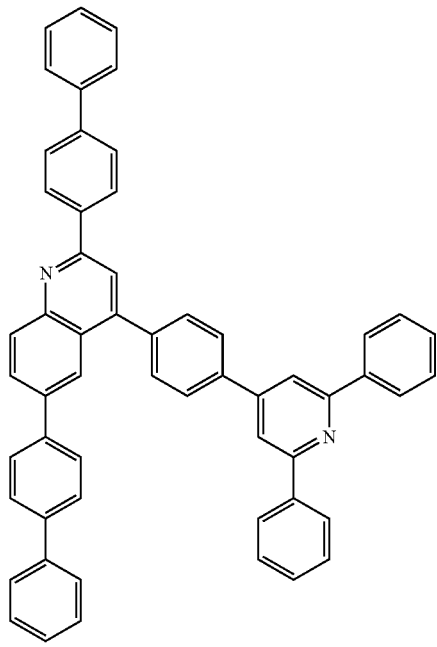
[A-119]
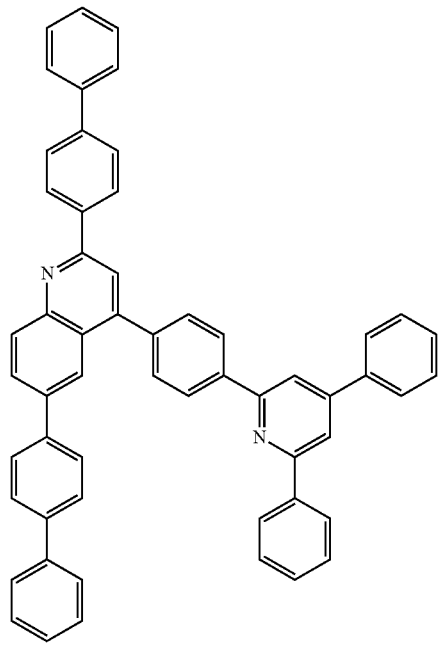
[A-118]
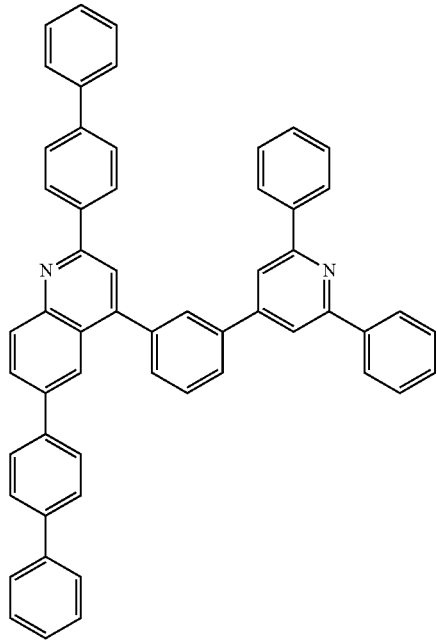
[A-120]
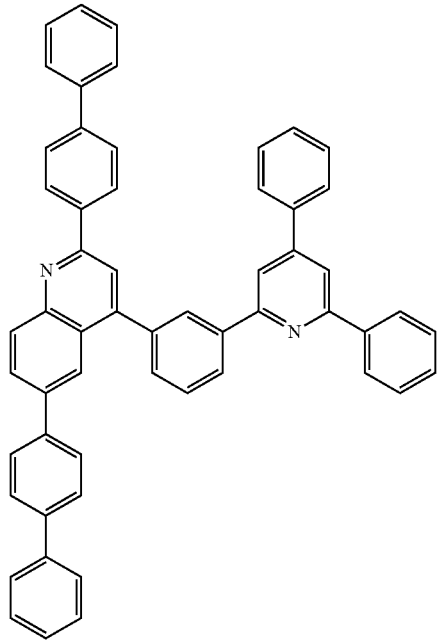

[A-121]
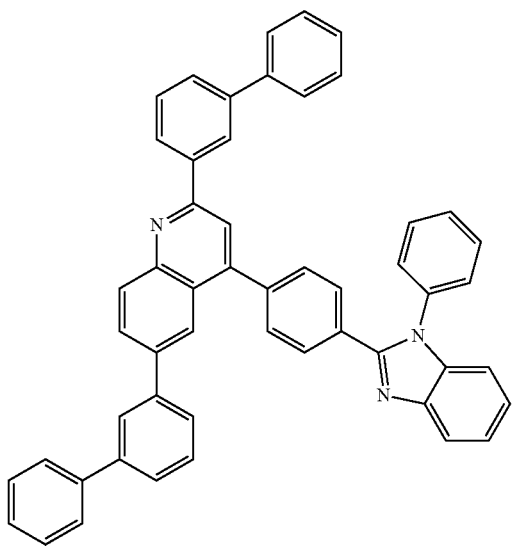
[A-123]
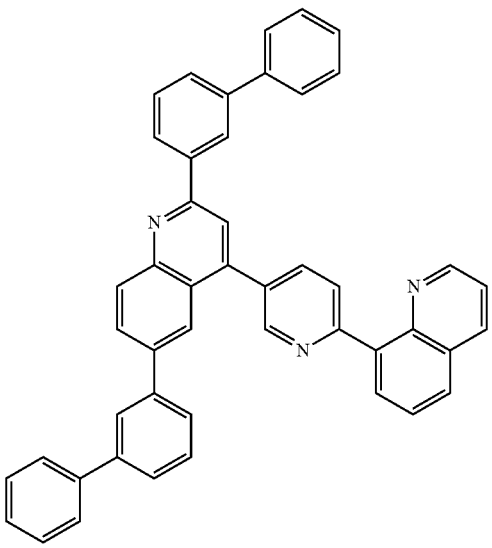
[A-122]
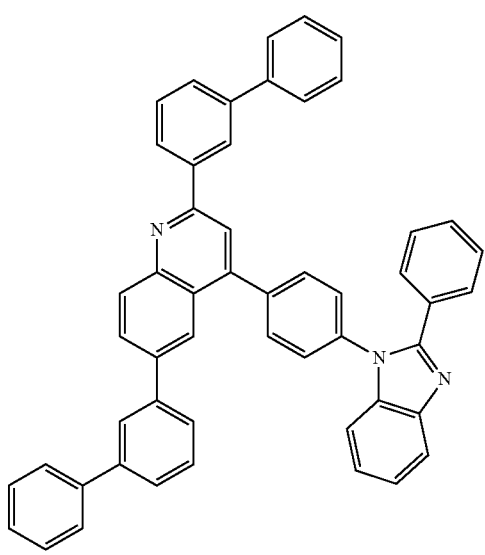
[A-124]
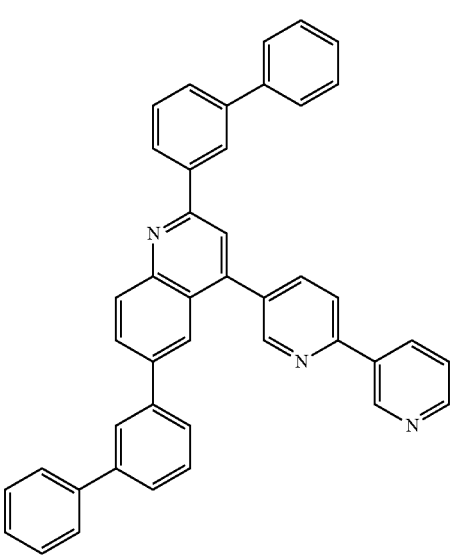

[A-125]
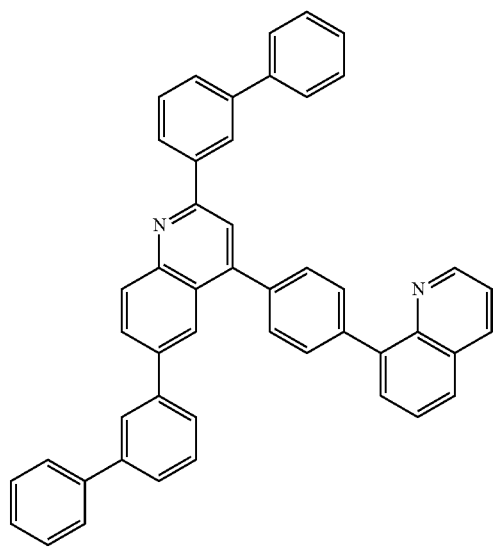
[A-127]
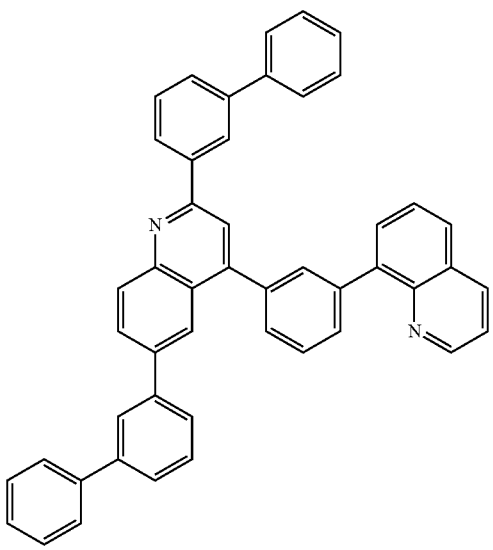
[A-126]
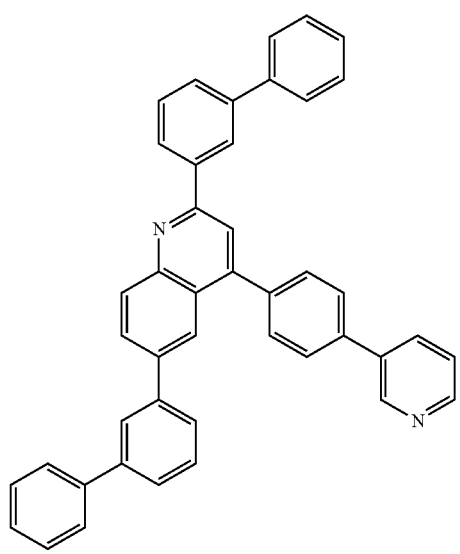
[A-128]
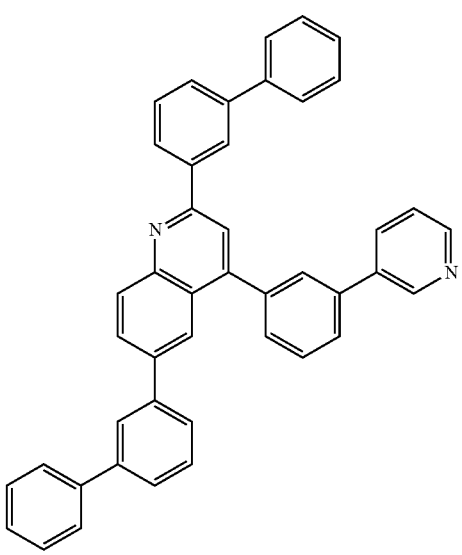

[A-129]
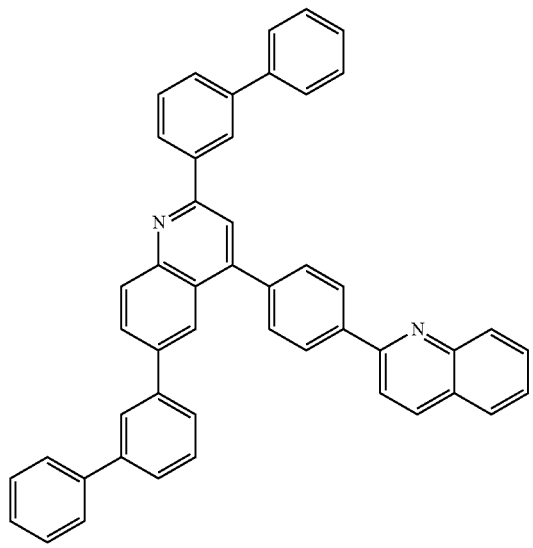
[A-131]
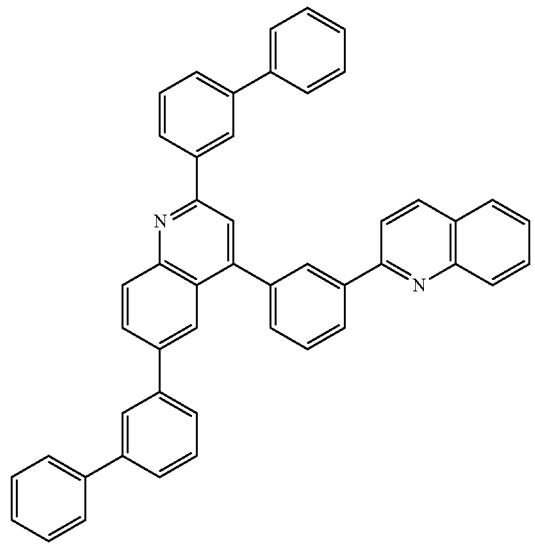
[A-130]
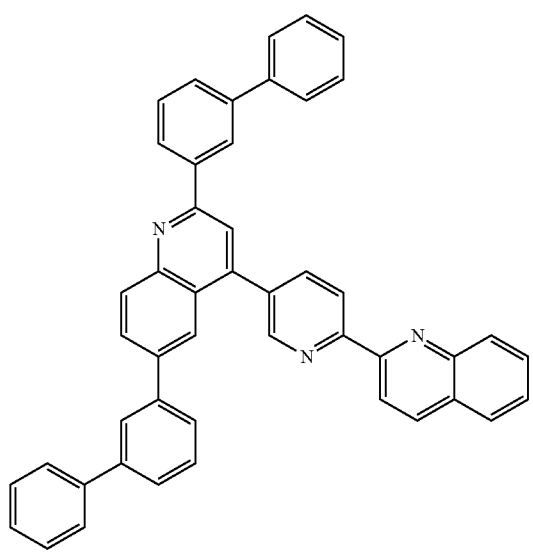
[A-132]
[A-133]
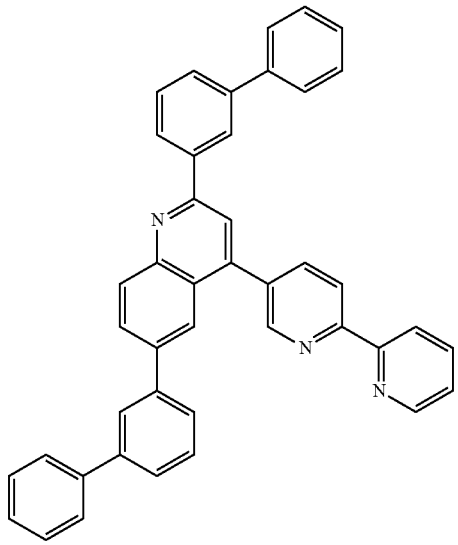

-continued
[A-134]
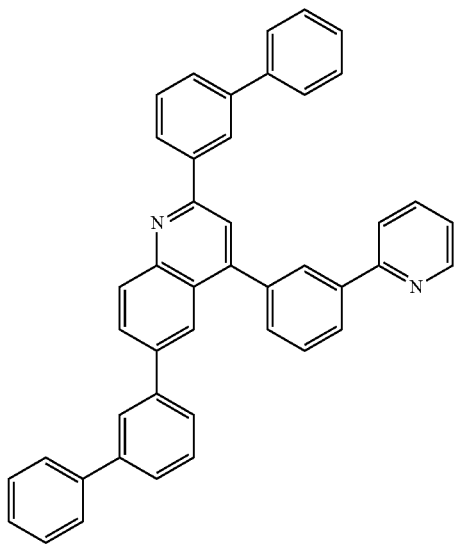
[A-135]
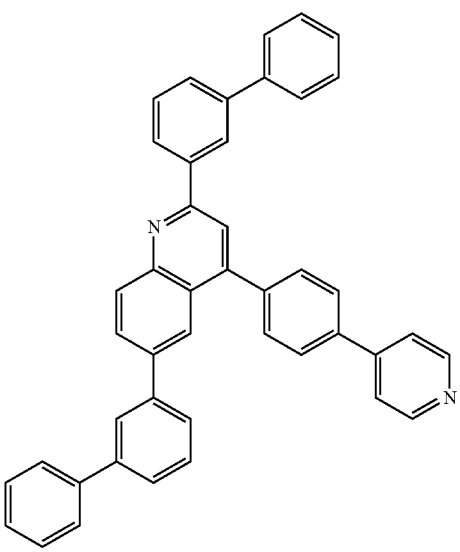
[A-136]
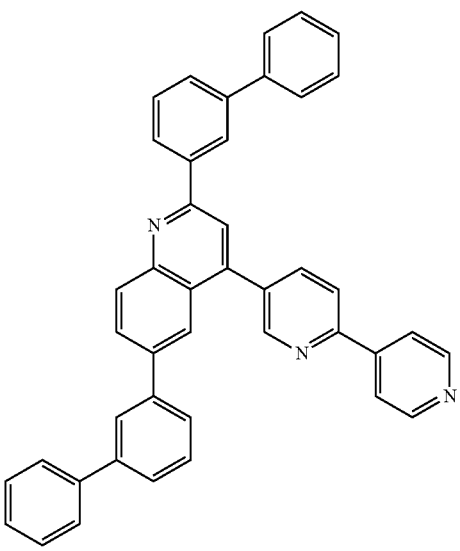
-continued
[A-137]
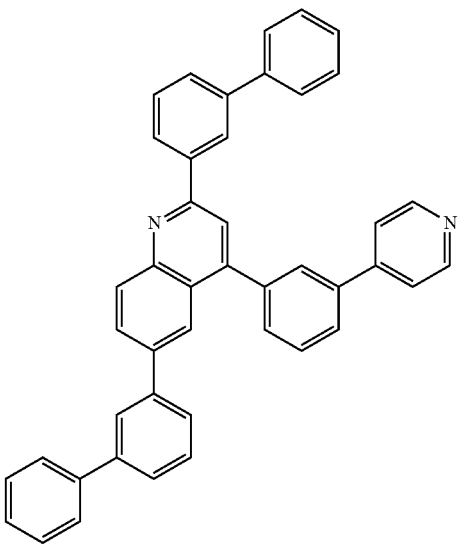
[A-138]
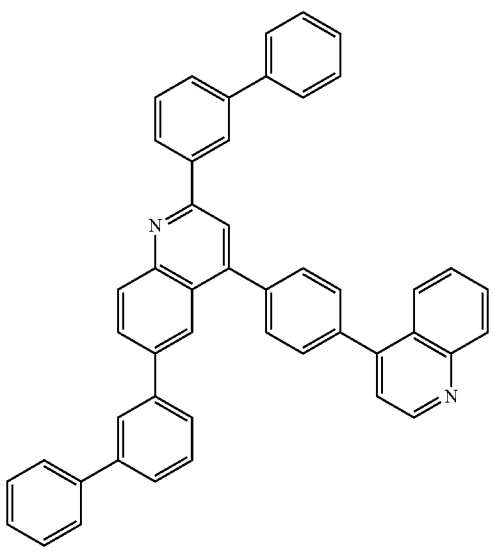

[A-139]
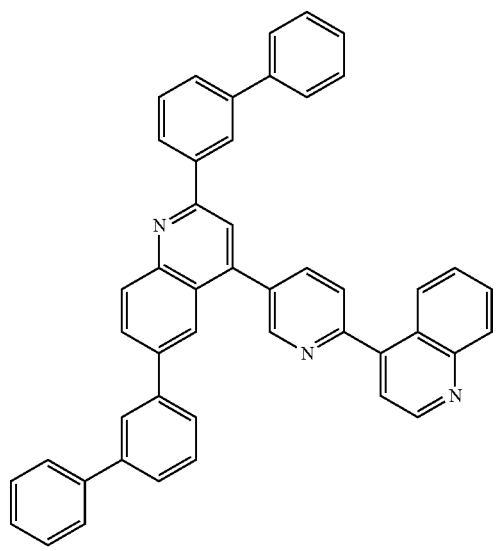
[A-141]
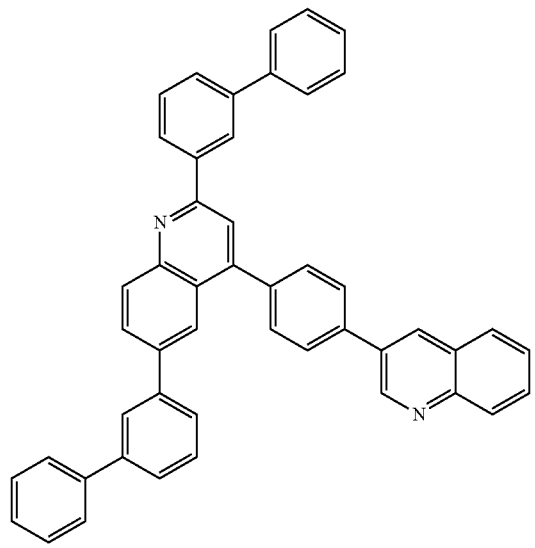
[A-140]
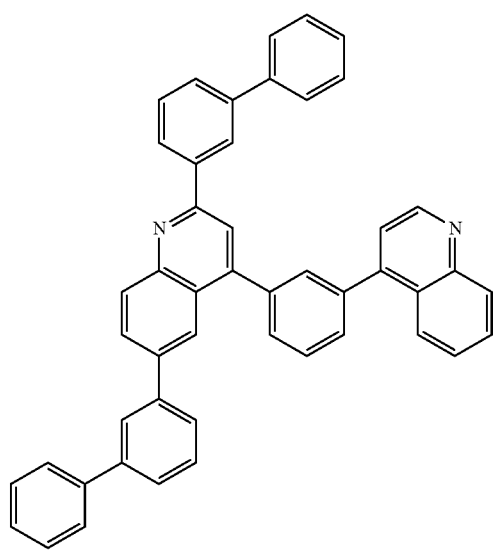
[A-142]
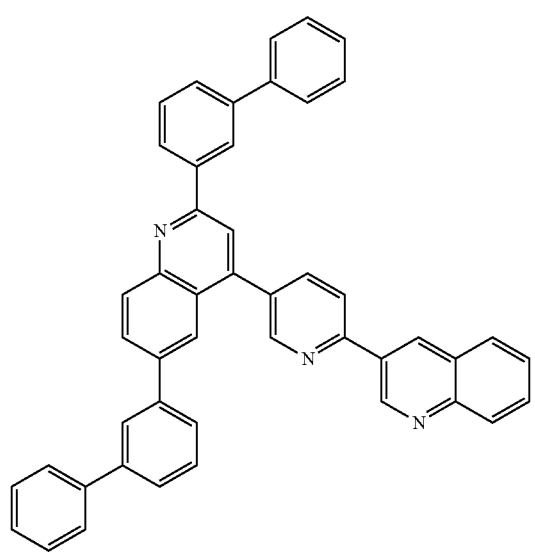

[A-143]
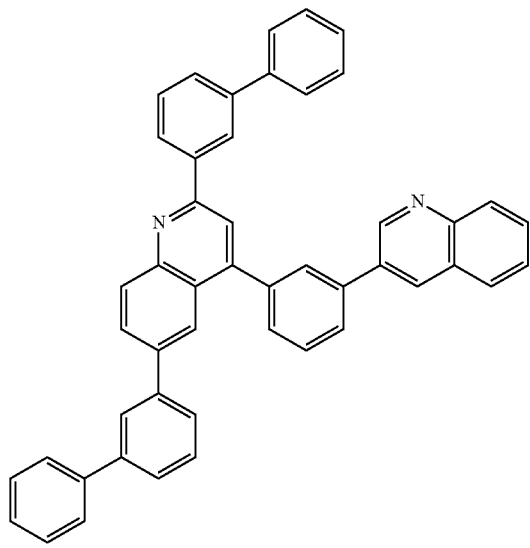
[A-145]
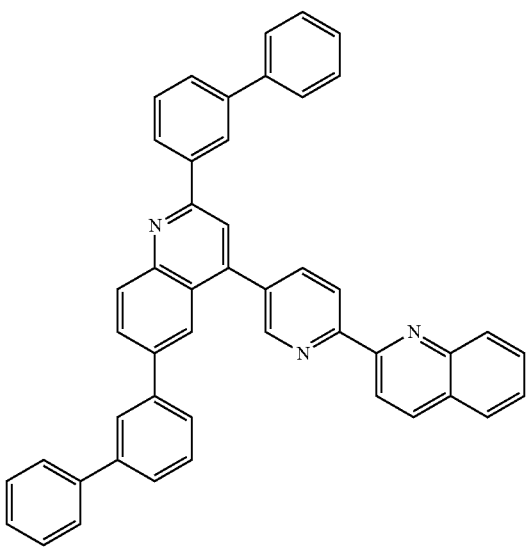
[A-144]
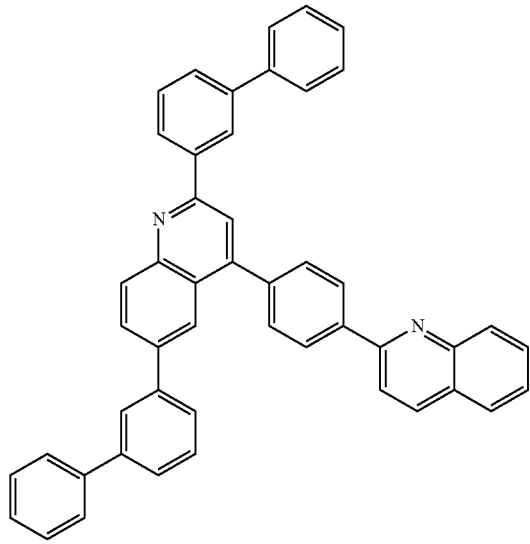
[A-146]
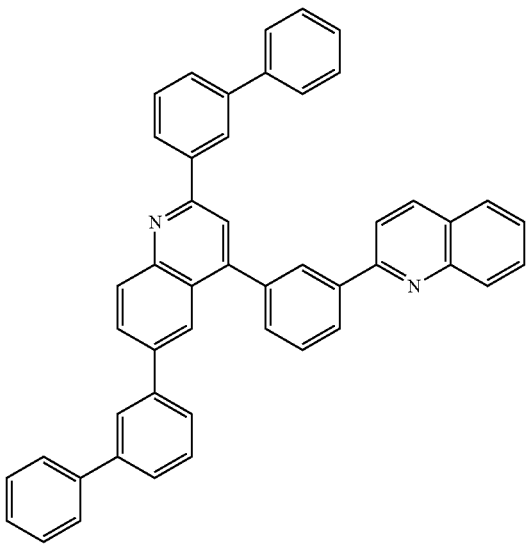

[A-147]
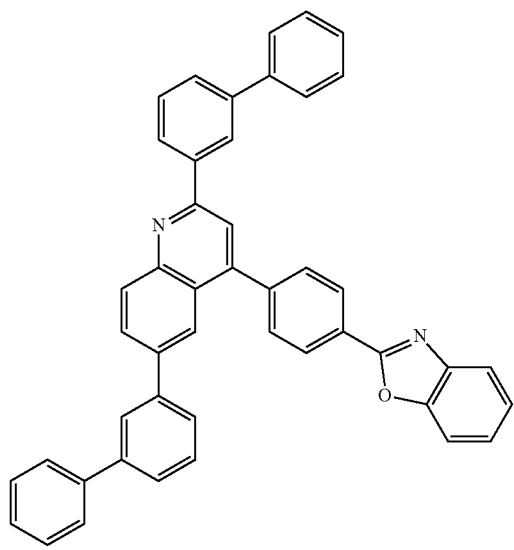
[A-149]
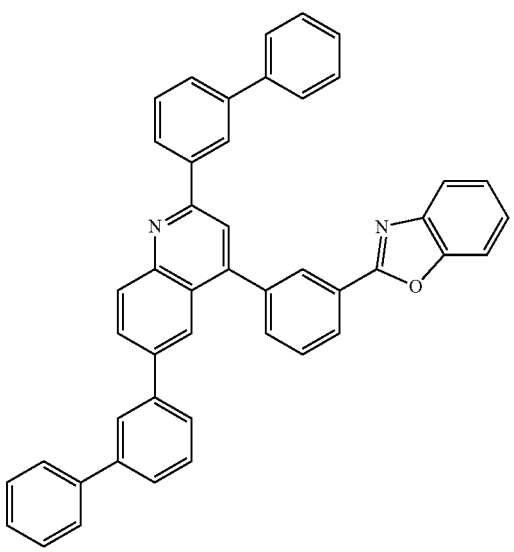
[A-148]
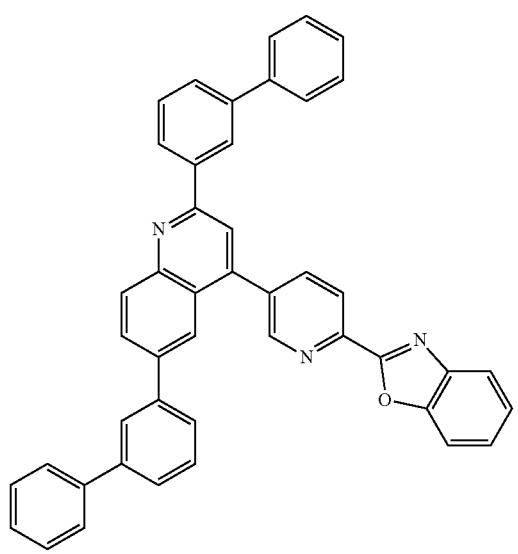
[A-150]
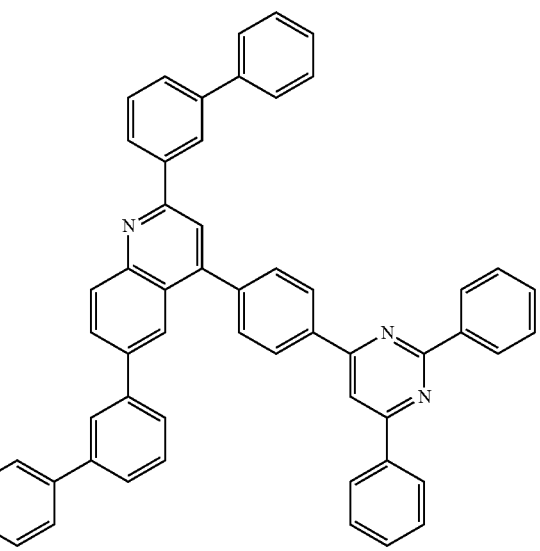

[A-151]
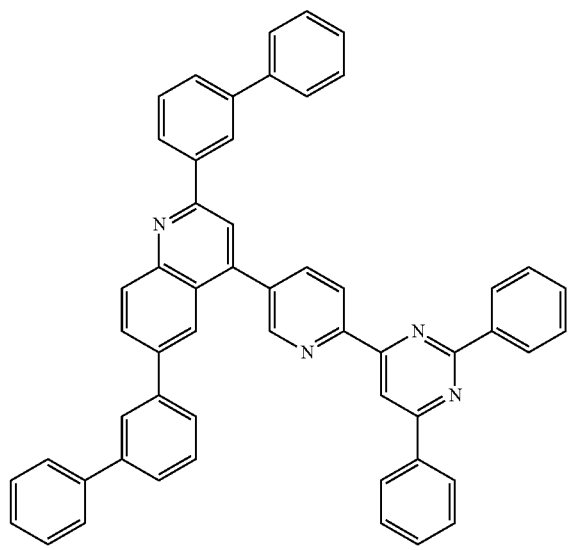
[A-153]
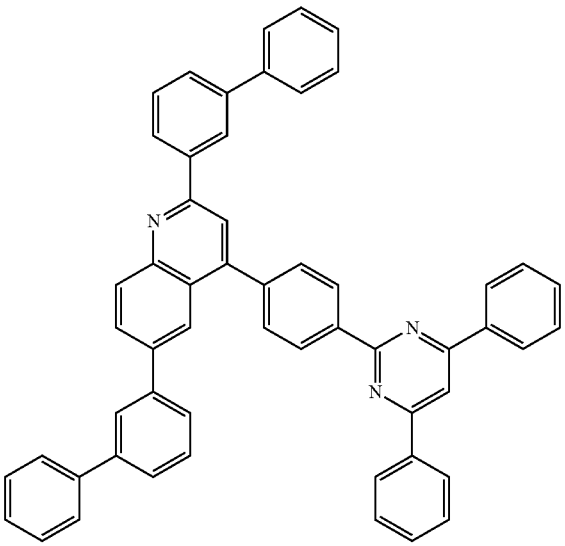
[A-152]
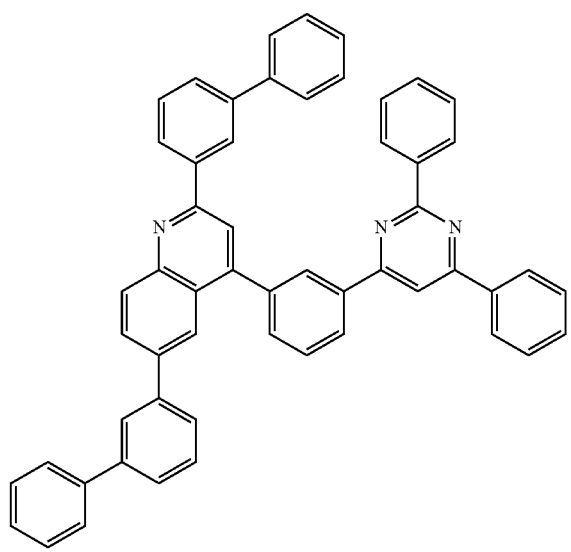
[A-154]
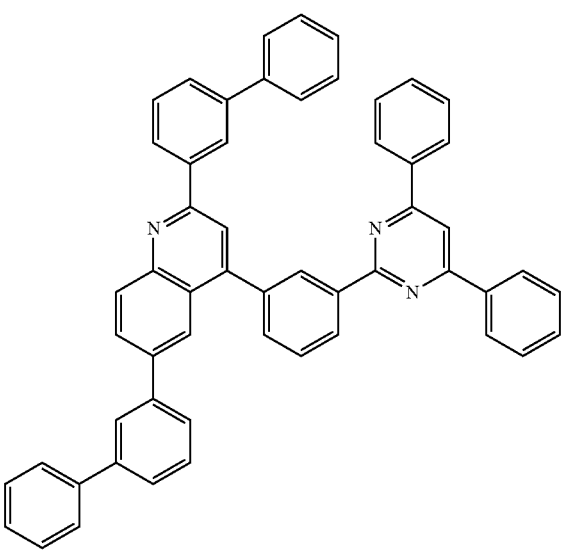

[A-155]
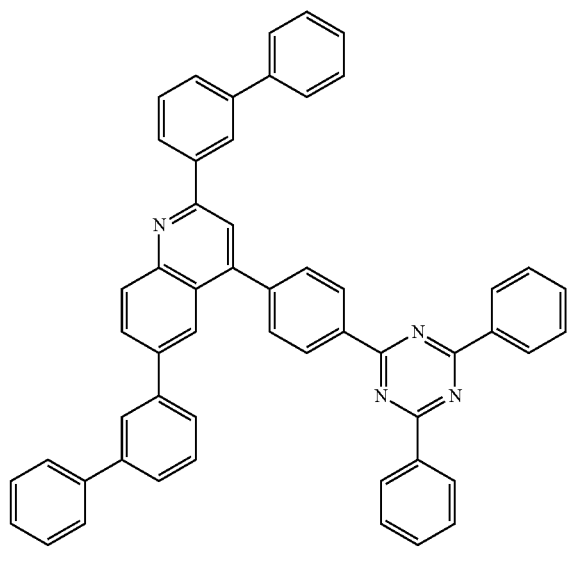
[A-157]
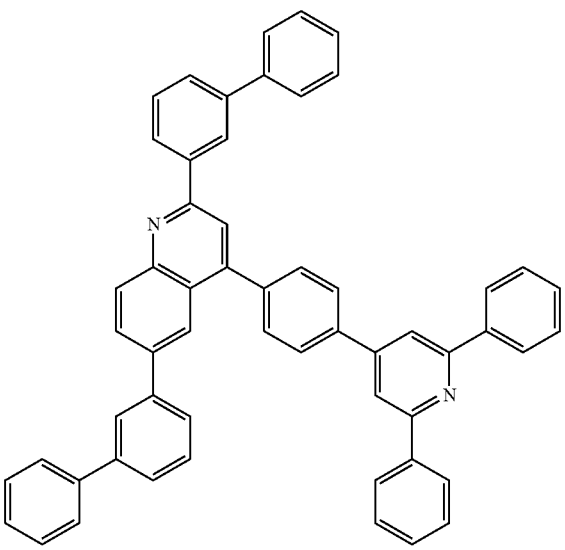
[A-156]
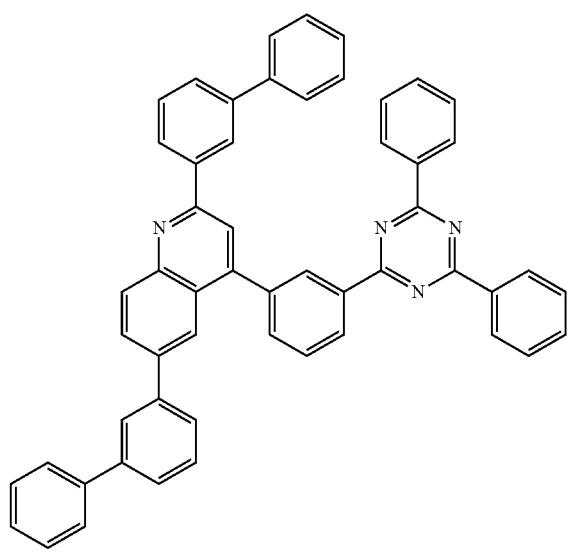
[A-158]
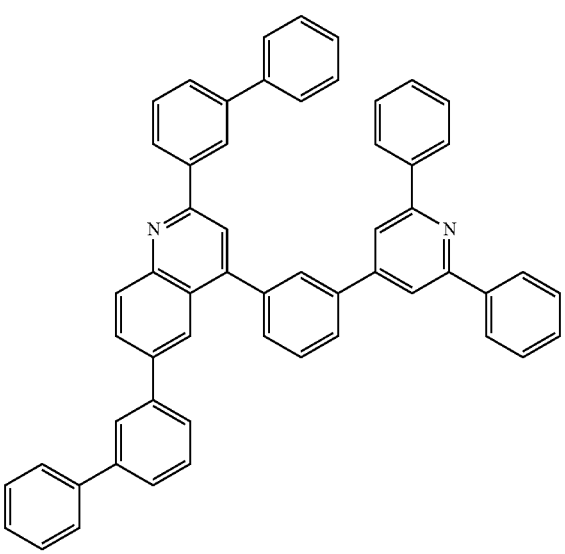

[A-159]
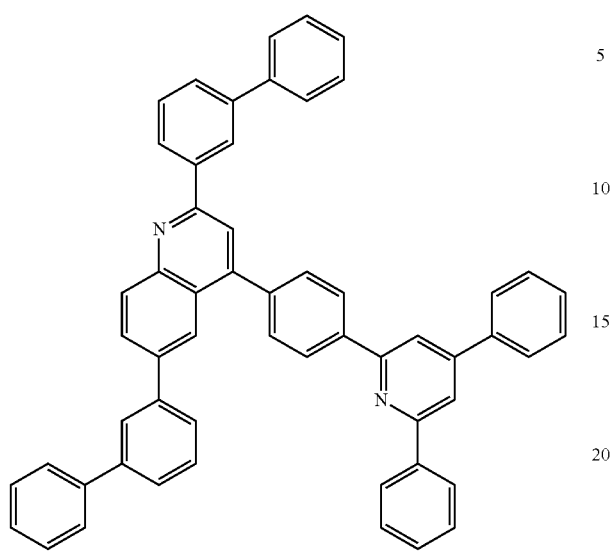
[A-160]
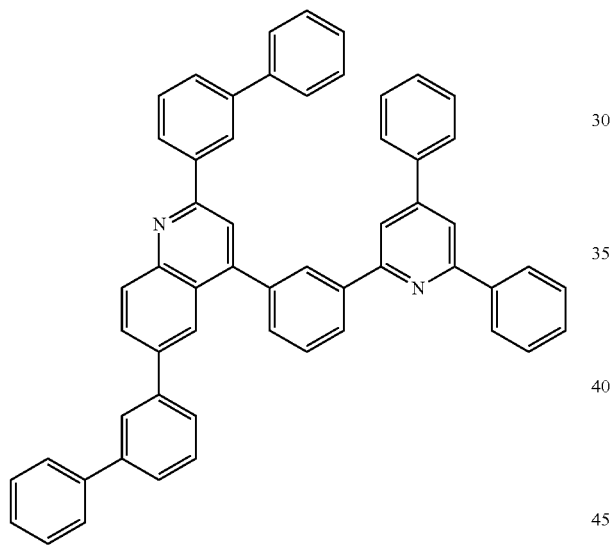
[A-161]
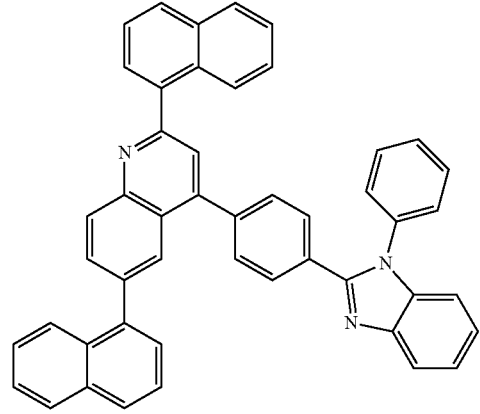
[A-162]
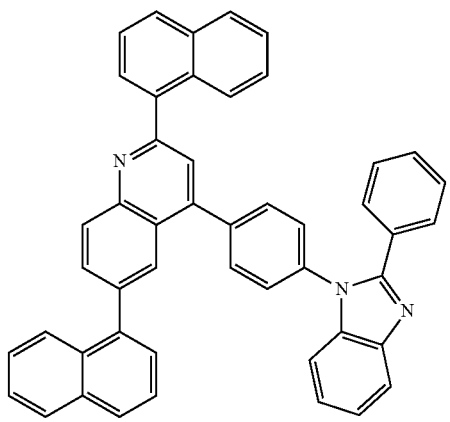
[A-163]
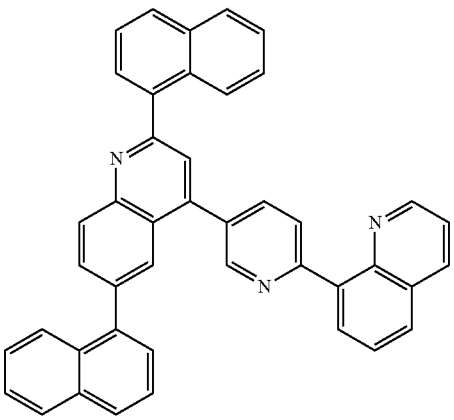
[A-164]
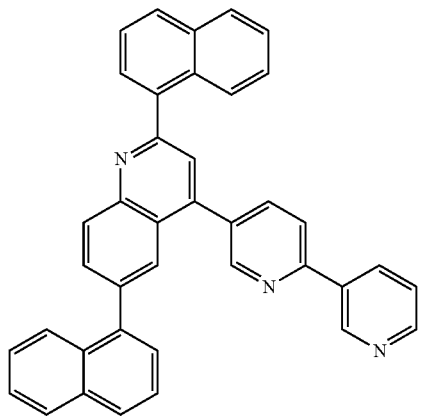

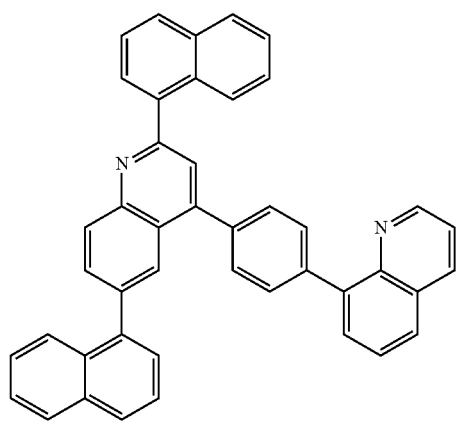
[A-165]
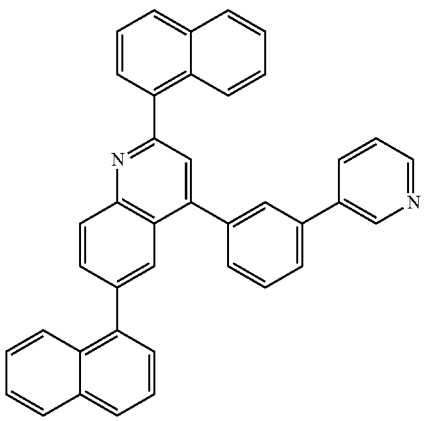
[A-168]
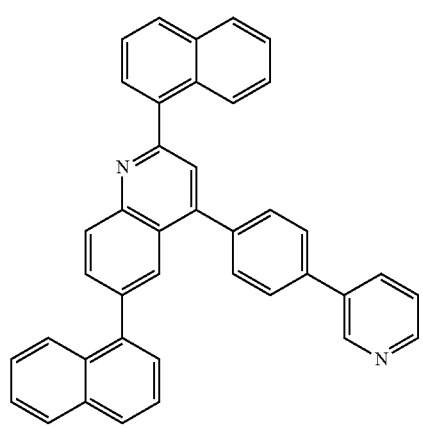
[A-166]
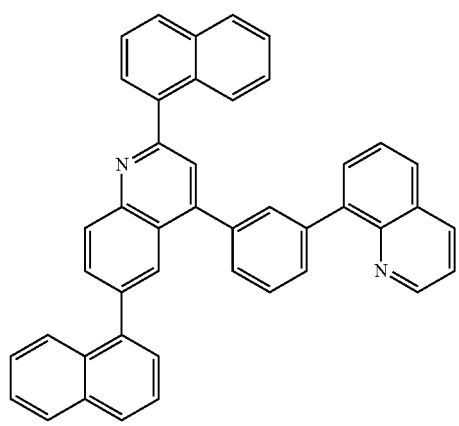
[A-167]
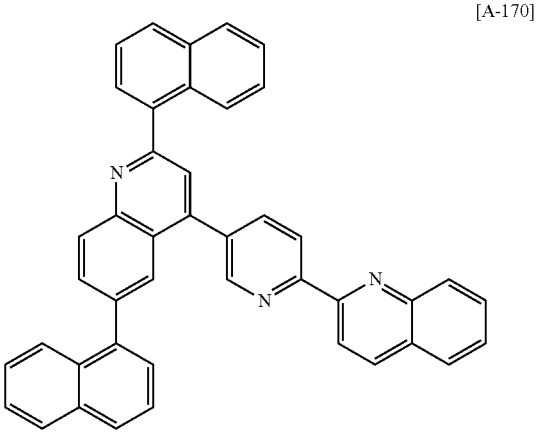
[A-170]

[A-171]
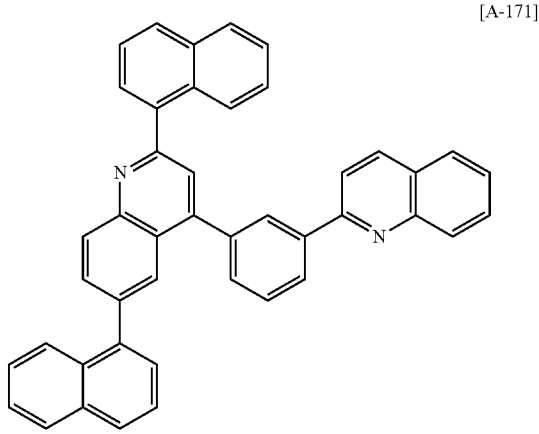
[A-174]
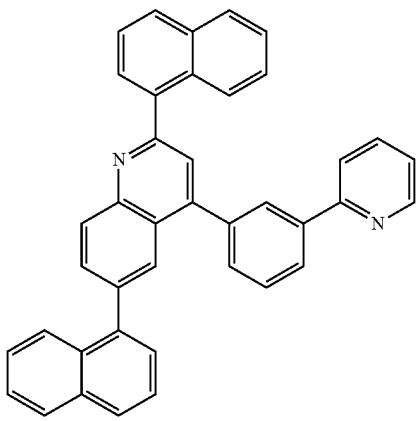
[A-172]
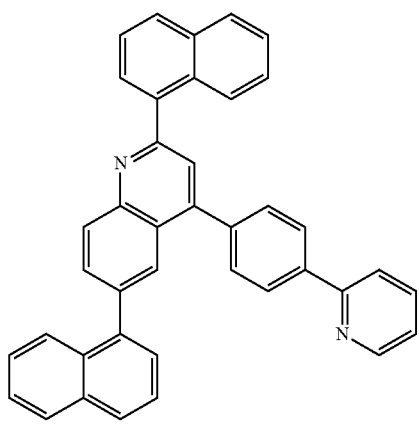
[A-175]
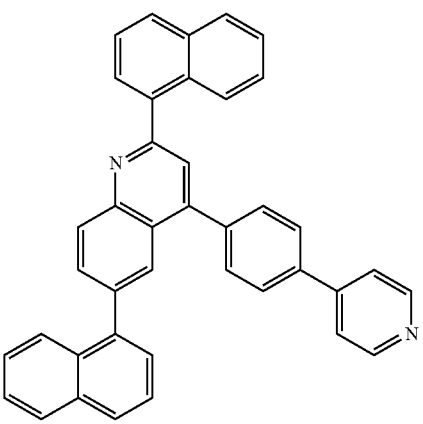
[A-173]
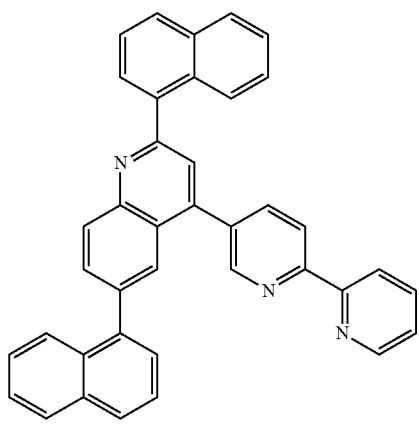
[A-176]
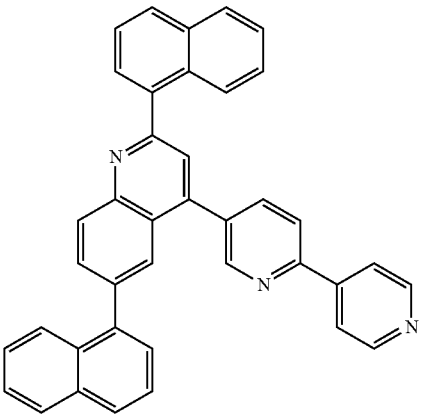

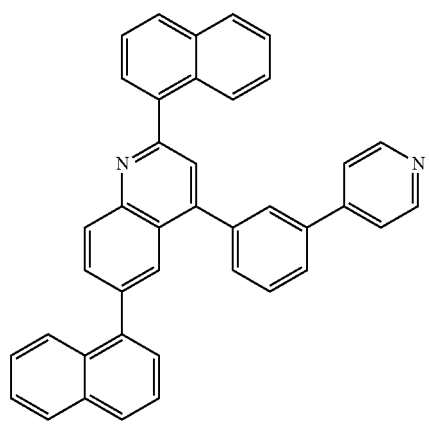
[A-177]
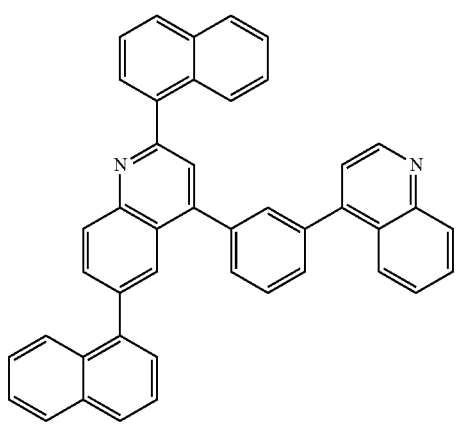
[A-180]
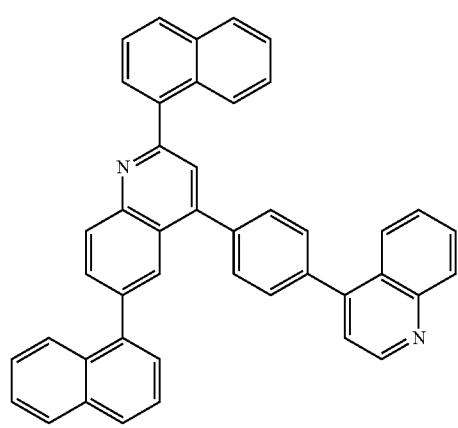
[A-178]
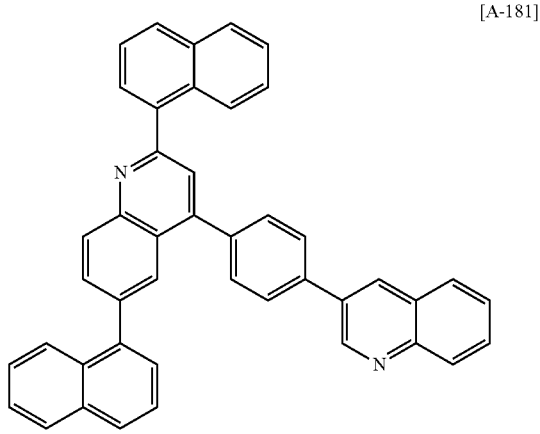
[A-181]
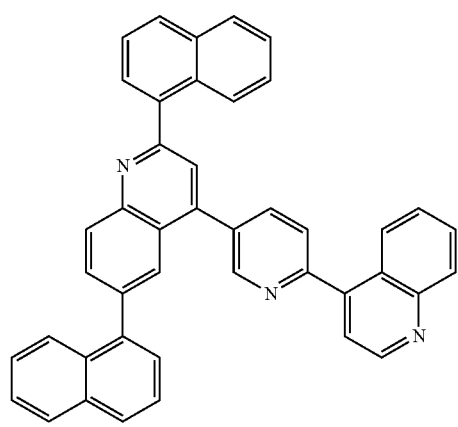
[A-179]
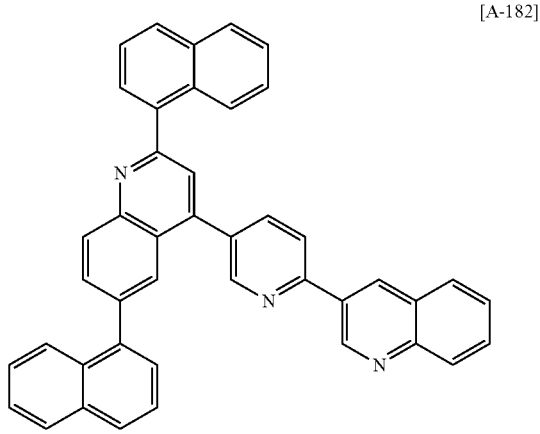
[A-182]

-continued
[A-183]
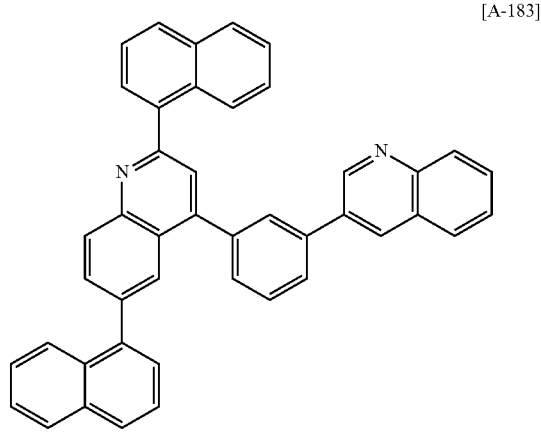
[A-186]
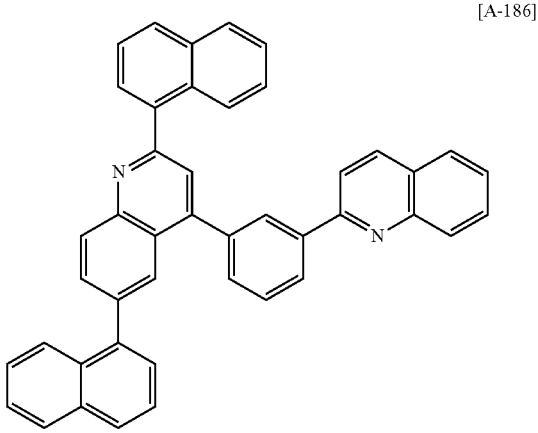
[A-184]
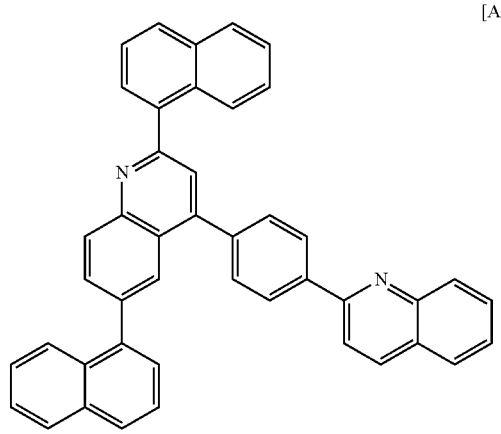
[A-187]
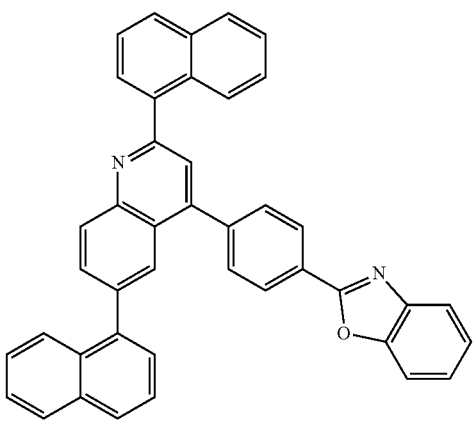
[A-185]
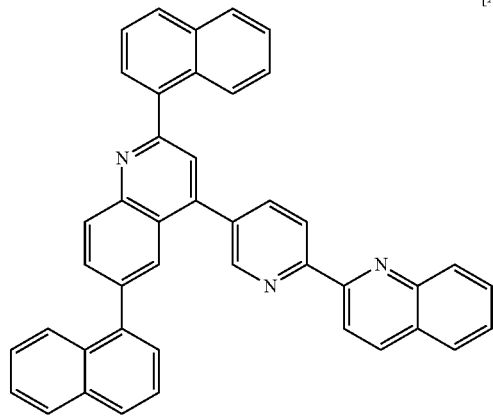
[A-188]
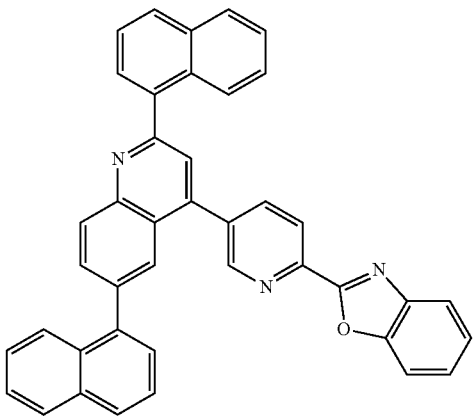

[A-189]
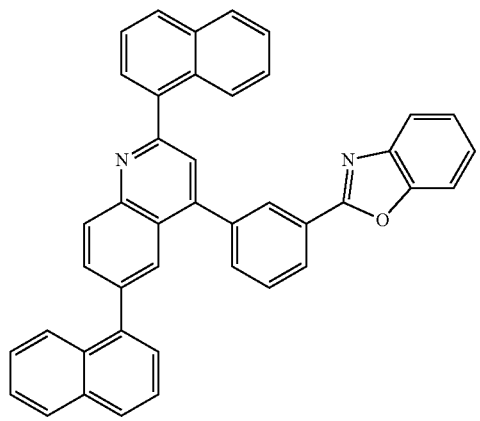
[A-192]
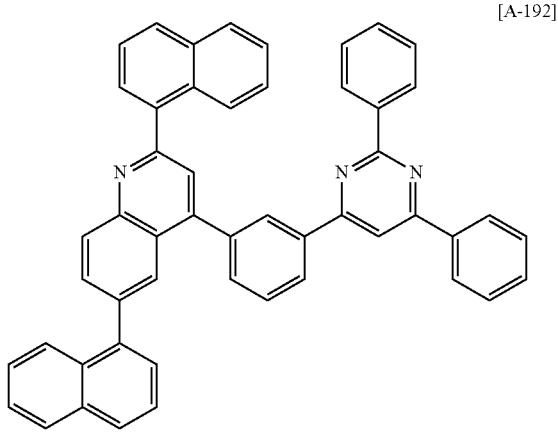
[A-190]
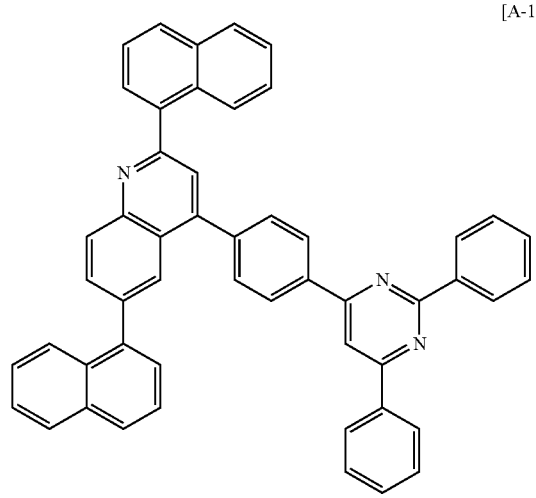
[A-193]
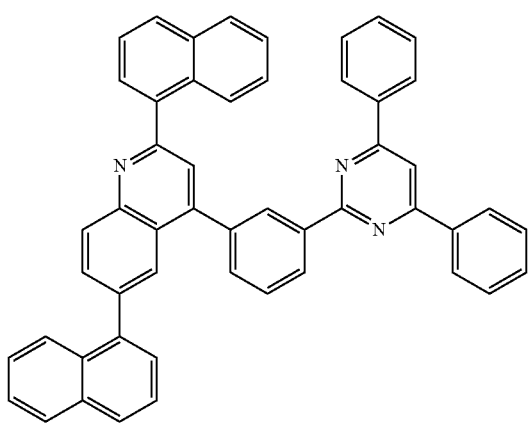
[A-191]
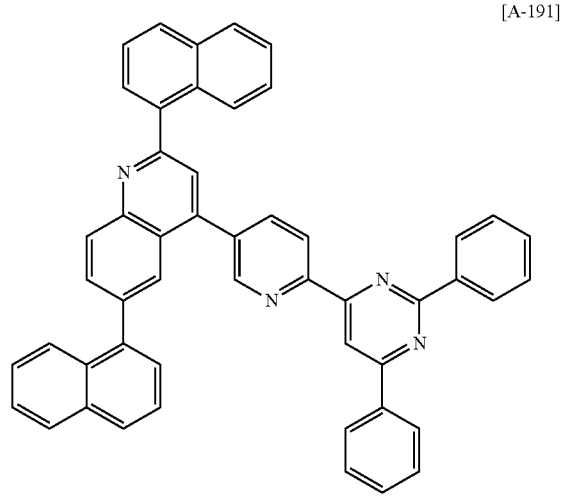
[A-194]

-continued
[A-195]
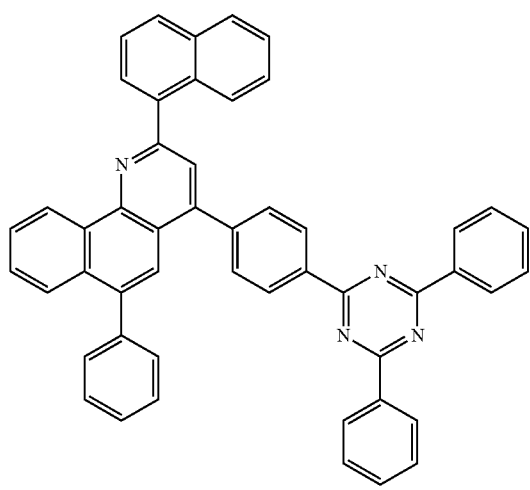
[A-196]
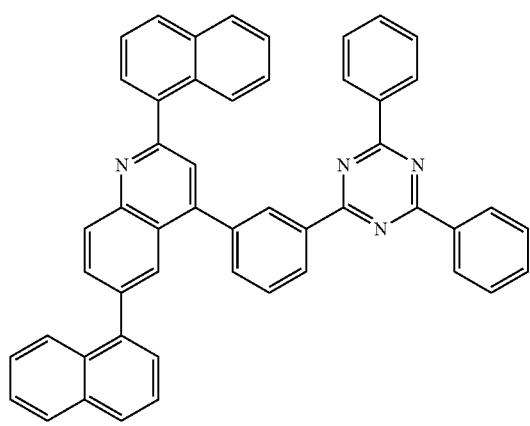
[A-197]
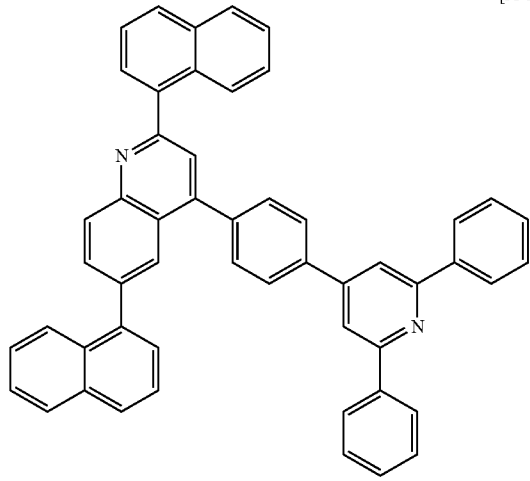
-continued
[A-198]
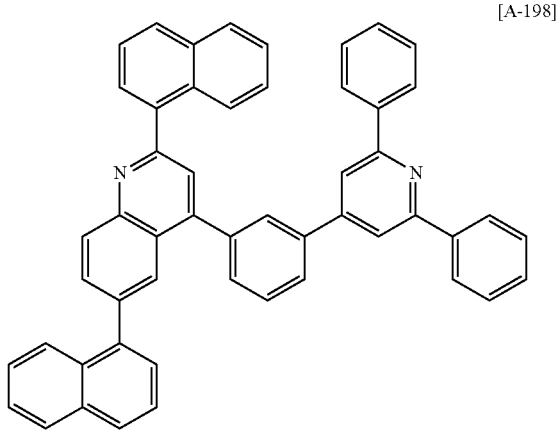
[A-199]
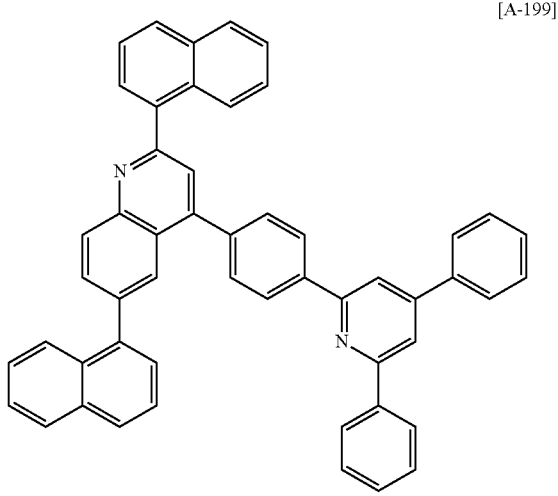
[A-200]
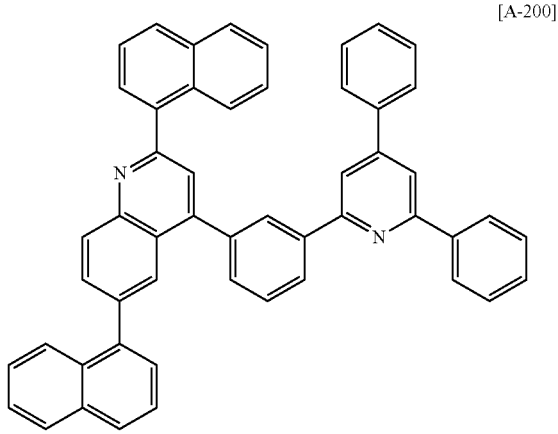 [SMILES: c1ccc(-c2cc(-c3ccccc3)nc(-c3cccc(-c4cc(-c5cccc6ccccc56)nc5ccc(-c6cccc7ccccc67)cc45)c3)c2)cc1]

[A-201]
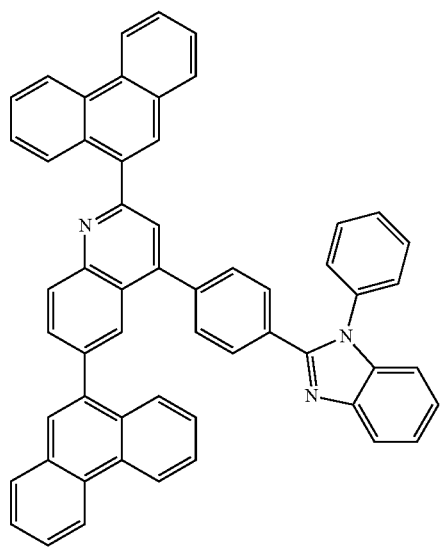
[A-204]
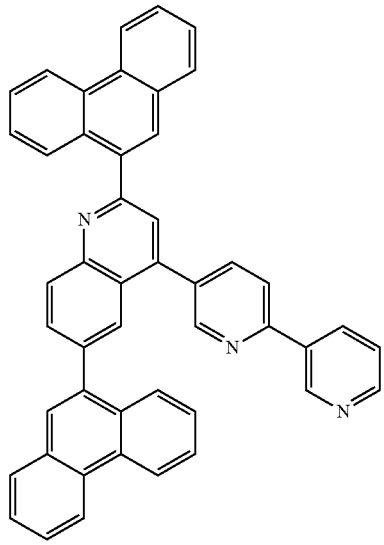
[A-202]
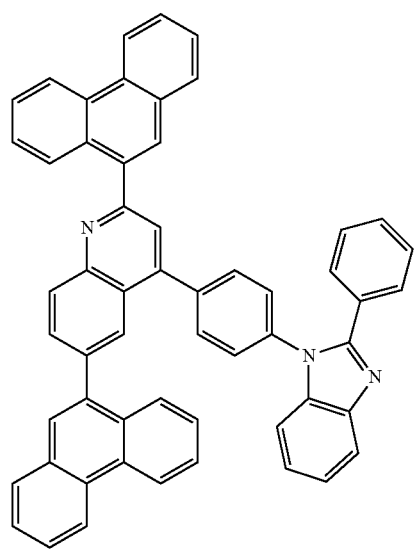
[A-205]
[A-203]
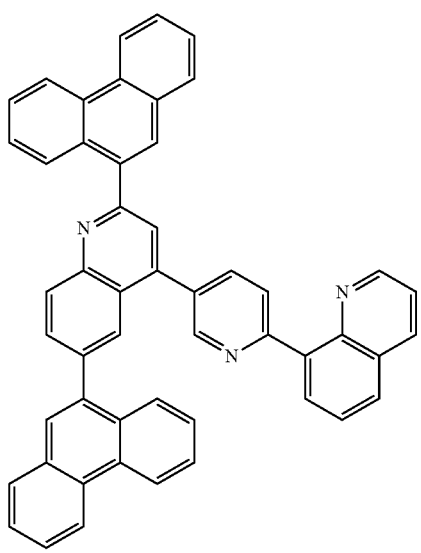
[A-206]
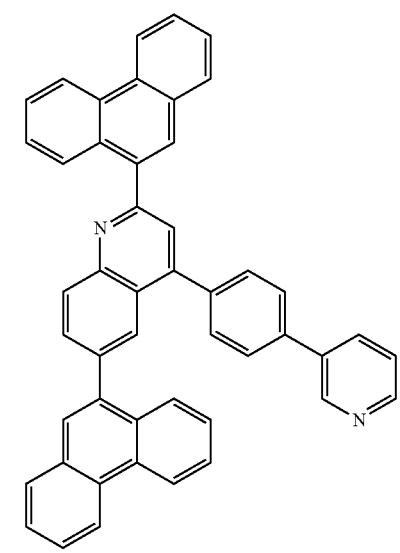

[A-207]
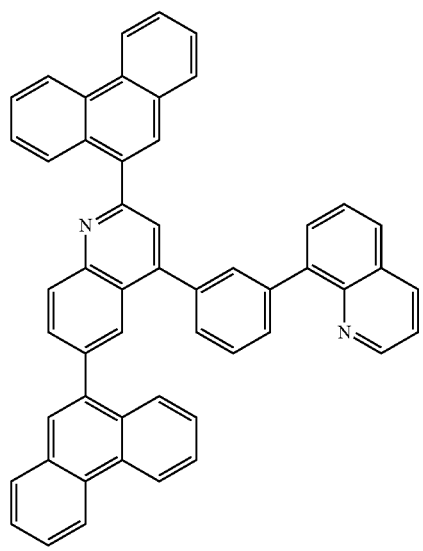
[A-208]
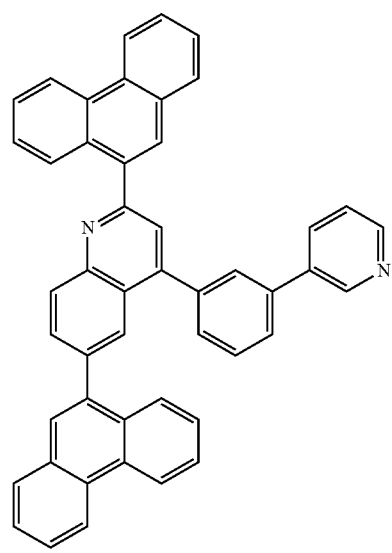
[A-209]
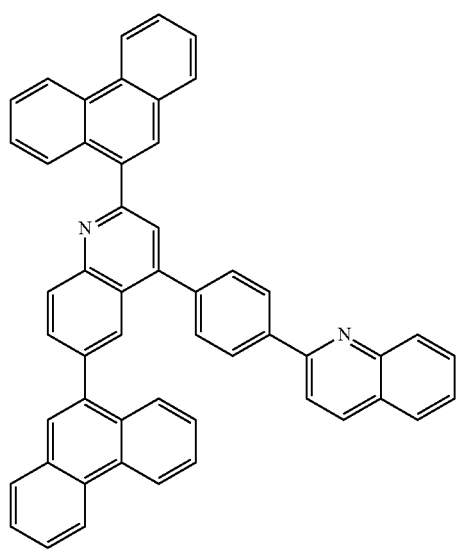
[A-210]
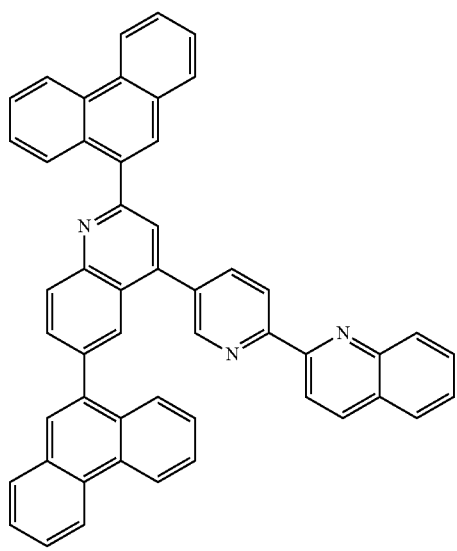
[A-211]
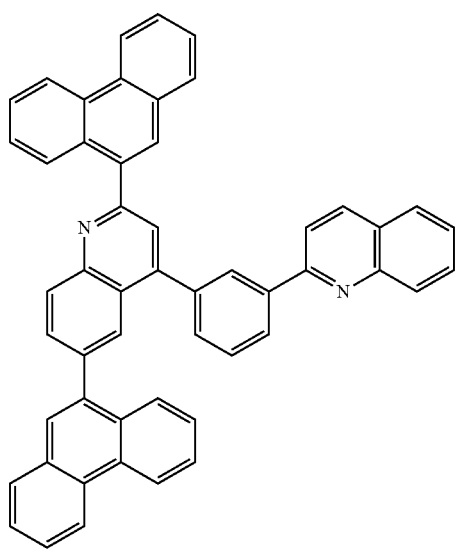
[A-212]
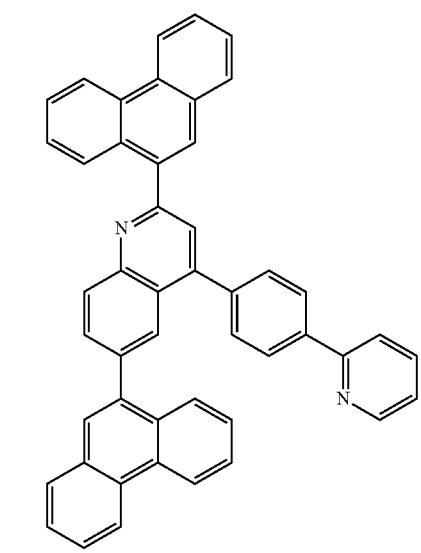

[A-213]
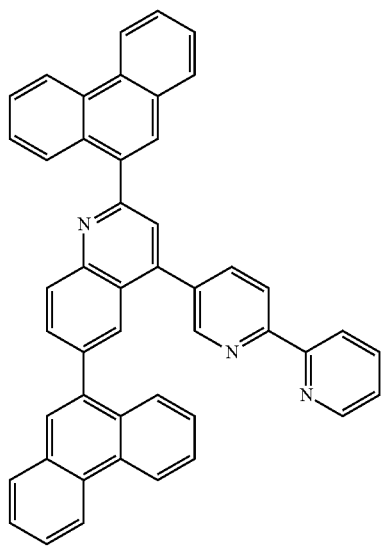
[A-216]
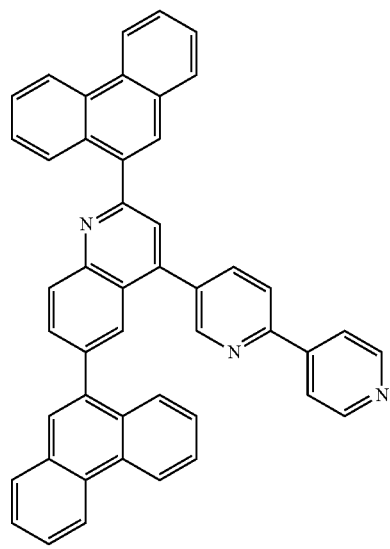
[A-214]
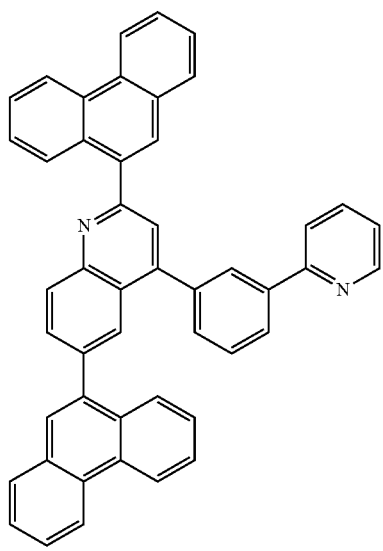
[A-217]
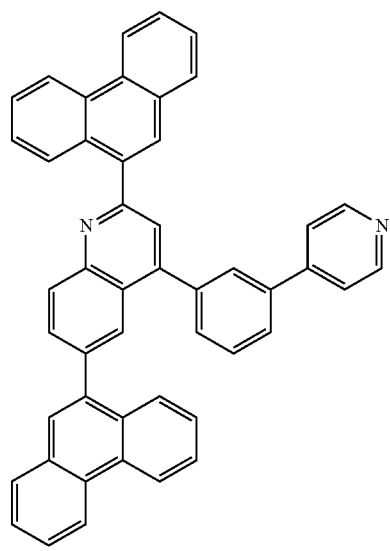
[A-215]
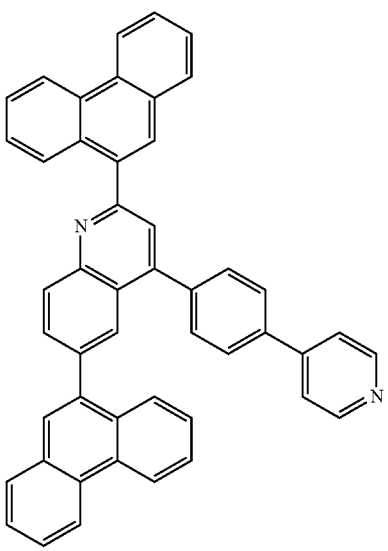
[A-218]
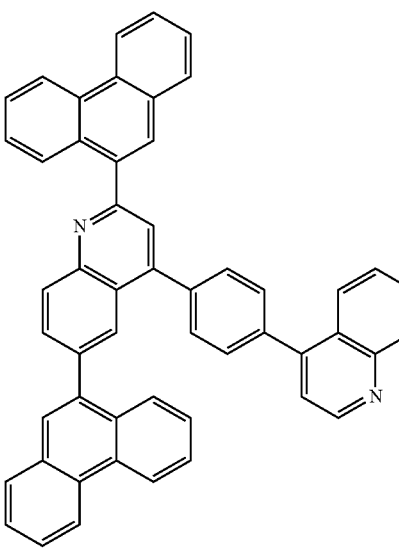

[A-219]
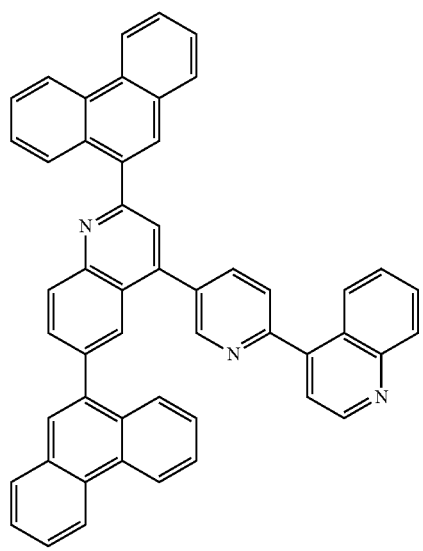
[A-222]
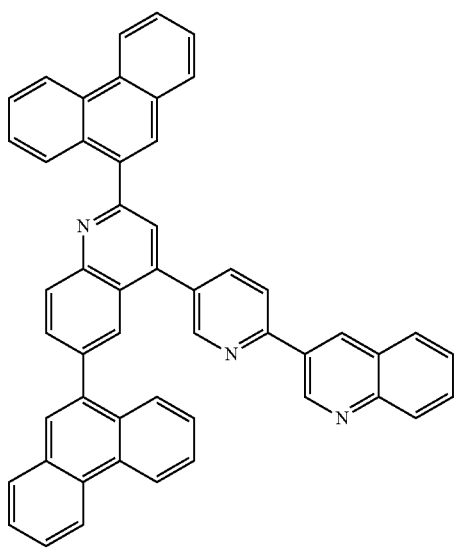
[A-220]
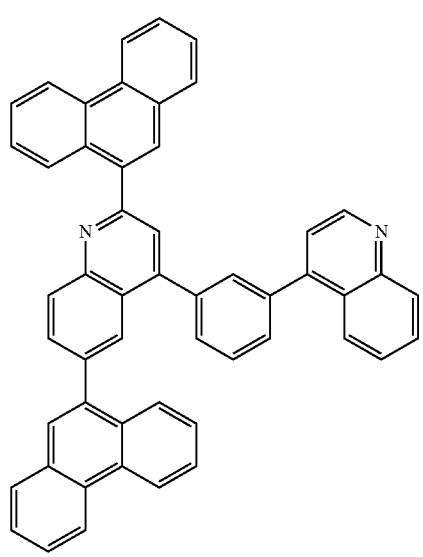
[A-223]
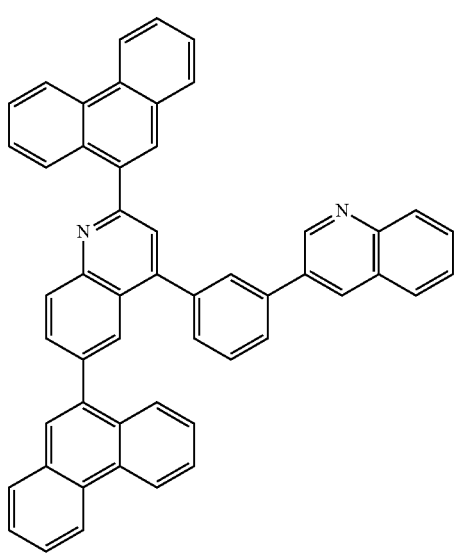
[A-221]
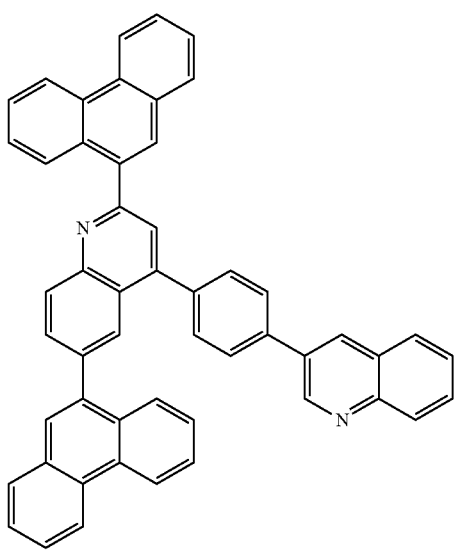
[A-224]
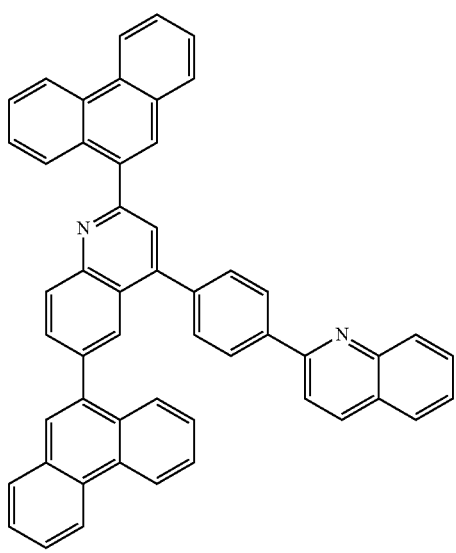

[A-225]
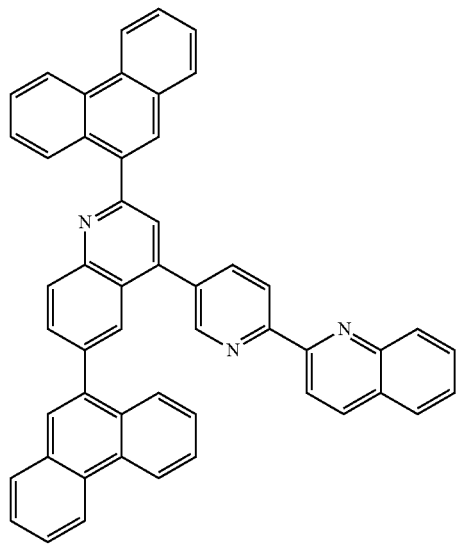
[A-228]
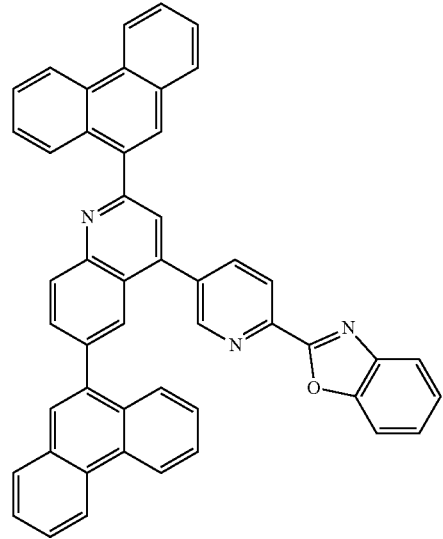
[A-226]
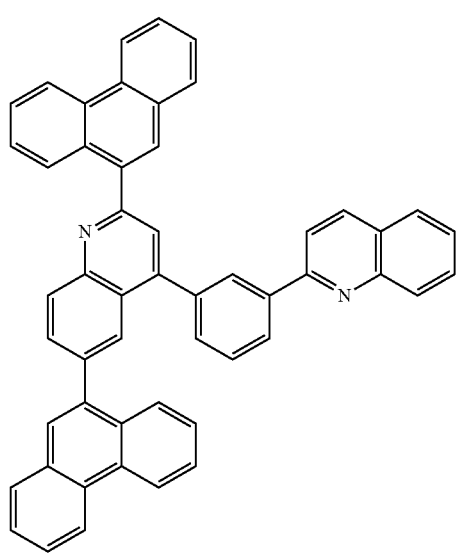
[A-229]
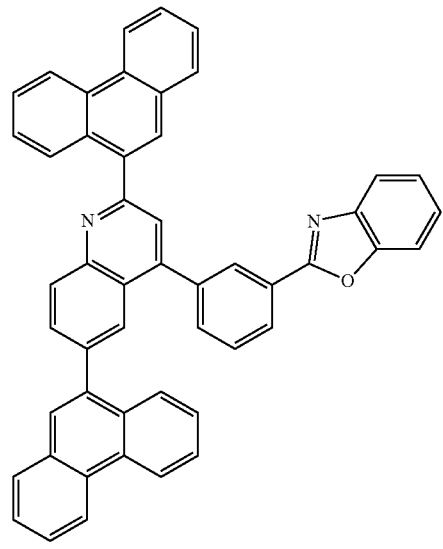
[A-227]
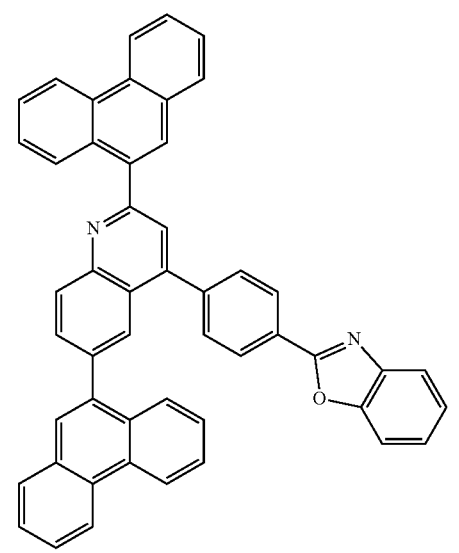
[A-230]
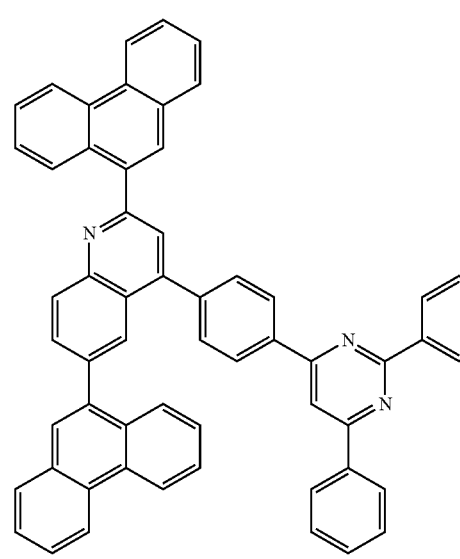

[A-231]
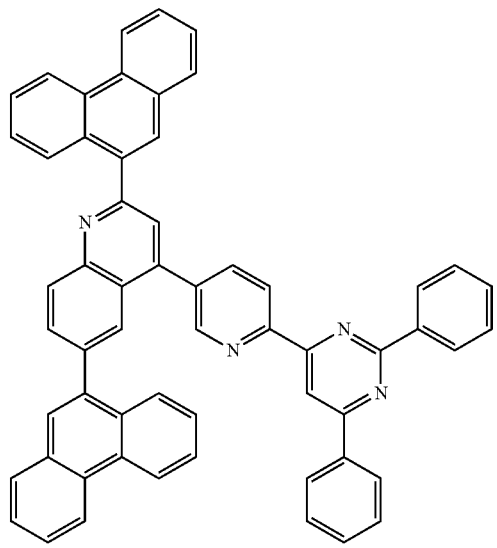
[A-233]
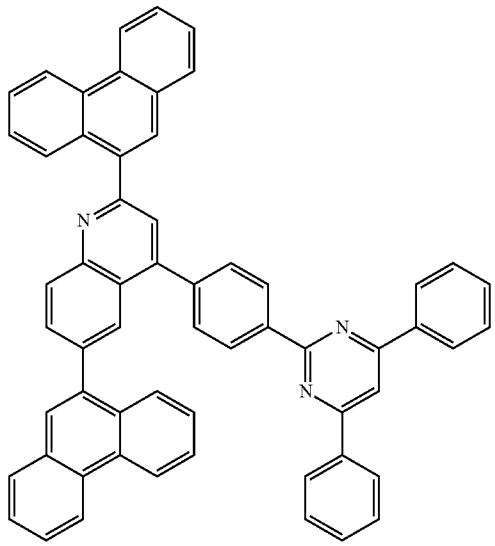
[A-232]
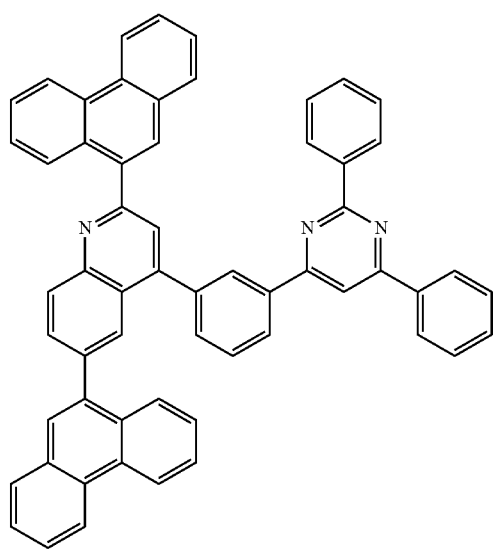
[A-234]
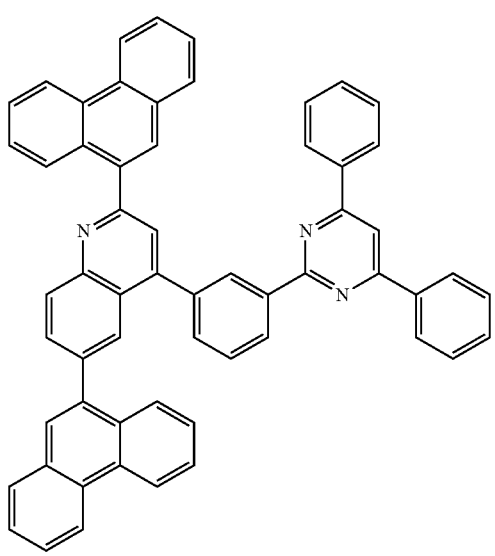

[A-235]
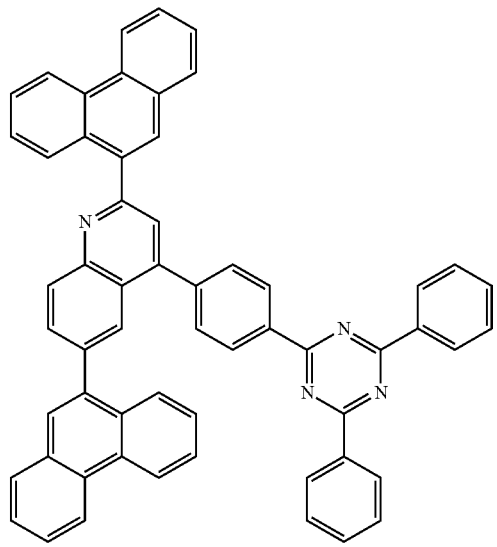
[A-237]
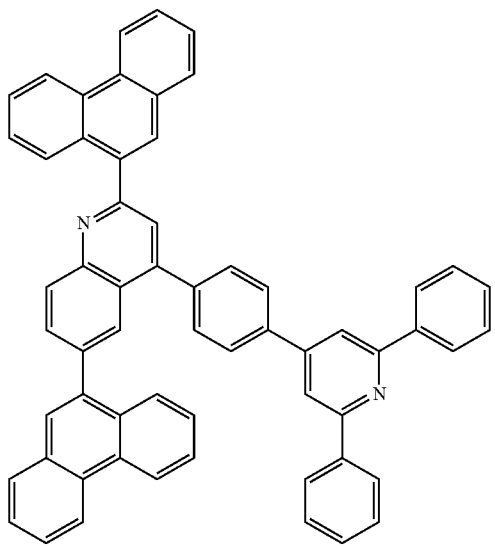
[A-236]
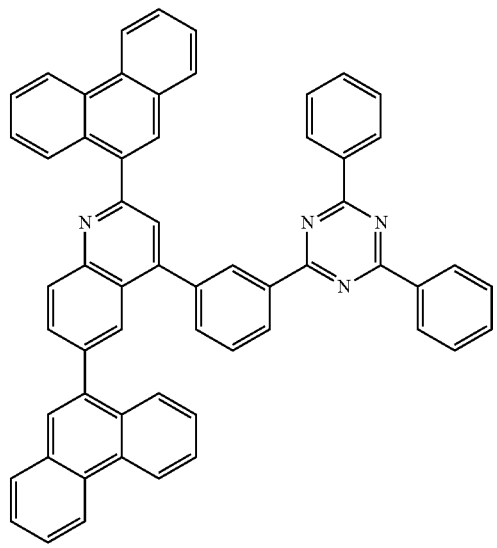
[A-238]
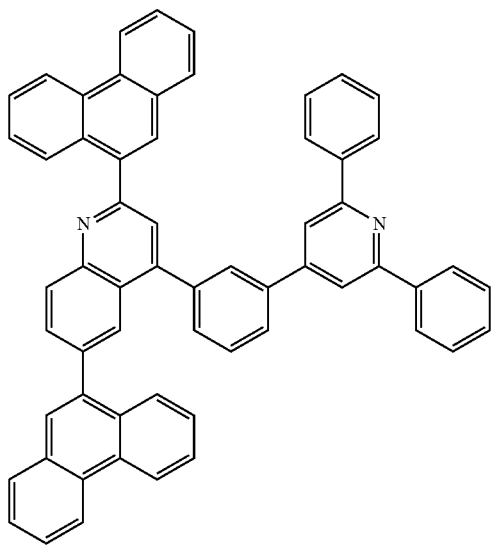

[A-239]
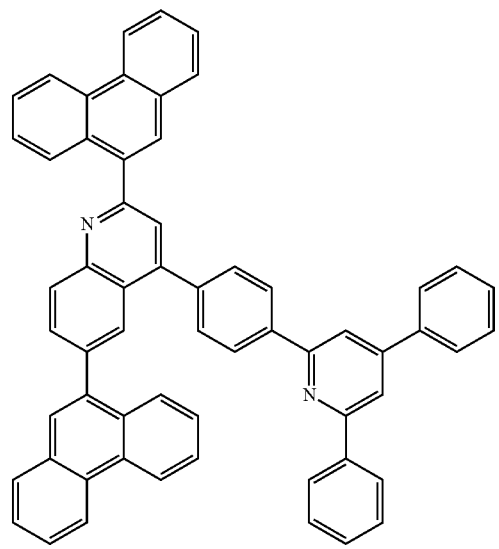
[A-240]
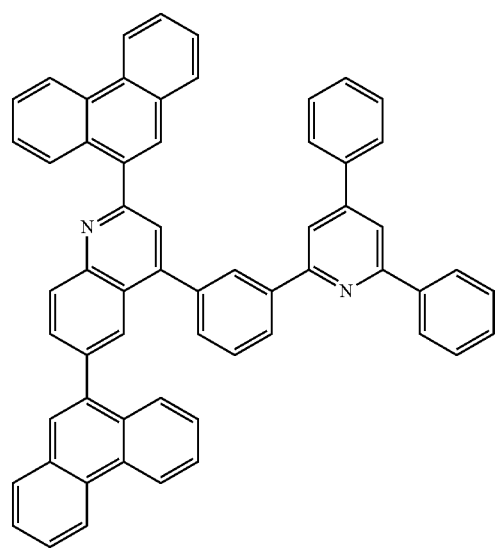
[A-241]
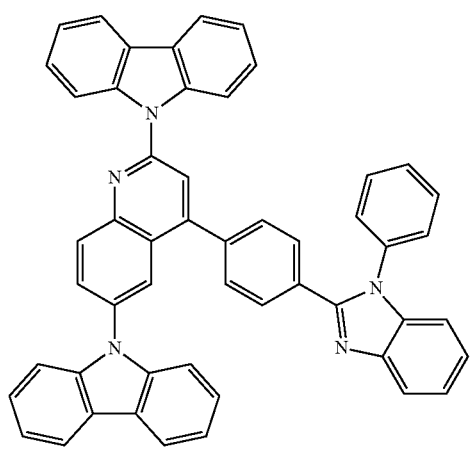
[A-242]
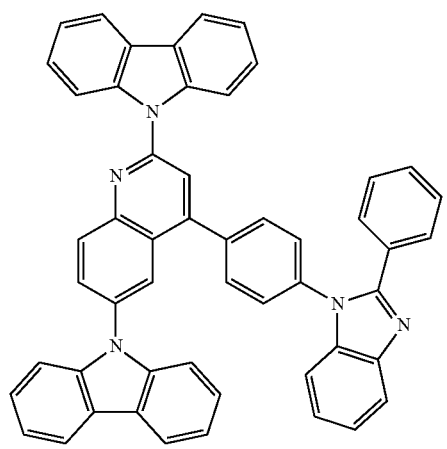
[A-243]
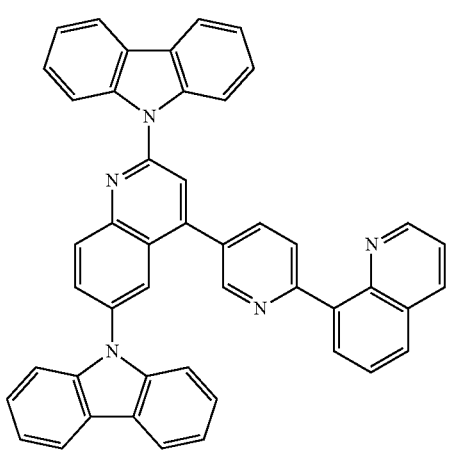
[A-244]
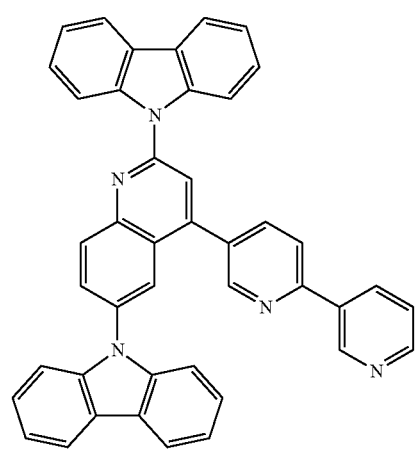

[A-245]
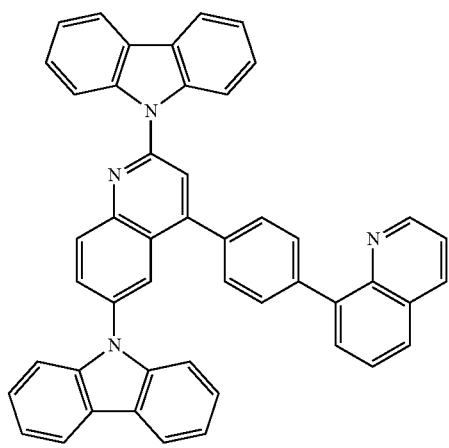
[A-248]
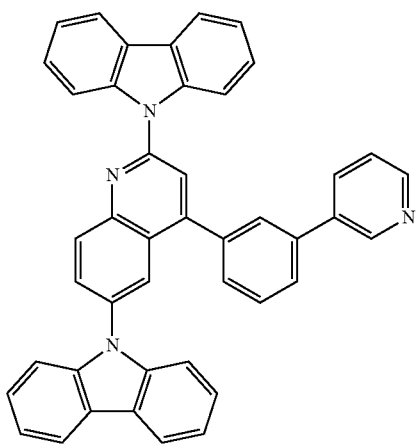
[A-246]
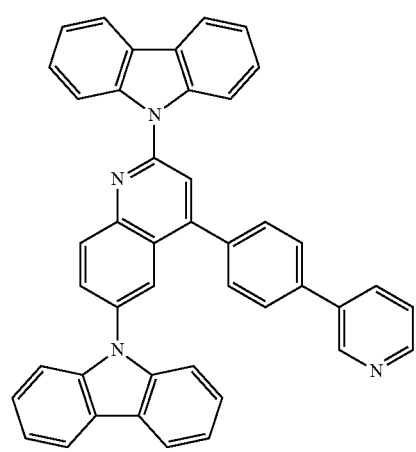
[A-249]
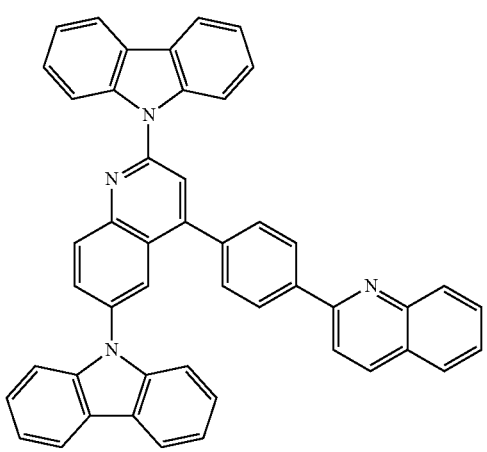
[A-247]
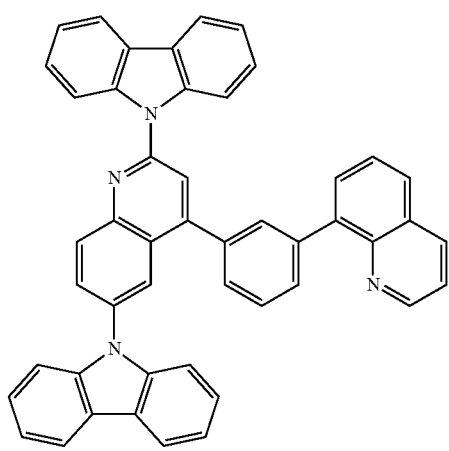
[A-250]
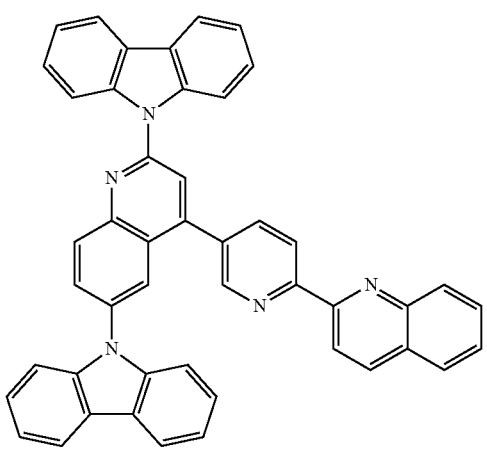

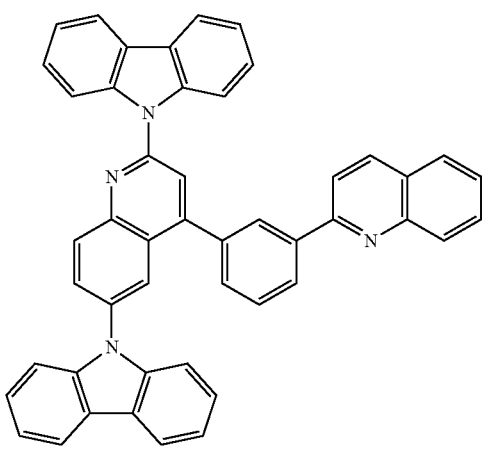
[A-251]
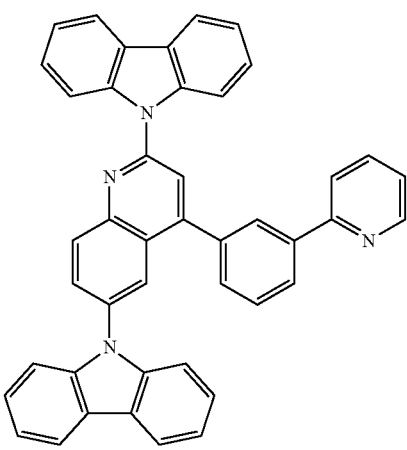
[A-254]
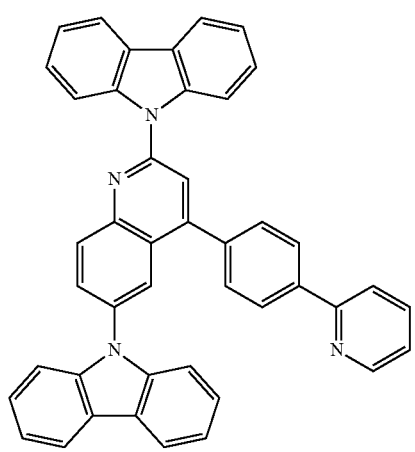
[A-252]
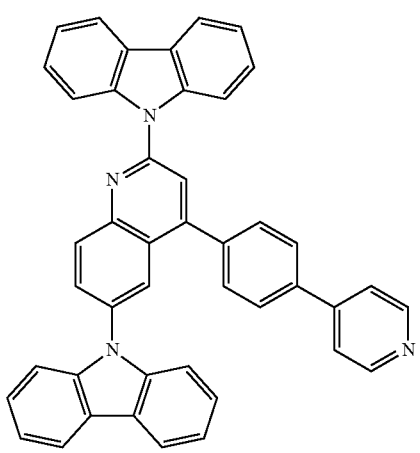
[A-255]
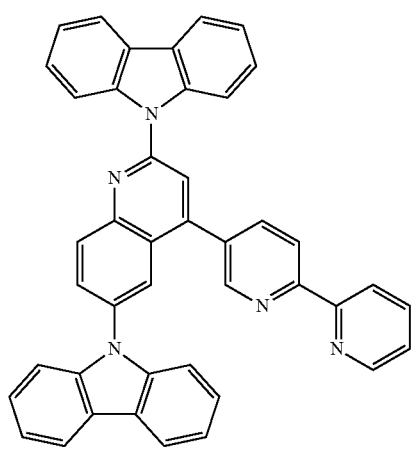
[A-253]
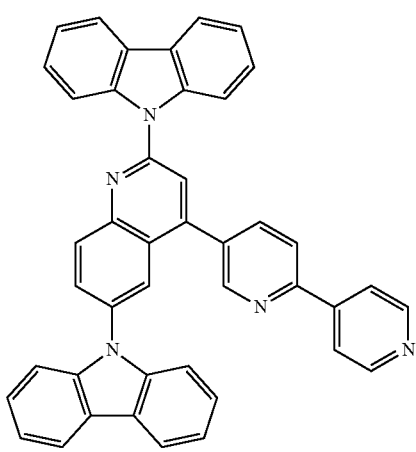
[A-256]

[A-257]
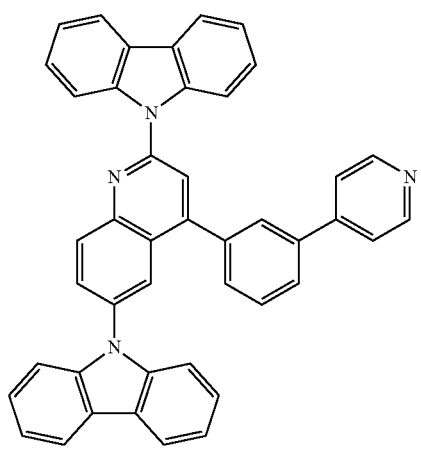
[A-258]
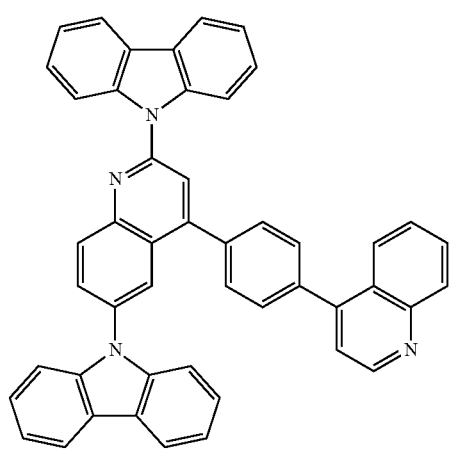
[A-259]
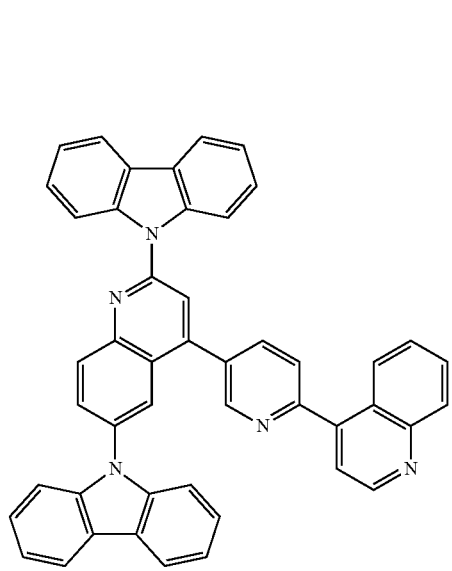
[A-260]
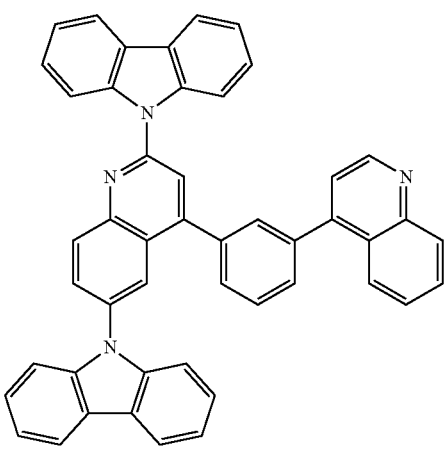
[A-261]
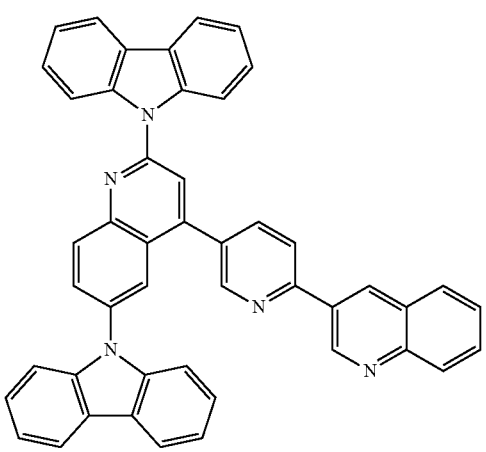
[A-262]

[A-263]
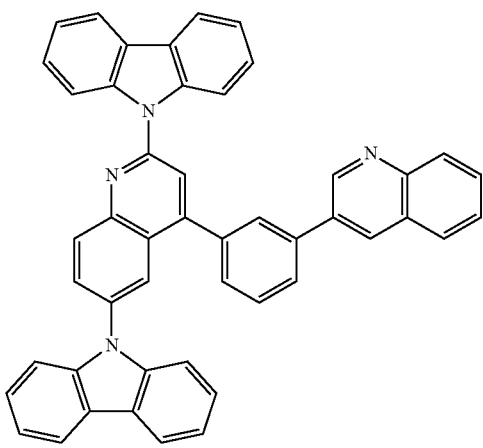
[A-266]
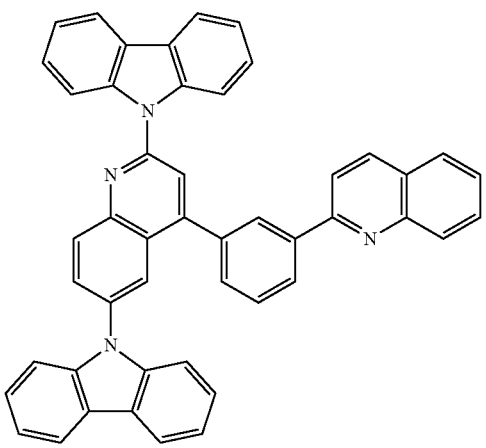
[A-264]
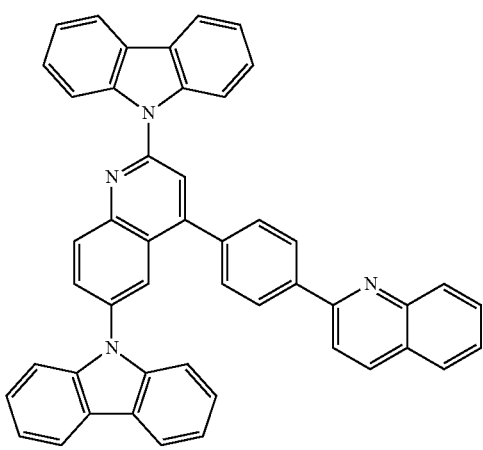
[A-267]
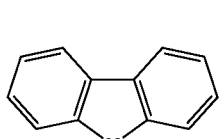
[A-265]
[A-268]
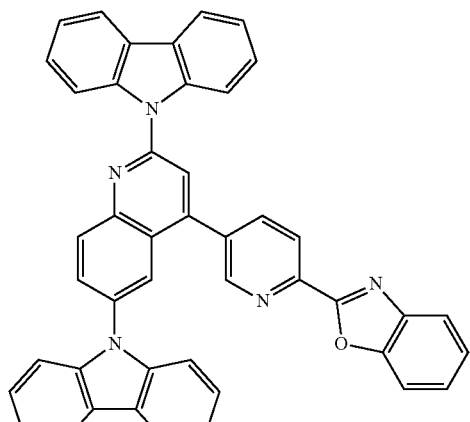
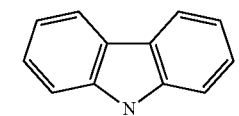

[A-269]
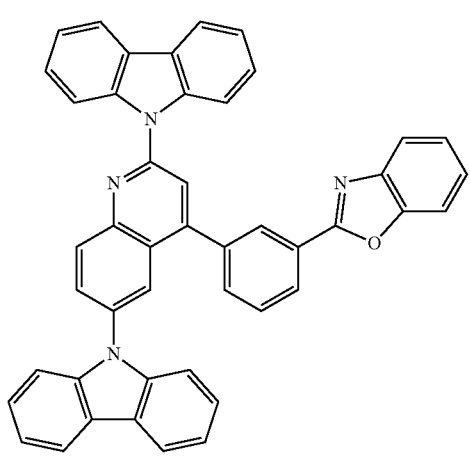
[A-272]
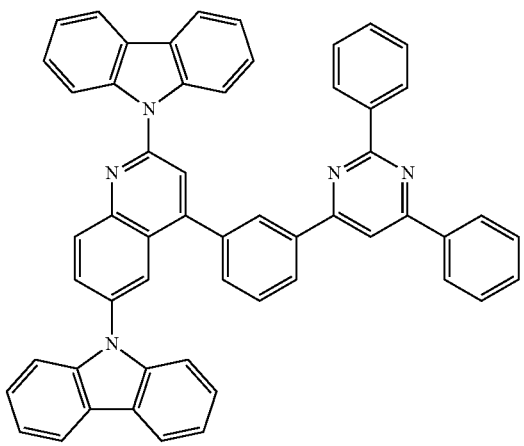
[A-270]
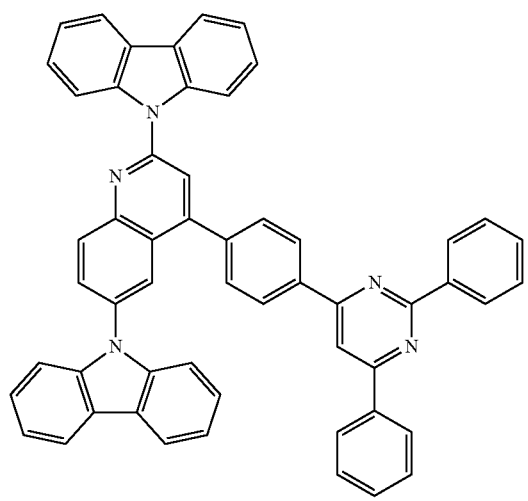
[A-273]
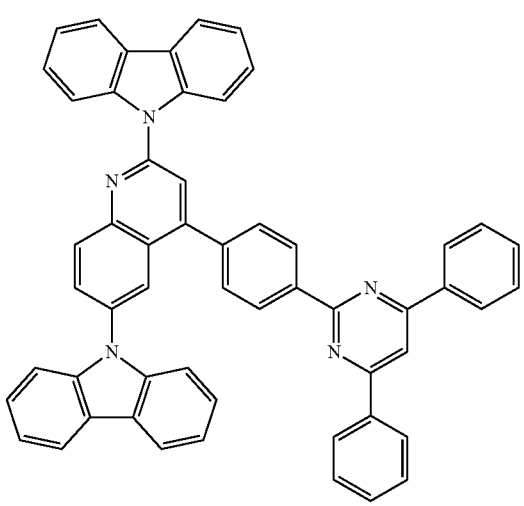
[A-271]
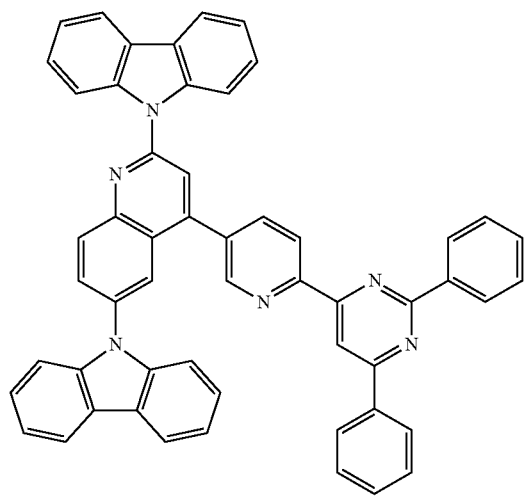
[A-274]
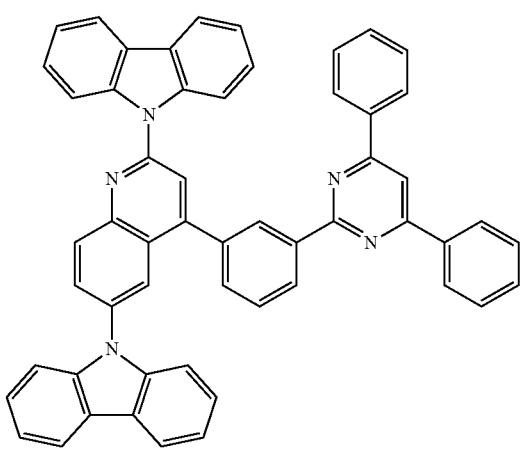

-continued
[A-275]
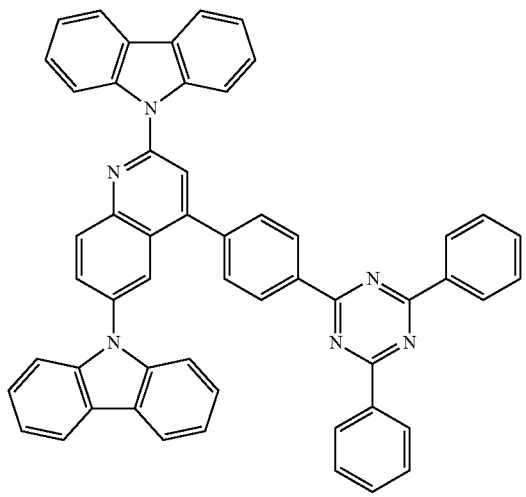
[A-276]
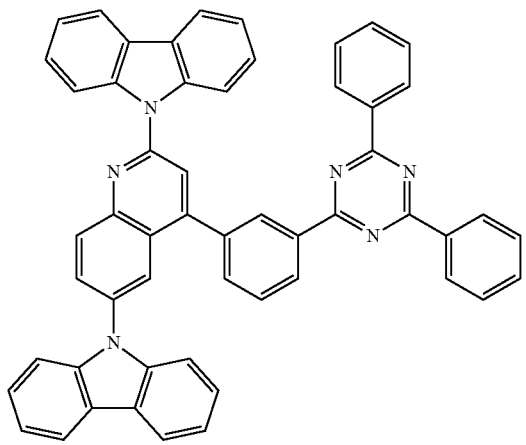
[A-277]
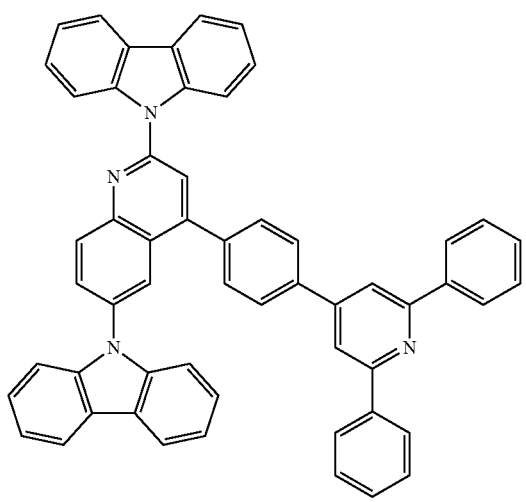
-continued
[A-278]
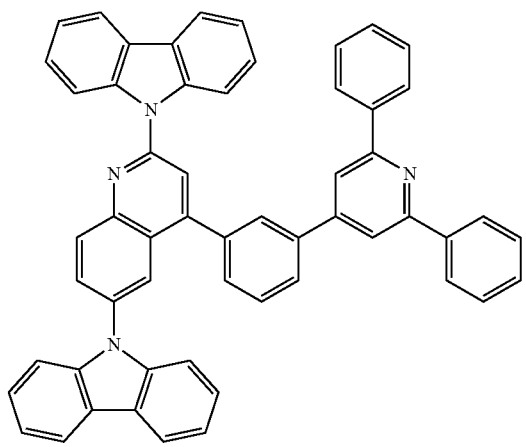
[A-279]
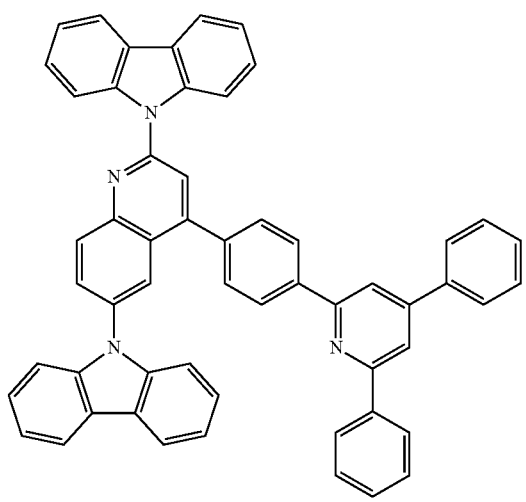
[A-280]
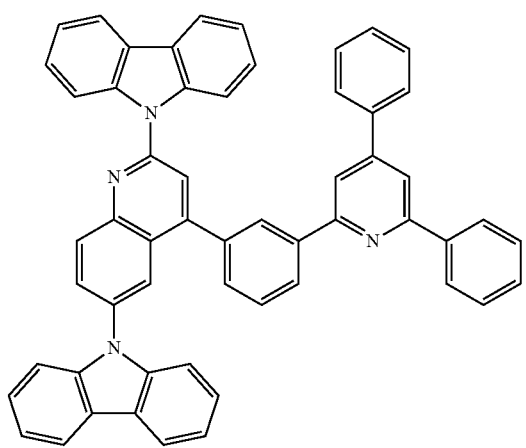

[A-281]
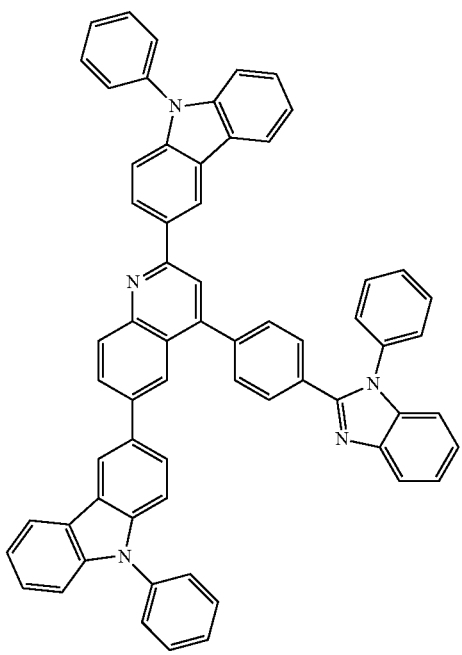
[A-283]
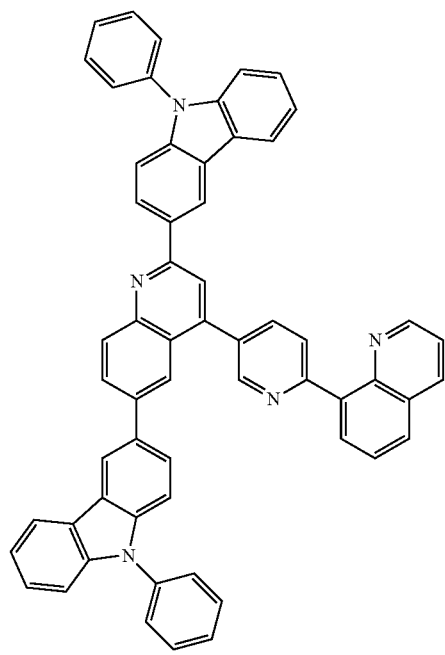
[A-282]
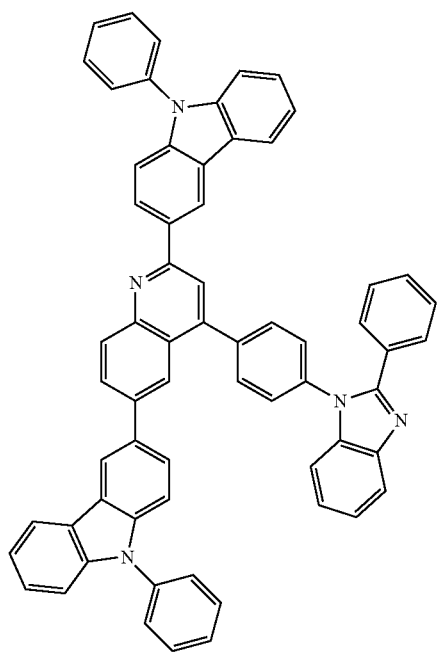
[A-284]
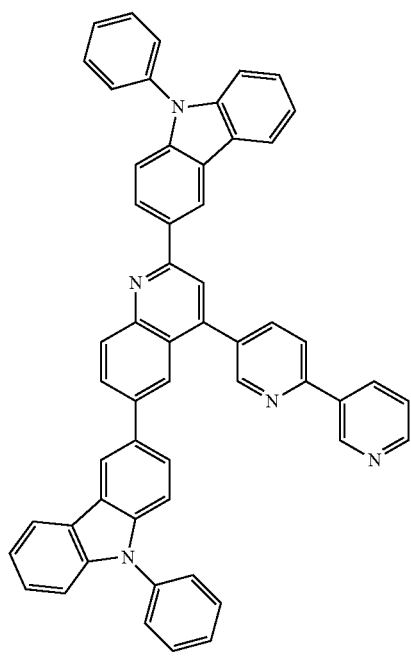

[A-285]
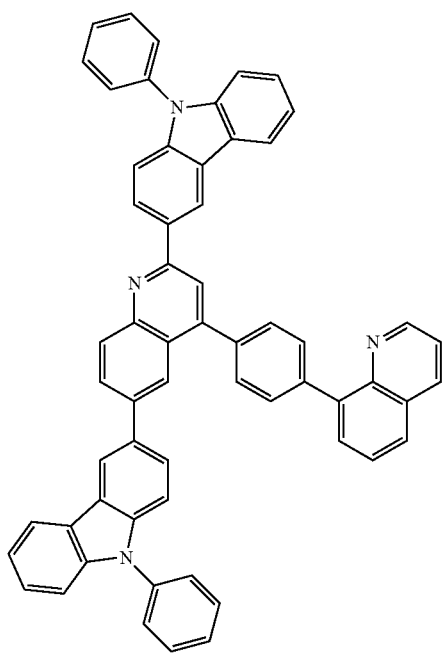
[A-287]
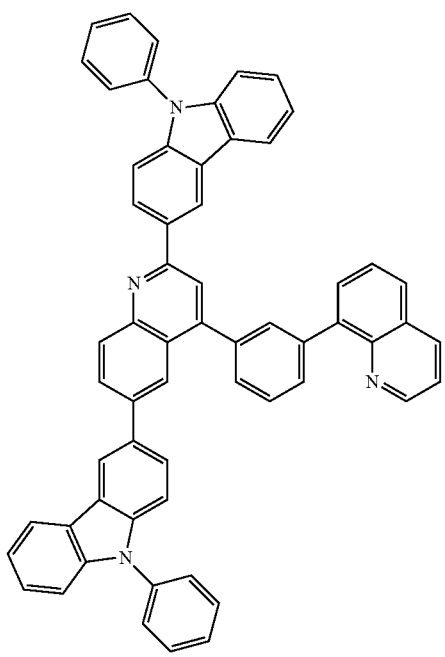
[A-286]
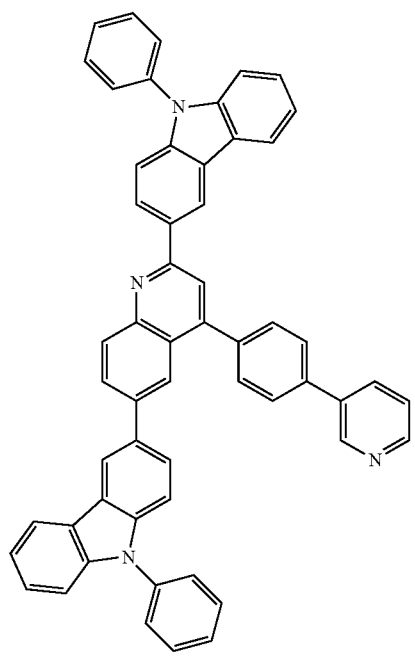
[A-288]
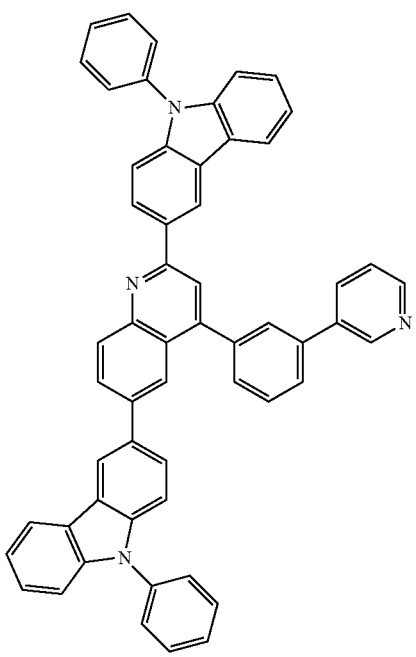

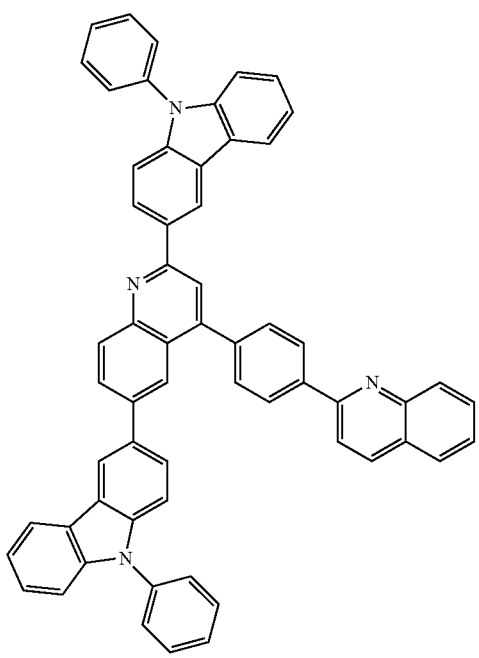
[A-289]
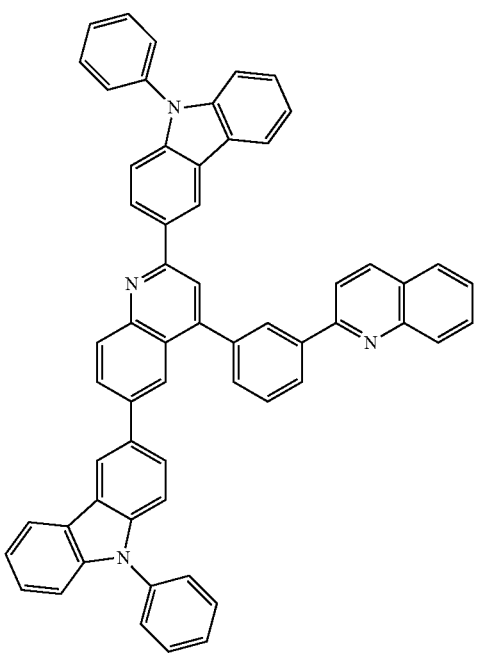
[A-291]
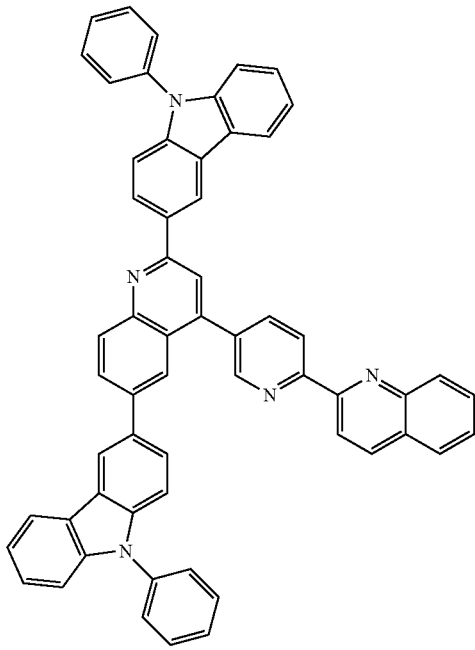
[A-290]
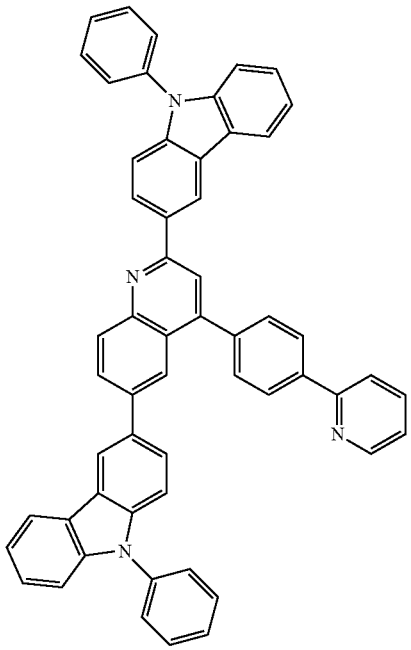
[A-292]

121
-continued
[A-293]
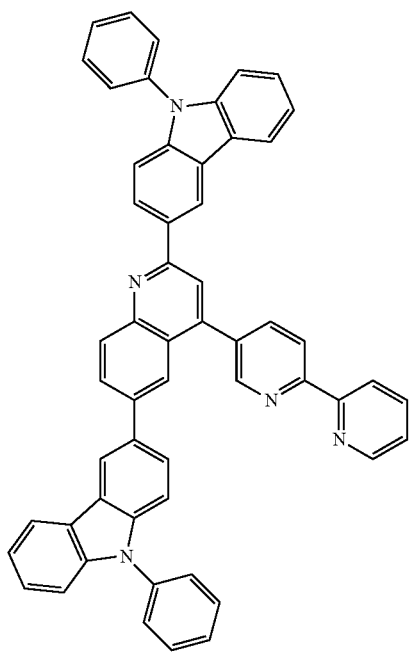
122
-continued
[A-295]
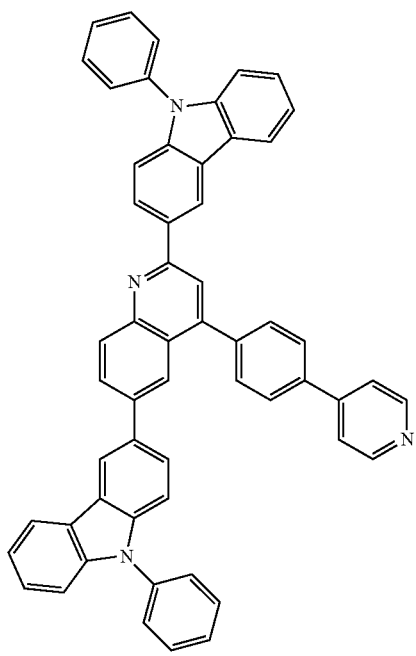
[A-294]
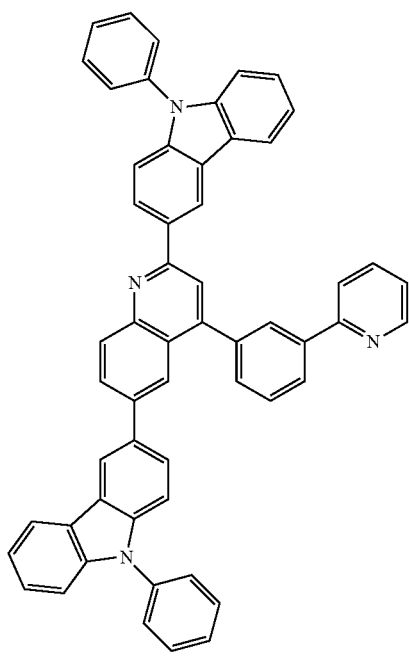
[A-296]
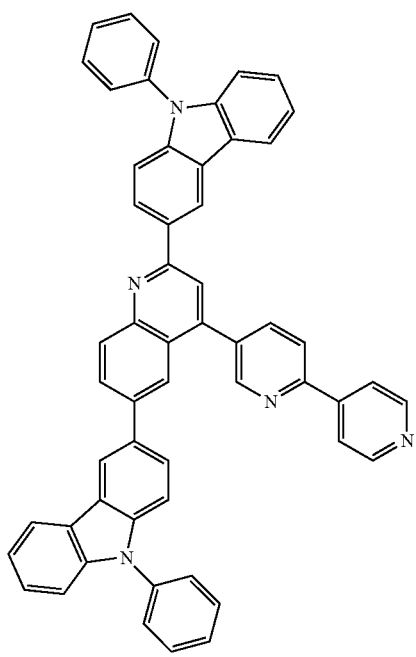

[A-297]
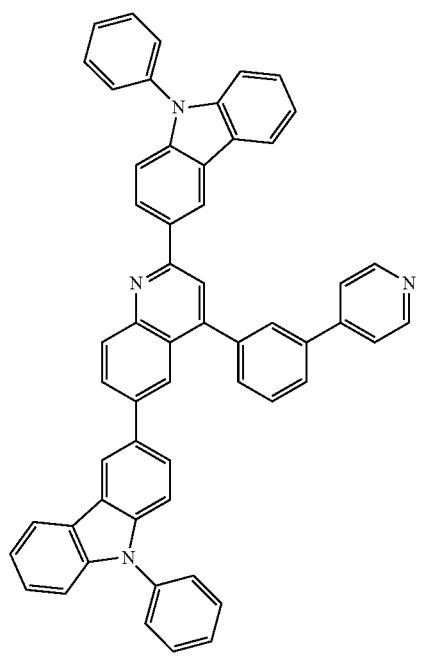
[A-299]
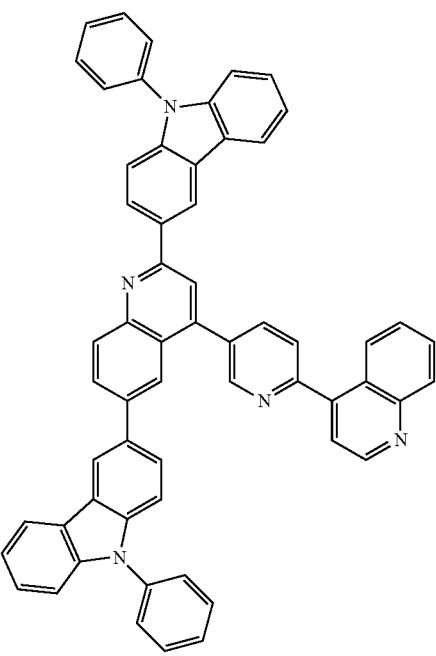
[A-298]
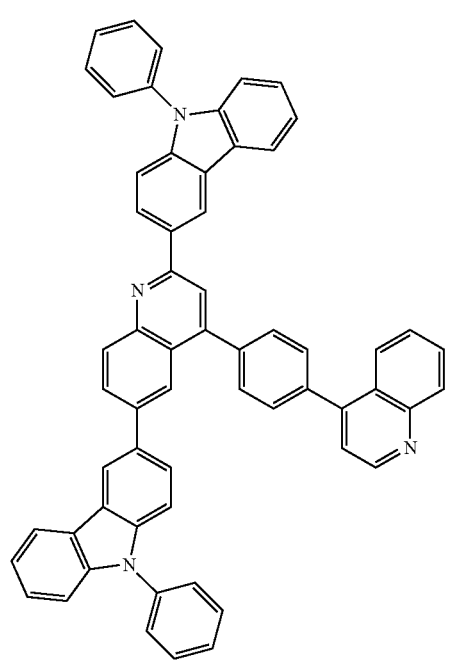
[A-300]
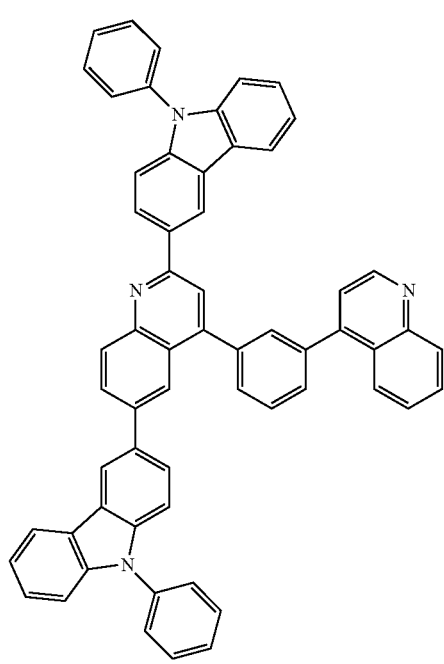

[A-301]
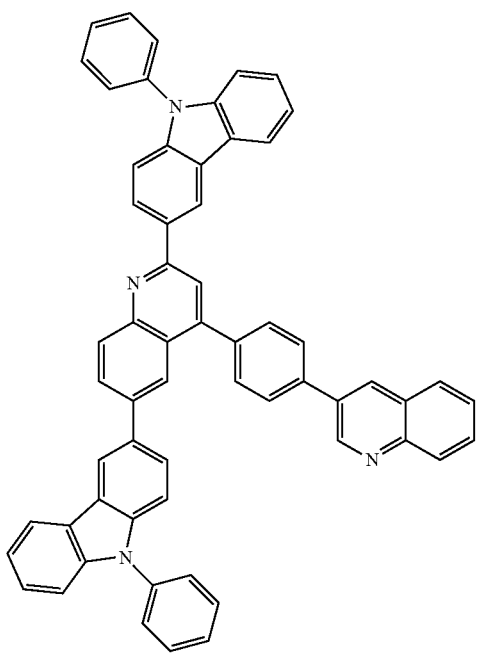
[A-303]
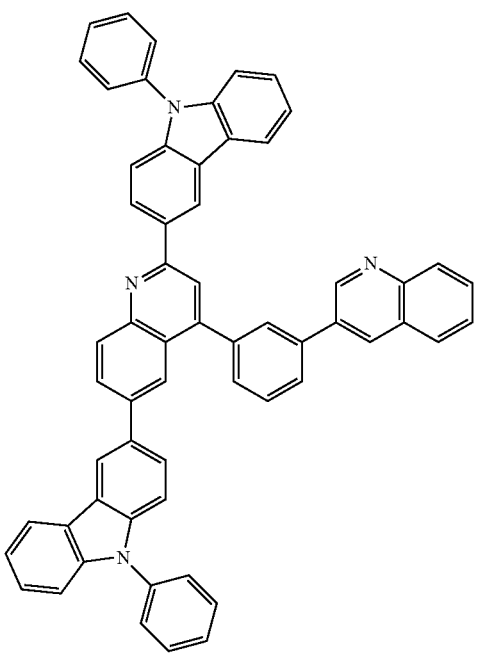
[A-302]
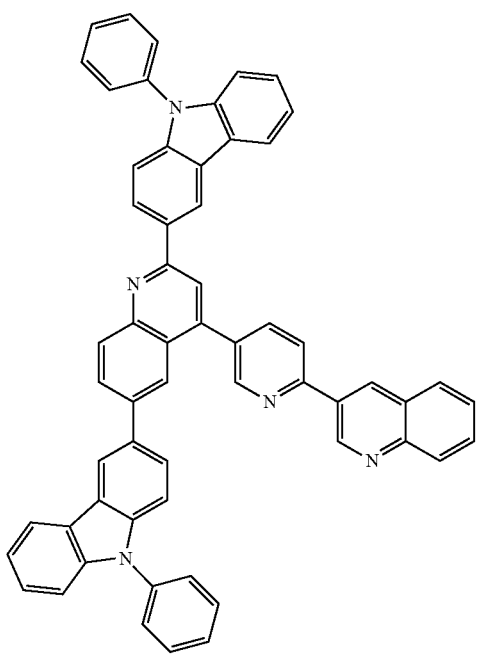
[A-304]
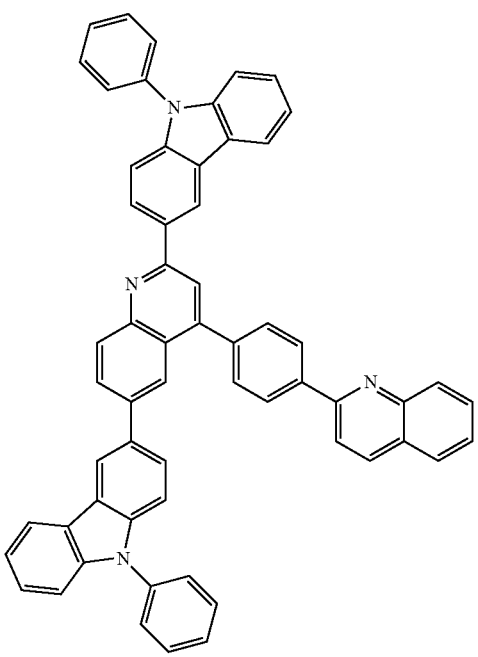

-continued
[A-305]
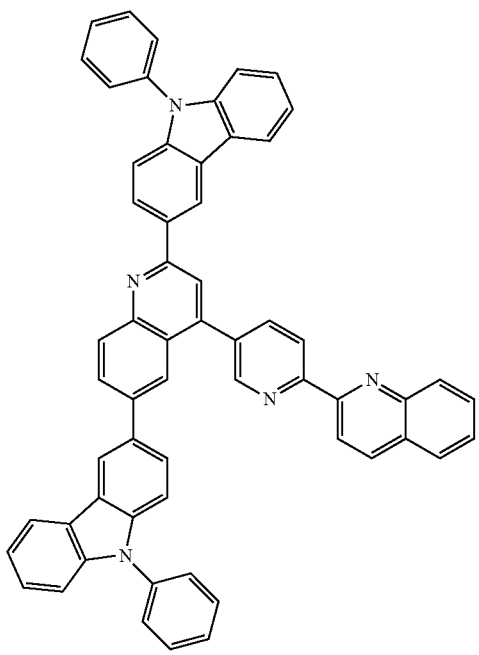
[A-307]
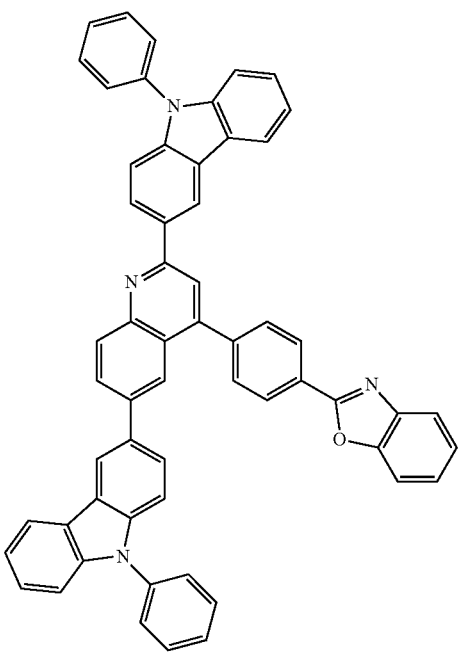
[A-306]
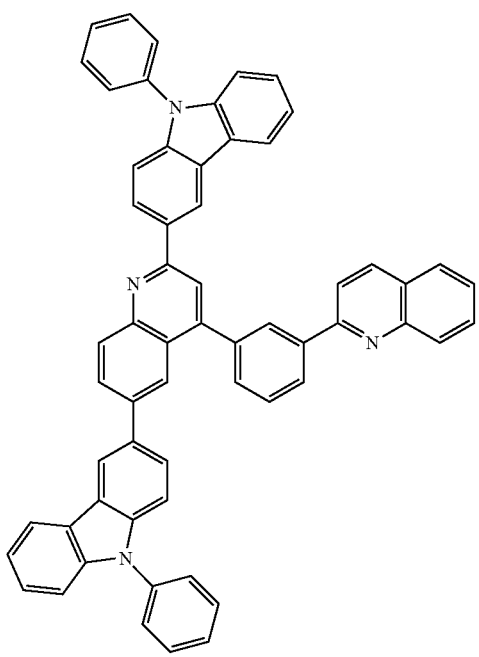
[A-308]
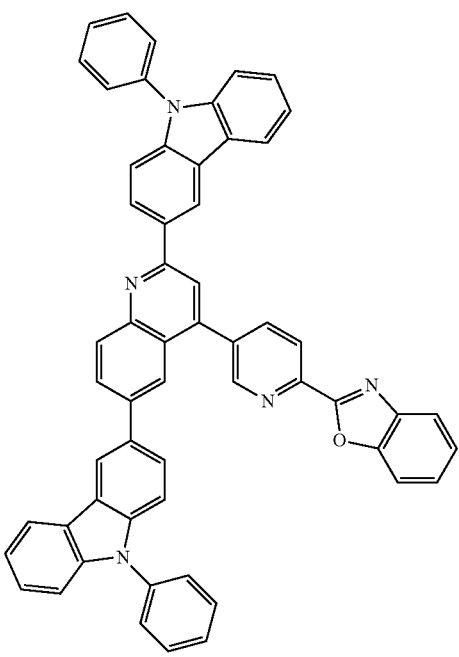

[A-309]
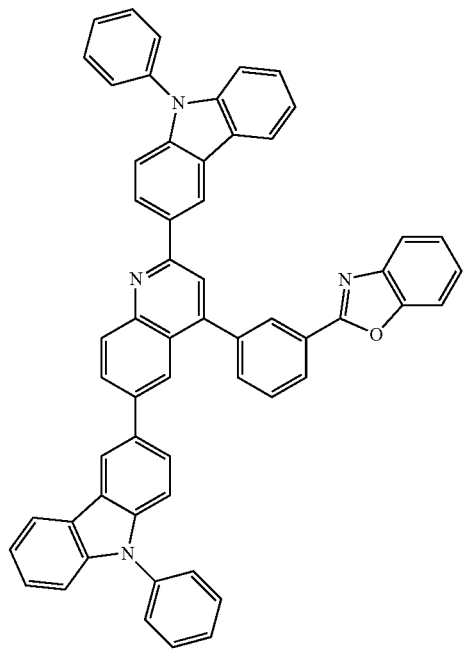
[A-310]
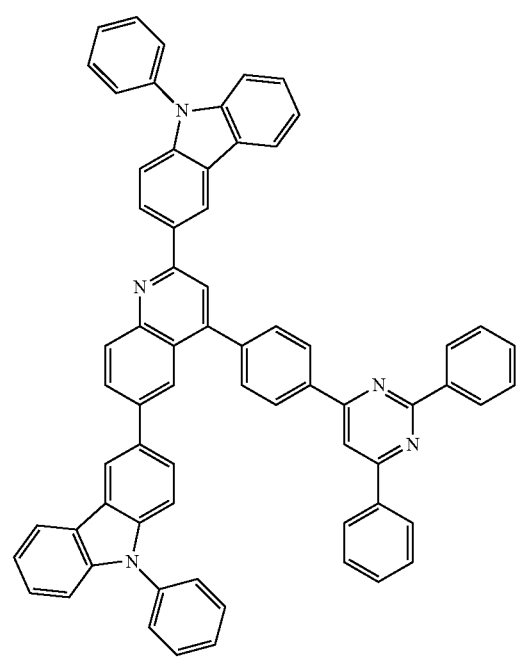
[A-311]
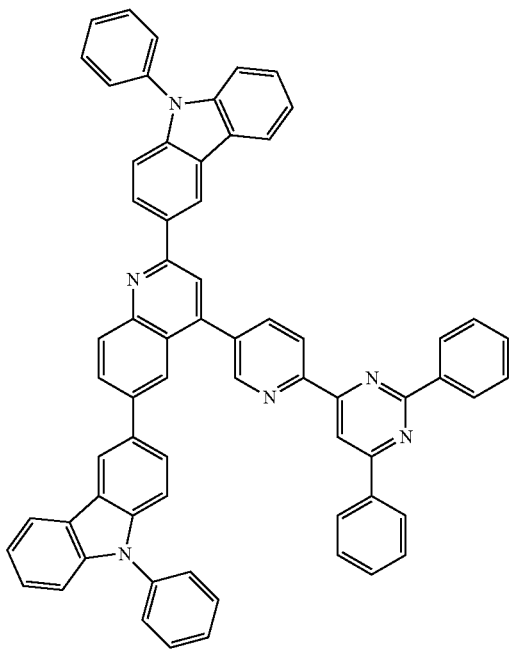
[A-312]
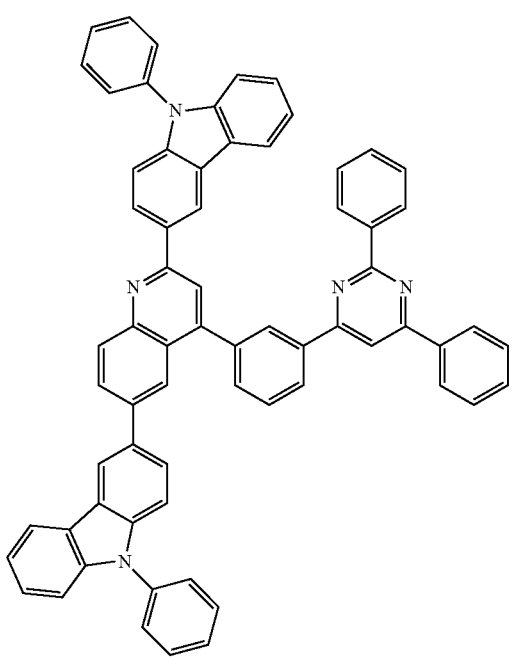

-continued
[A-313]
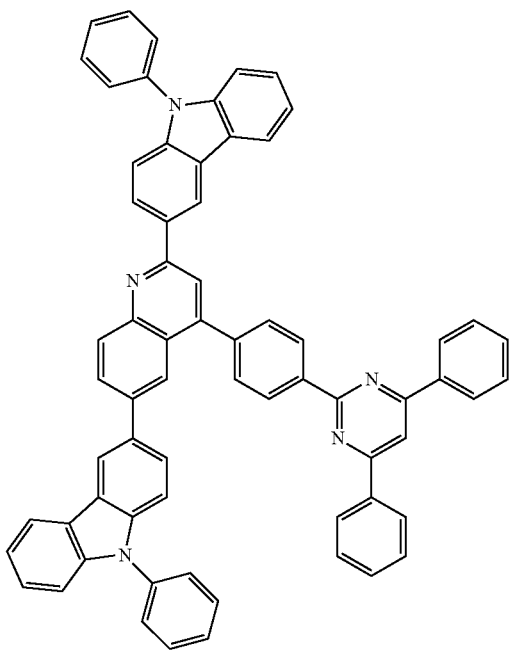
[A-315]
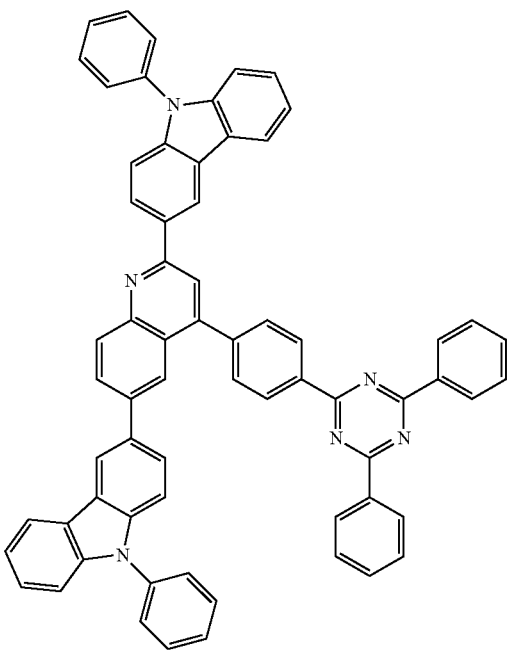
[A-314]
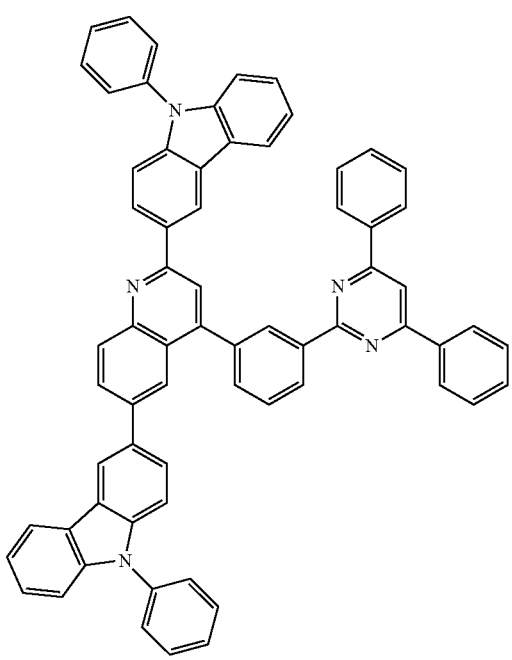
[A-316]
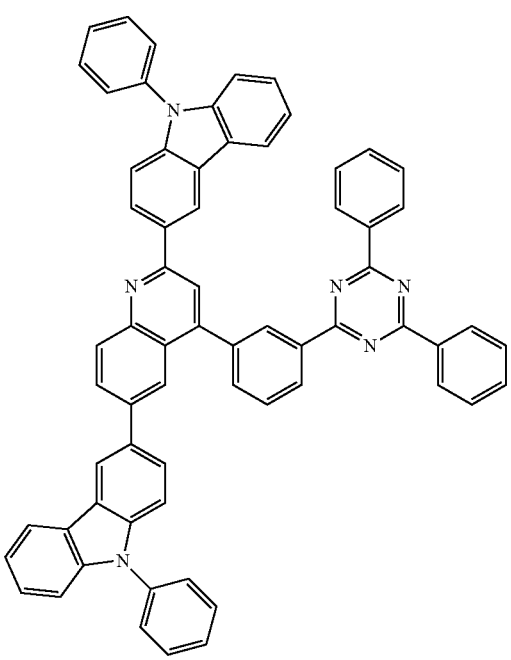

[A-317]
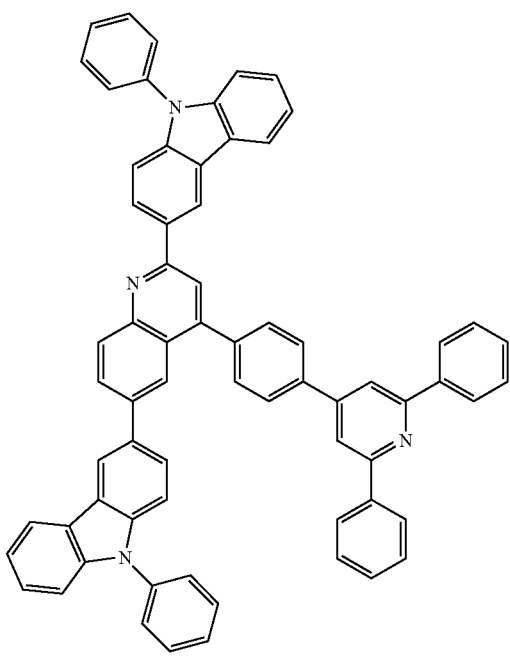
[A-319]
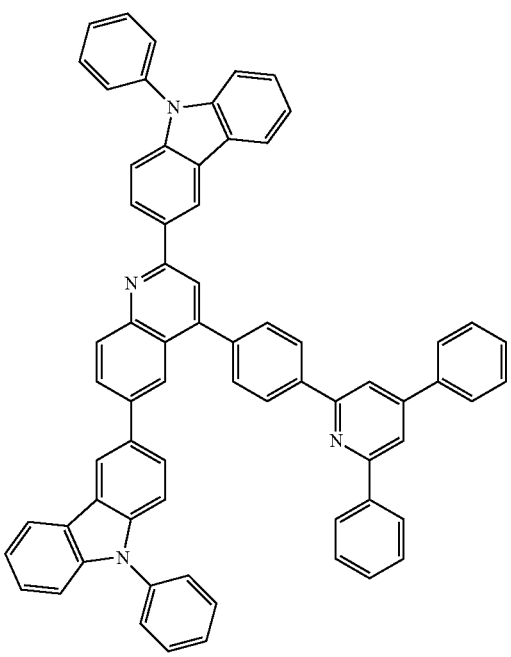
[A-318]
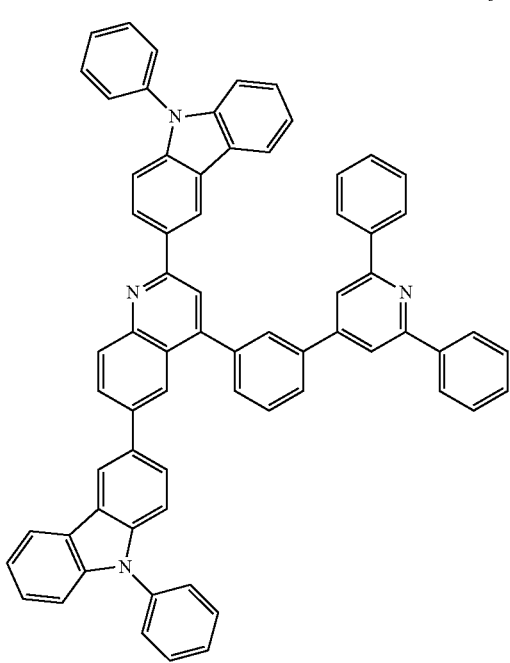
[A-320]
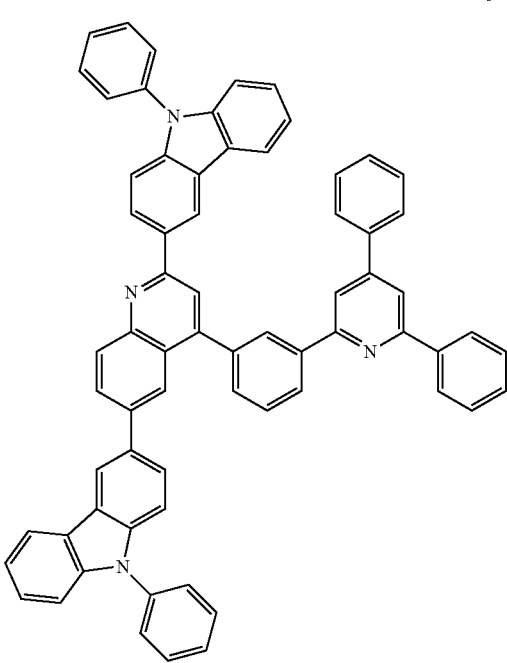

[A-321]
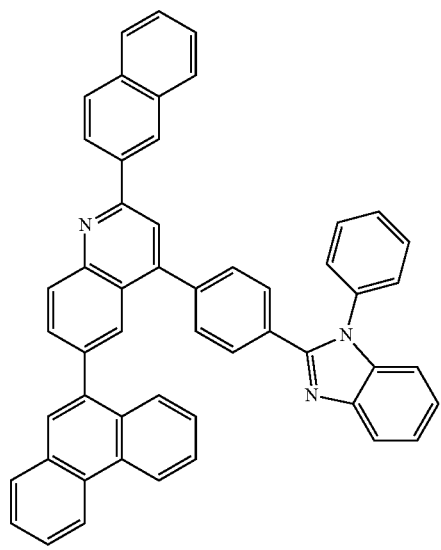
[A-324]
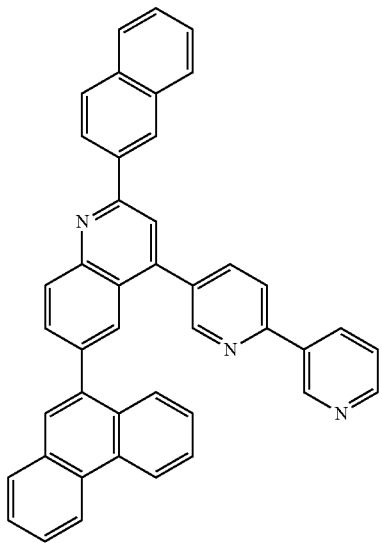
[A-322]
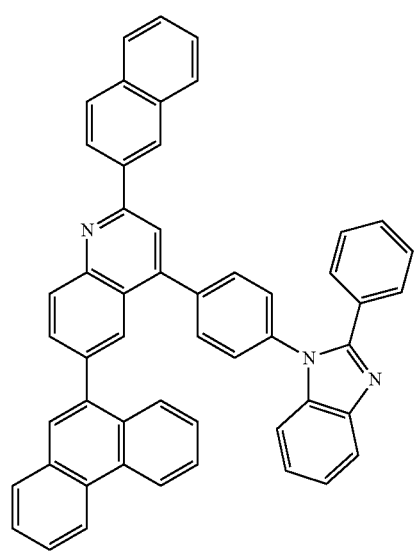
[A-325]
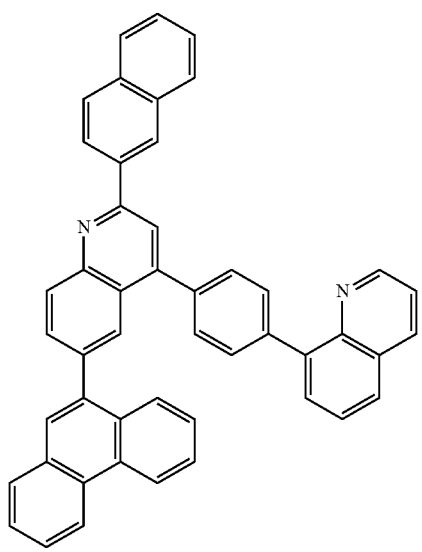
[A-323]
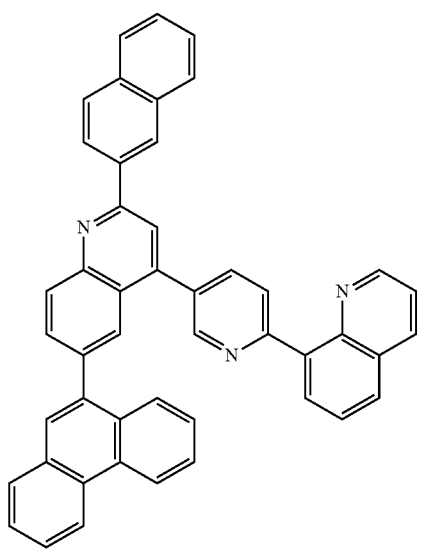
[A-326]
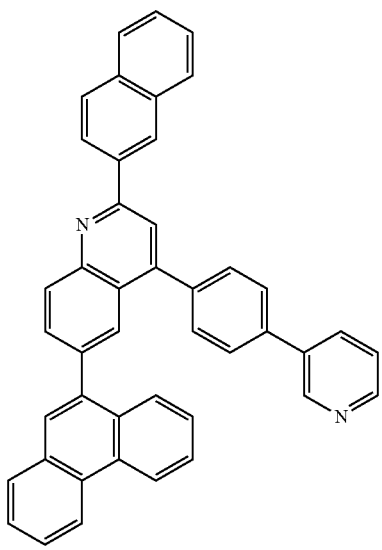

[A-327]
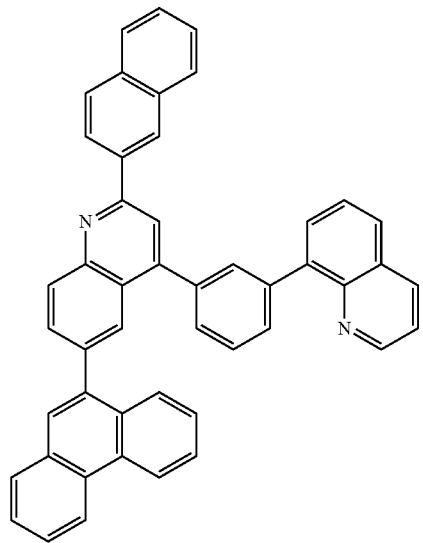
[A-330]
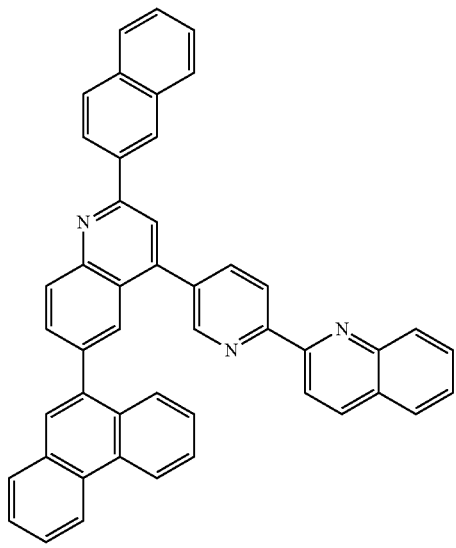
[A-328]
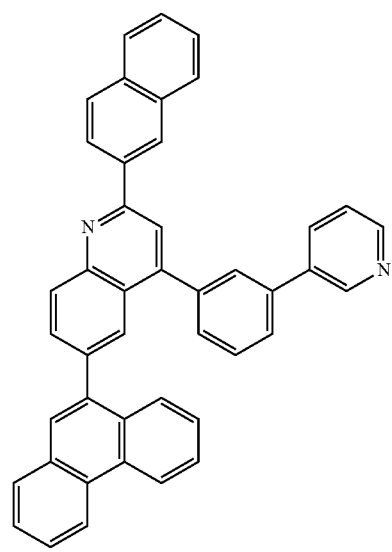
[A-331]
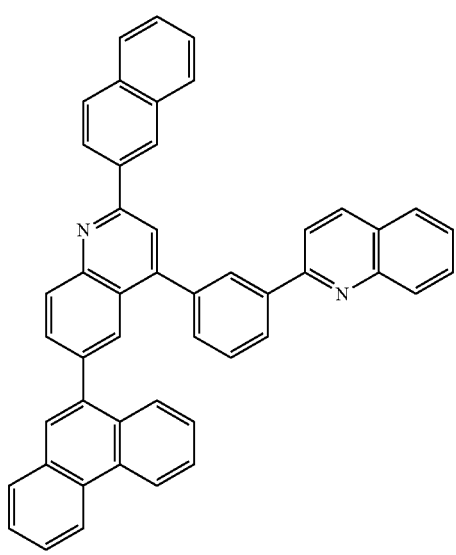
[A-329]
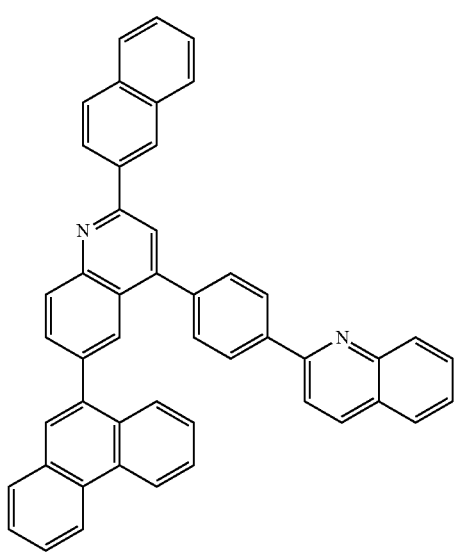
[A-332]
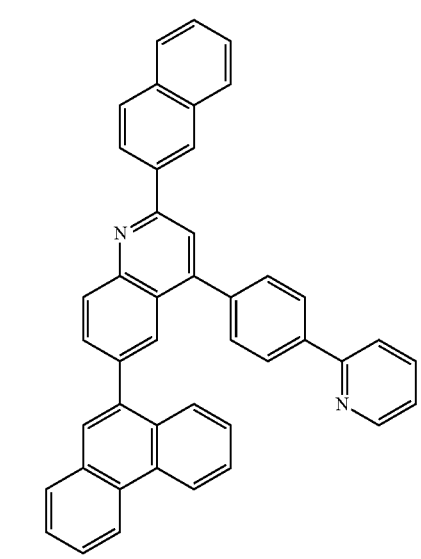

[A-333]
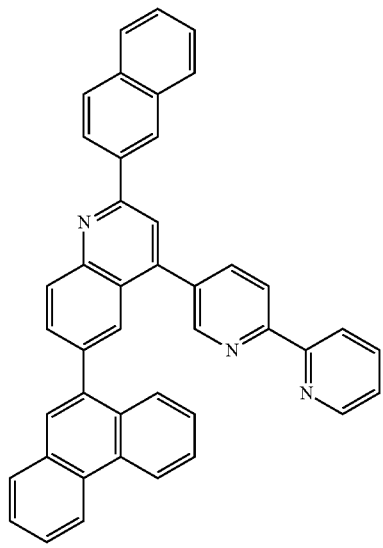
[A-336]
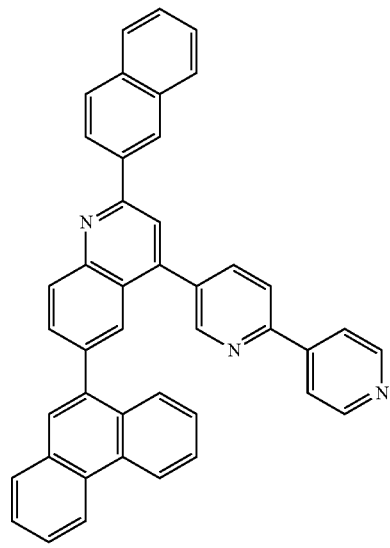
[A-334]
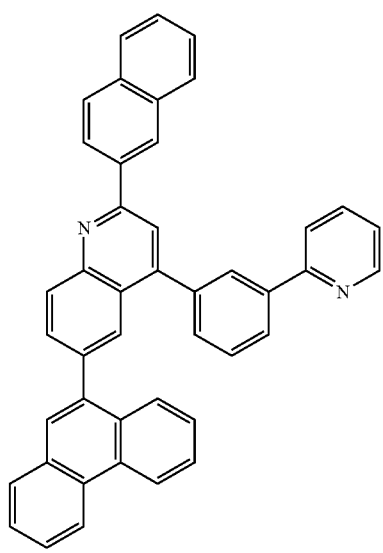
[A-337]
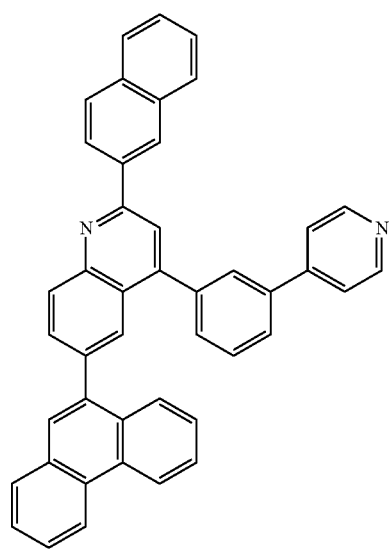
[A-335]
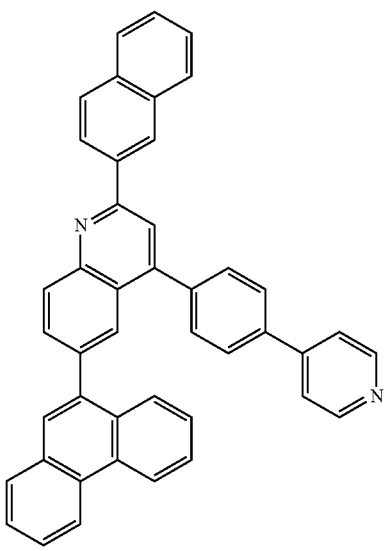
[A-338]
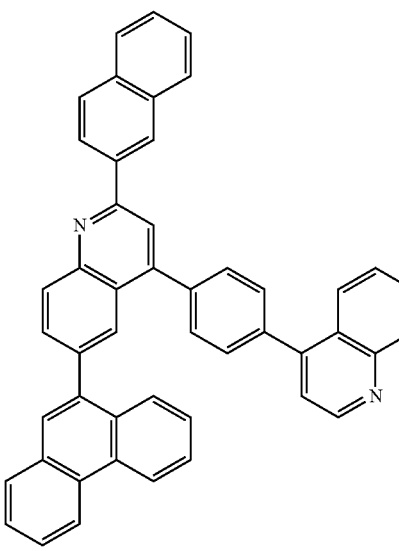

[A-339]
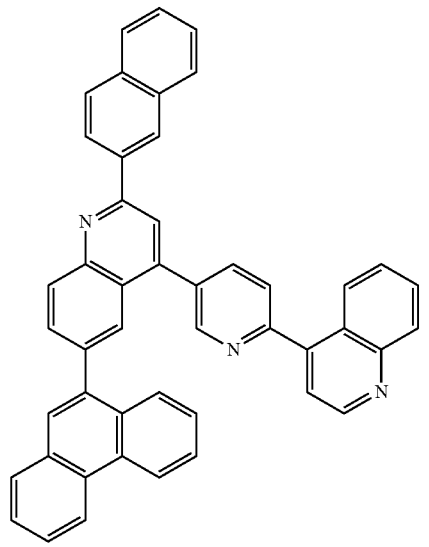
[A-342]
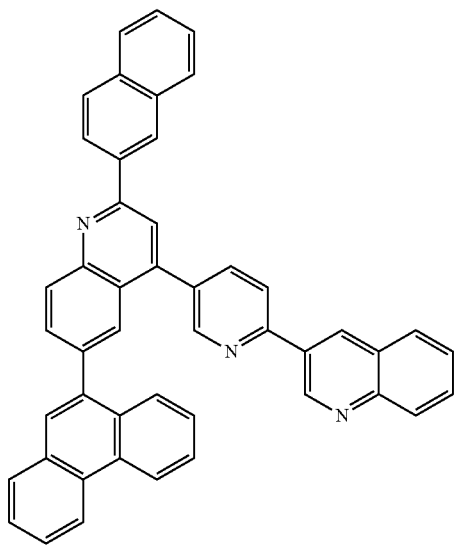
[A-340]
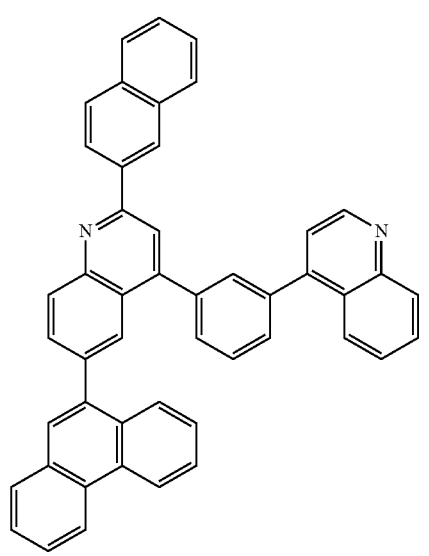
[A-343]
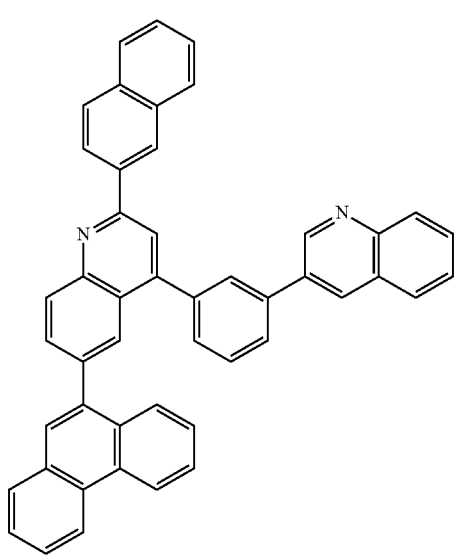
[A-341]
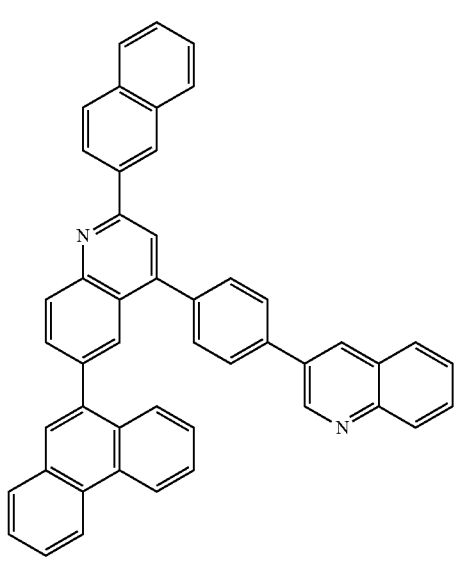
[A-344]
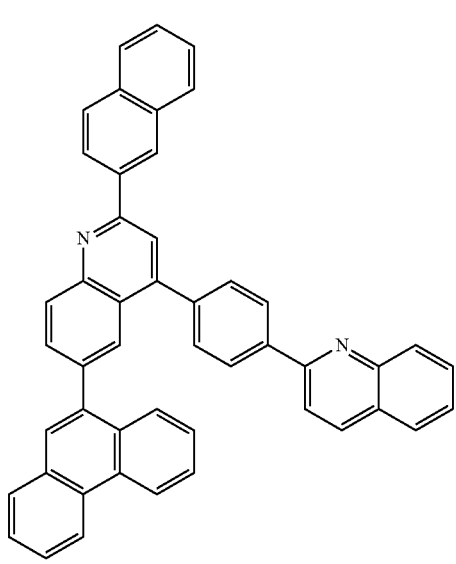

[A-345]
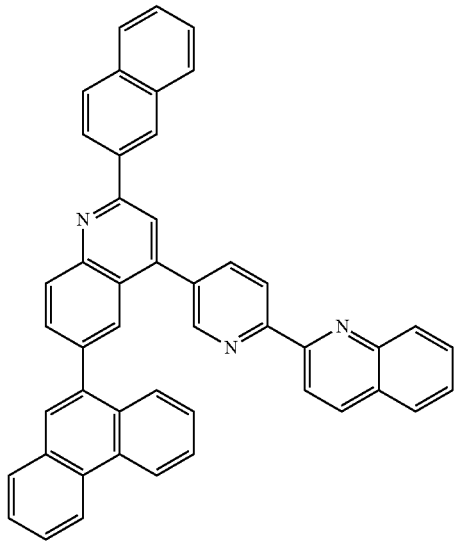
[A-348]
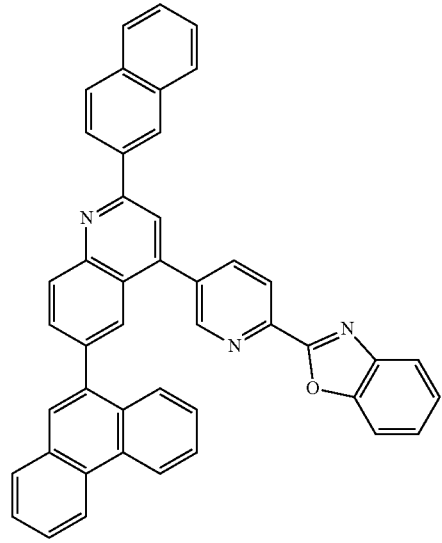
[A-346]
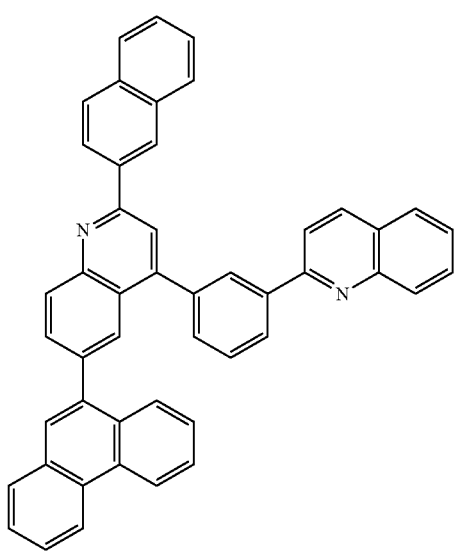
[A-349]
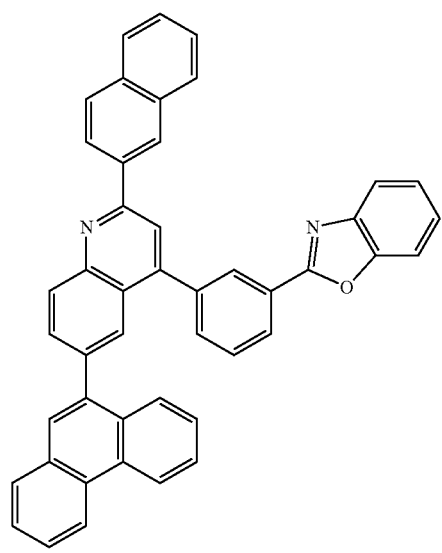
[A-347]
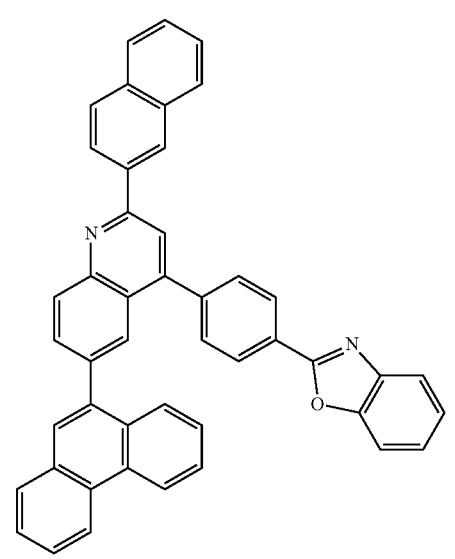
[A-350]
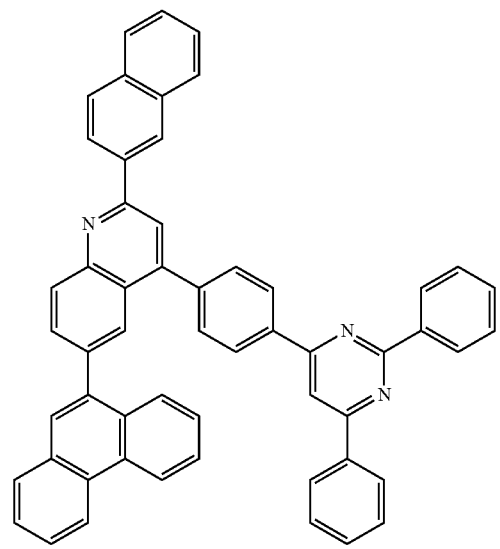

[A-351]
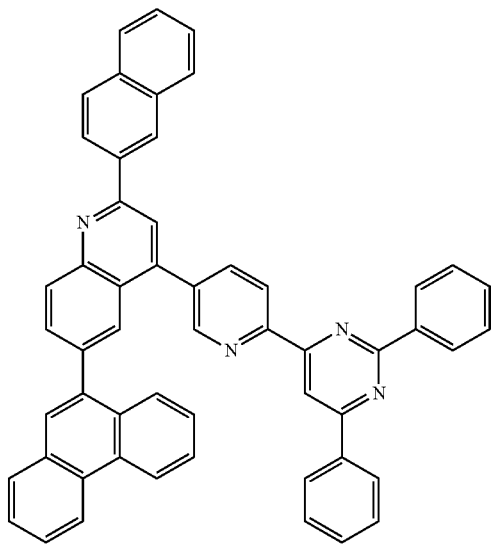
[A-353]
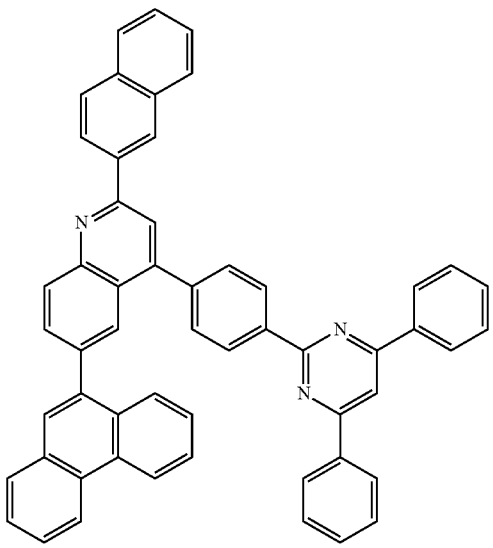
[A-352]
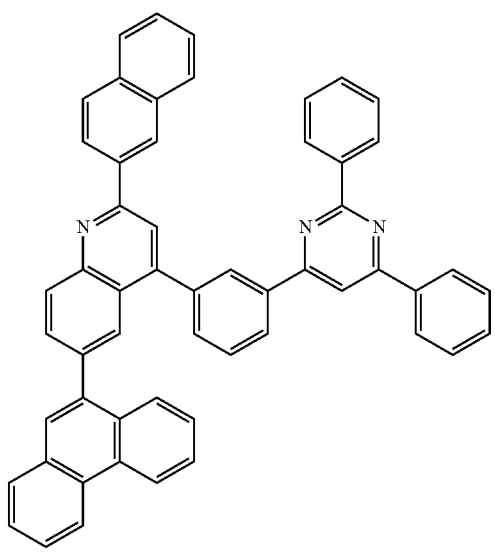
[A-354]
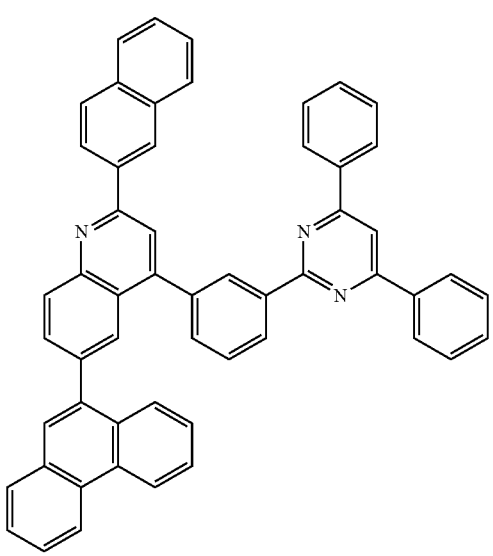

[A-355]
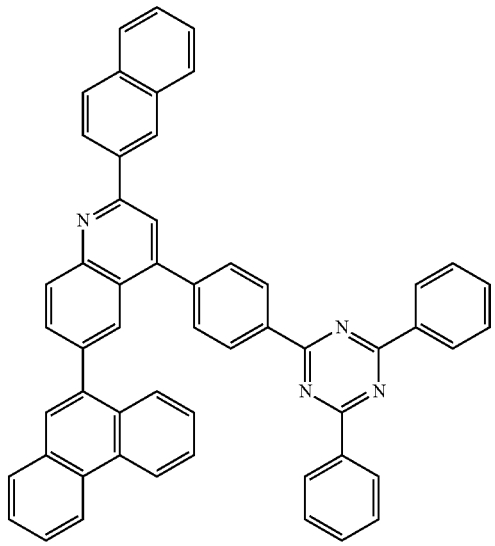
[A-357]
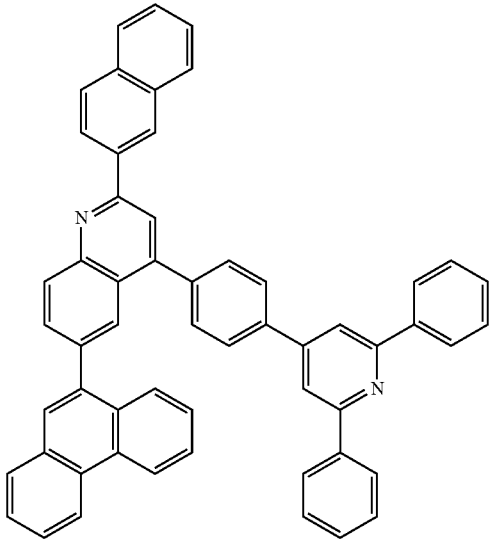
[A-356]
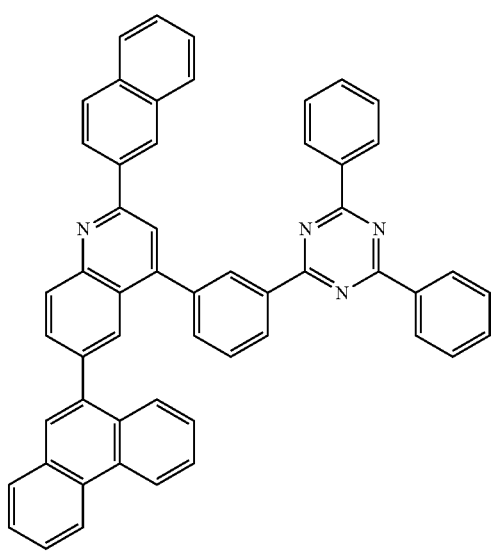
[A-358]
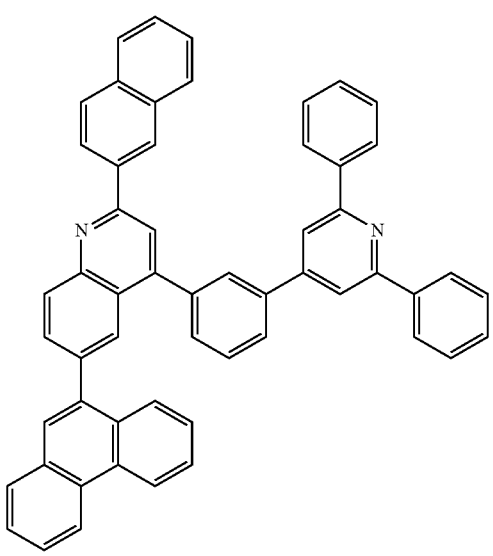

-continued

[A-359]

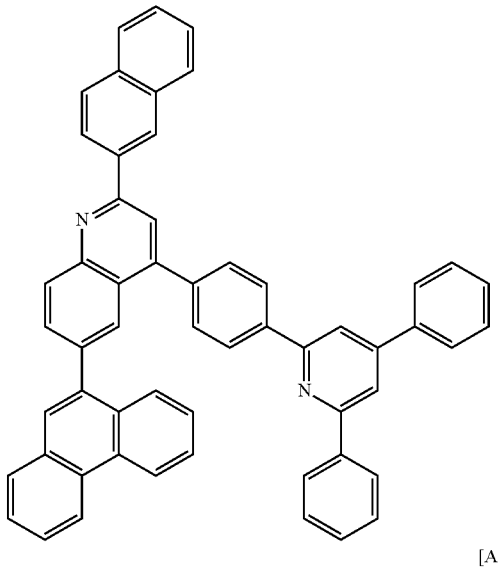

[A-360]

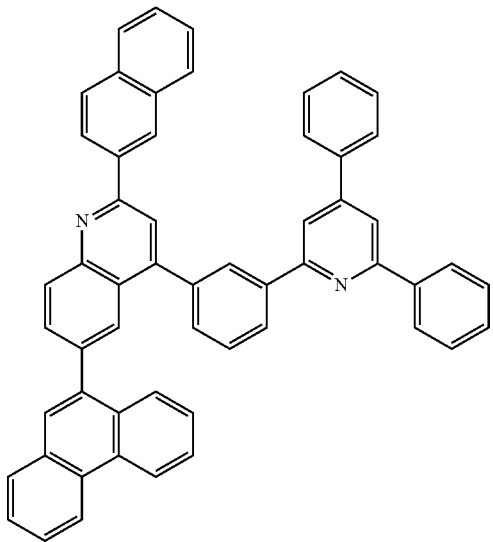

In another embodiment of the present invention, provided is an organic optoelectric device that includes an anode, cathode, and an organic thin layer interposed between the anode and the cathode, wherein at least one layer of the organic thin layer includes the compound according to one embodiment of the present invention.

The compound for an organic optoelectric device is used in an organic thin layer and thus improves life-span characteristics, efficiency characteristic, electrochemical stability and thermal stability of an organic optoelectric device, and lowers a driving voltage.

The organic thin layer may be specifically an emission layer.

The organic optoelectric device may be an organic light emitting diode, an organic photoelectric device, an organic solar cell, an organic transistor, an organic photo conductor drum, or an organic memory device.

More specifically, the organic optoelectric device may be an organic light emitting diode.

Hereinafter, as an example of an organic optoelectric device, an organic light emitting diode is described referring to drawings.

FIGS. 1 and 2 are cross-sectional views of an organic light emitting diode according to one embodiment.

Referring to FIG. 1, an organic optoelectric device 100 according to one embodiment includes an anode 120 and a cathode 110 facing each other and an organic layer 105 between the anode 120 and the cathode 110.

The anode 120 may be made of a conductor having a high work function to help hole injection, for example metal, a metal oxide and/or a conductive polymer. The anode 120 may include, for example a metal or an alloy thereof such as nickel, platinum, vanadium, chromium, copper, zinc, and gold; metal oxide such as zinc oxide, indium oxide, indium tin oxide (ITO), and indium zinc oxide (IZO); a combination of a metal and an oxide such as ZnO and Al or $SnO_2$ and Sb; a conductive polymer such as poly (3-methylthiophene), poly (3,4-(ethylene-1,2-dioxy)thiophene) (PEDT), polypyrrole and polyaniline, but is not limited thereto.

The cathode 110 may be made of a conductor having a low work function to help electron injection, for example a metal, a metal oxide and/or a conductive polymer. The cathode material may include, for example a metal or an alloy thereof such as magnesium, calcium, sodium, potassium, titanium, indium, yttrium, lithium, gadolinium, aluminum silver, tin, lead, cesium, barium, and the like; a multi-layer structured material such as LiF/Al, $LiO_2$/Al, LiF/Ca, LiF/Al and $BaF_2$/Ca, but is not limited thereto.

The organic layer 105 includes an emission layer 130 including the compound.

The emission layer 130 may include, for example the compound at alone or with at least two of the compounds, or as a mixture with other different compound from the compound. When the compound is mixed with the other compound, for example they may be included as a host and a dopant, wherein the compound may be, for example included as a host. The host may be, for example phosphorescent host or fluorescent host, for example a phosphorescent host.

When the compound is included as a host, the dopant may be selected from well-known inorganic, organic, organic/inorganic compound as a dopant.

Referring to FIG. 2, an organic light emitting diode 200 further includes a hole auxiliary layer 140 as well as an emission layer 230. The hole auxiliary layer 140 may further increase hole injection and/or hole mobility between the anode 120 and emission layer 230 and block electrons. The hole auxiliary layer 140 may be, for example a hole transport layer (HTL), a hole injection layer (HIL), and/or an electron blocking layer, and may include at least one layer. The compound may be included in the emission layer 230 and/or the hole auxiliary layer 140.

Even though not being shown in FIG. 1 or 2, the organic layer 105 may further include an electron injection layer (EIL), an electron transport layer (ETL), an auxiliary electron transport layer (ETL), a hole transport layer (HTL), an auxiliary hole transport layer (HTL), a hole injection layer (HIL), or a combination thereof. The compound of the present invention may be included in these organic layers. The organic light emitting diodes 100 and 200 may be manufactured by forming an anode or a cathode on a substrate, forming an organic layer in accordance with a dry coating method such as evaporation, sputtering, plasma plating, and ion plating; or a wet coating method such as spin coating, slit coating, dipping, flow coating and inkjet printing; and forming a cathode or an anode thereon.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

(Preparation of Compound for Organic Optoelectric Device)

EXAMPLE 1

Synthesis of Compound A-1

The compound A-1 was synthesize through the following 4 step processes provide in the following Reaction Scheme 1.

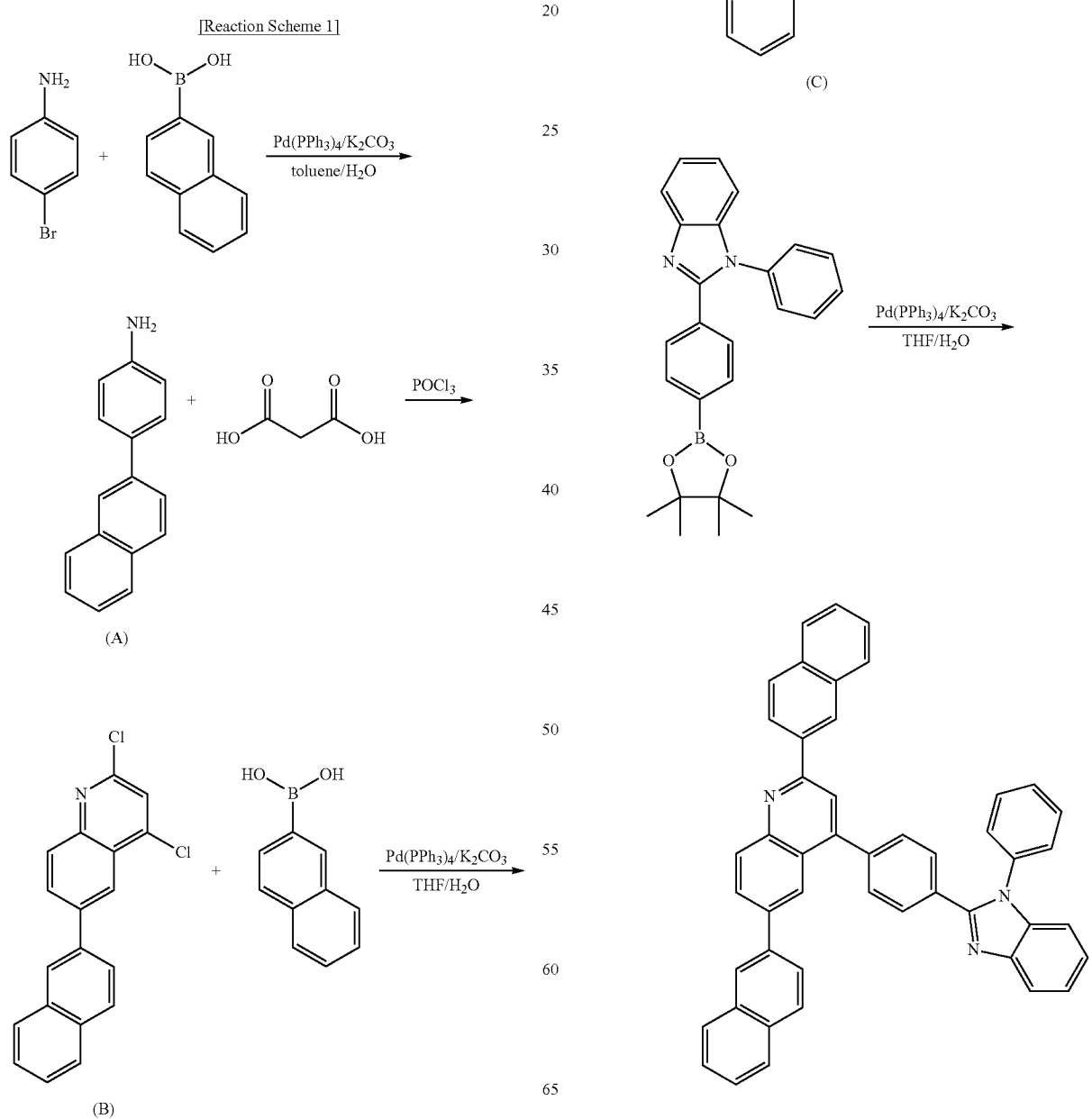

First Step; Synthesis of Intermediate Product (A)

58.0 g (337.2 mmol) of 4-bromoaniline, 69.6 g (404.6 mmol) of 2-naphthaleneboronic acid and 9.7 g (8.4 mmol) of tetrakis(triphenylphosphine)palladium [Pd(PPh$_3$)$_4$] were dissolved in 1700 ml of a toluene solvent, a solution obtained by dissolving 93.2 g (674.3 mmol) of potassium carbonate (K$_2$CO$_3$) in 600 ml of water was added thereto, and the mixture was reacted at 100° C. for 12 hours. Then, an aqueous layer was removed from the obtained reactant, and a product obtained after removing a solvent under a reduced pressure was washed with water and methanol. The obtained solid mixture was separated through column and dried, obtaining 50.0 g of a yellow solid intermediate product (A) (a yield: 68%).

Second Step; Synthesis of Intermediate Product (B)

27.0 g (123.1 mmol) of the intermediate product A and 19.2 g (184.7 mmol) of malonic acid were dissolved in 110 ml of a phosphorus oxychloride (POCl$_3$) solvent, and the solution was reacted at 140° C. for 4 hours.

The obtained reactant was poured into ice water, and a solid formed therein was filtered and washed with water and a sodium bicarbonate-saturated aqueous solution. The obtained solid mixture was washed with methanol and dried, obtaining 9.6 g of a light yellow solid intermediate product (B) (a yield: 24%).

Third Step: Synthesis of Intermediate Product (C)

9.5 g (29.3 mmol) of the intermediate product (B), 5.0 g (29.3 mmol) of 2-naphthaleneboronic acid and 1.0 g (0.9 mmol) of tetrakis(triphenylphosphine)palladium [Pd(PPh$_3$)$_4$] were dissolved in 190 ml of tetrahydrofuran (THF), a solution obtained by dissolving 8.1 g (58.6 mmol) of potassium carbonate (K$_2$CO$_3$) in 95 ml of water was added thereto, and the mixture was reacted at 70° C. for 12 hours. The resultant was cooled down to room temperature, and a solid mixture formed therein was filtered through a glass filter. The residue was recrystallized with monochloro benzene, and a crystal precipitated therein was separated through a filter and washed with monochloro benzene and dried, obtaining 9.19 g of a white solid intermediate product (C) (a yield: 75%).

Fourth Step: Synthesis of Compound A-1

9.0 g (21.6 mmol) of the intermediate product (C), 10.3 g (23.9 mmol) of 1-phenyl-2-(4-(4,4,5,5-tetramethyl-1,3,2-dioxaborolan-2-yl)phenyl)-1H-benzoimidazole and 0.8 g (0.7 mmol) of tetrakis(triphenylphosphine)palladium [Pd(PPh$_3$)$_4$] were dissolved in 180 ml of tetrahydrofuran (THF), a solution obtained by dissolving 11.9 g (86.6 mmol) of potassium carbonate (K$_2$CO$_3$) in 90 ml of water was added thereto, and the mixture was reacted at 90° C. for 12 hours. Then, a solvent was removed from the obtained reactant under a reduced pressure, and a produce obtained therefrom was washed with water and methanol. The residue was recrystallized with toluene, and a precipitate obtained therefrom was separated and clean with toluene and then, dried, obtaining 11.0 g of a white solid compound (a yield: 81%). (calculation value: 649.78, measurement value: MS[M+1] 650.08)

EXAMPLE 2

Synthesis of Compound A-2

The compound A-2 was synthesized through the following Reaction Scheme 2.

[Reaction Scheme 2]

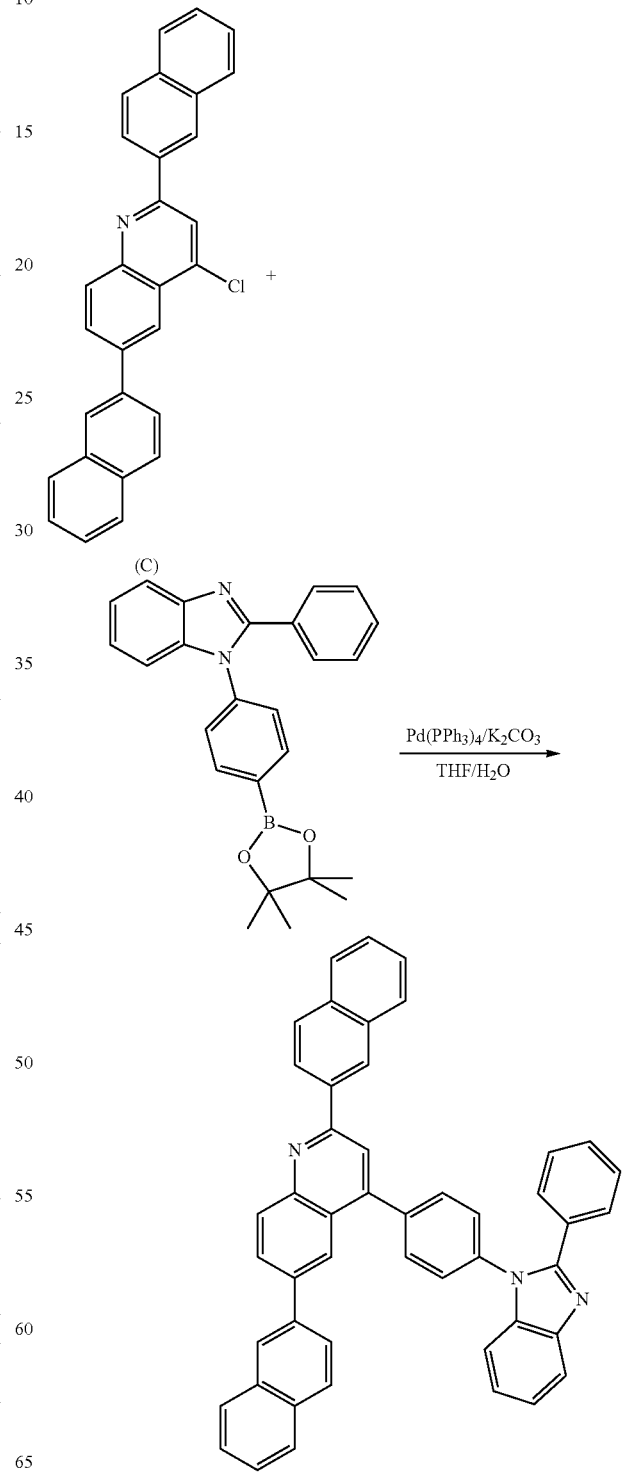

15.0 g (36.1 mmol) of the intermediate product (C), 17.2 g (43.3 mmol) of 2-phenyl-1-(4-(4,4,5,5-tetramethyl-1,3,2-dioxaborolan-2-yl)phenyl)-1H-benzoimidazole and 1.3 g (1.1 mmol) of tetrakis(triphenylphosphine)palladium [Pd (PPh₃)₄] were dissolved in 300 ml of tetrahydrofuran (THF) as a solvent, a solution obtained by dissolving 19.9 g (144.3 mmol) of potassium carbonate (K₂CO₃) in 150 ml of water was added thereto, and the mixture was reacted at 90° C. for 12 hours. Then, a solvent was removed from the obtained reactant under a reduced pressure, and a produce therefrom was washed with water and methanol. The residue was recrystallized with toluene, and a precipitate obtained therefrom was separated through a filter and washed with toluene and then, dried, obtaining 18.0 g of a white solid compound (a yield: 77%). (calculation value: 649.78, measurement value: MS[M+1] 650.08)

EXAMPLE 3

Synthesis of Compound A-3

The compound A-3 was synthesized through the following Reaction Scheme 3.

[Reaction Scheme 3]

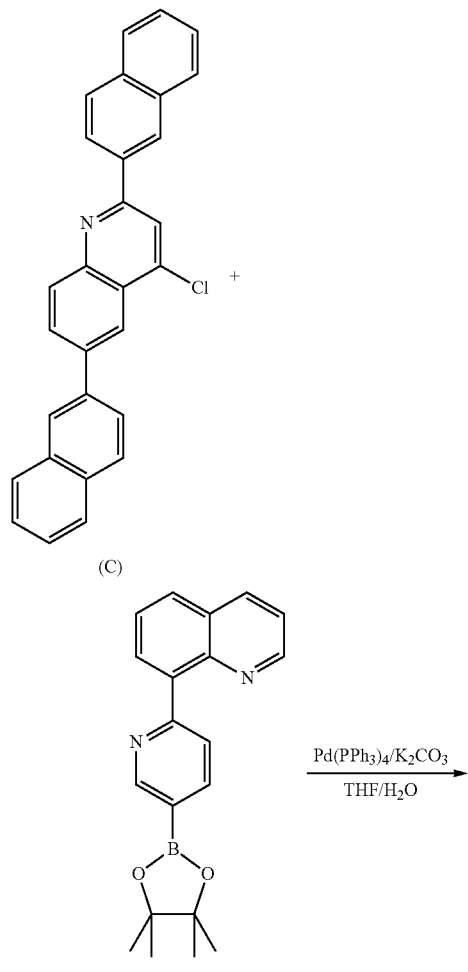

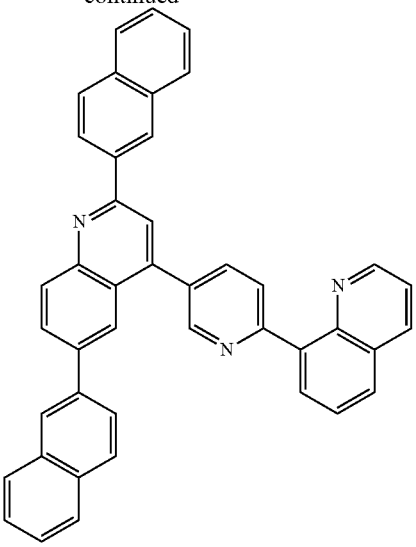

12.0 g (28.9 mmol) of the intermediate product (C), 11.5 g (34.6 mmol) of 8-(5-(4,4,5,5-tetramethyl-1,3,2-dioxaborolan-2-yl)-pyridine-2-yl)quinoline and 1.0 g (0.9 mmol) of tetrakis(triphenylphosphine)palladium [Pd(PPh₃)₄] were dissolved in 240 ml of tetrahydrofuran (THF) as a solvent, a solution obtained by dissolving 15.9 g (115.4 mmol) of potassium carbonate (K₂CO₃) in 120 ml of water was added thereto, and the mixture was reacted at 90° C. for 12 hours. Then, a solvent was removed from the obtained reactant under a reduced pressure, and a product therefrom was washed with water and methanol. The residue was recrystallized with toluene, and a precipitate therefrom was separated through a filter and washed with toluene and then, dried, obtaining 13.0 g of a white solid compound (a yield: 77%). (calculation value: 585.69, measurement value: MS[M+1] 585.99)

EXAMPLE 4

Synthesis of Compound A-4

The compound A-4 was synthesized through the following Reaction Scheme 4.

[Reaction Scheme 4]

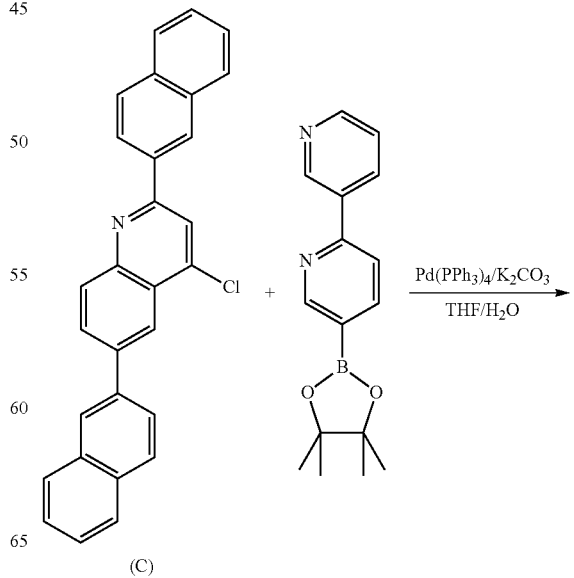

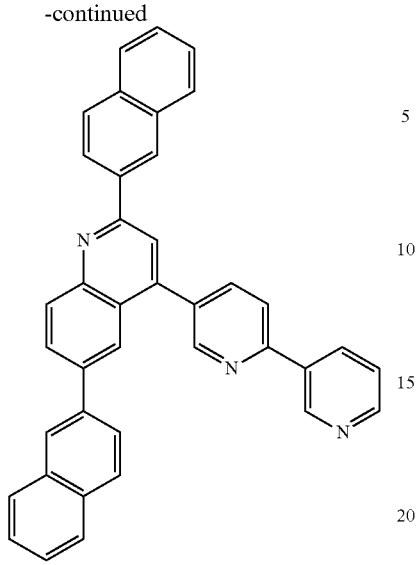

11.5 g (27.7 mmol) of the intermediate product (C), 9.4 g (33.2 mmol) of 3-(5-(4,4,5,5-tetramethyl-1,3,2-dioxaborolan-2-yl)-pyridine-2-yl)pyridine and 1.0 g (0.8 mmol) of tetrakis(triphenylphosphine)palladium [Pd(PPh$_3$)$_4$] were dissolved in 230 ml of tetrahydrofuran (THF) as a solvent, a solution obtained by dissolving 15.3 g (110.6 mmol) of potassium carbonate (K$_2$CO$_3$) in 115 ml of water was added thereto, and the mixture was reacted at 90° C. for 12 hours. Then, a solvent was removed from the obtained reactant under a reduced pressure, and a product therefrom was washed with water and methanol. The residue was recrystallized with toluene, and a precipitate therefrom was separated through a filter and washed with toluene and then, dried, obtaining 9.7 g of a white solid compound (a yield: 65%). (calculation value: 535.64, measurement value: MS[M+1] 535.94)

EXAMPLE 5

Synthesis of Compound A-5

The compound A-5 was synthesized through the following Reaction Scheme 5.

[Reaction Scheme 5]

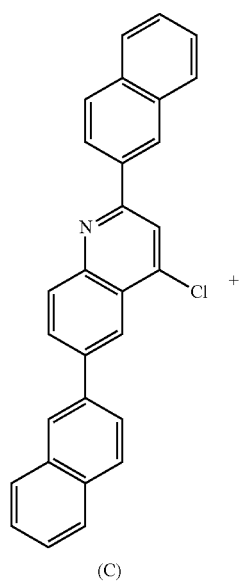

(C)

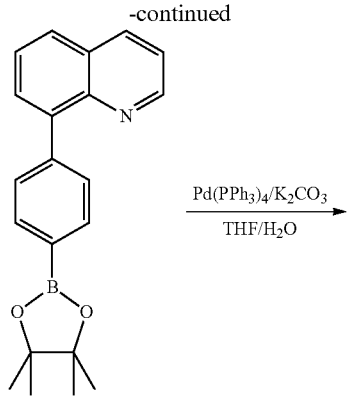

15.0 g (36.1 mmol) of the intermediate product (C), 14.3 g (43.3 mmol) of 8-(4-(4,4,5,5-tetramethyl-1,3,2-dioxaborolan-2-yl)-phenyl)quinoline and 1.3 g (1.1 mmol) of tetrakis(triphenylphosphine)palladium [Pd(PPh$_3$)$_4$] were dissolved in 300 ml of tetrahydrofuran (THF) as a solvent, a solution obtained by dissolving 19.9 g (144.3 mmol) of potassium carbonate (K$_2$CO$_3$) in 150 ml of water was added thereto, and the mixture was reacted at 90° C. for 12 hours. Then, a solvent was removed from the obtained reactant under a reduced pressure, and a product therefrom was washed with water and methanol. The residue was recrystallized with toluene, and a precipitate therefrom was separated through a filter and washed with toluene and then, dried, obtaining 15.0 g of a white solid compound (a yield: 71%). (calculation value: 584.71, measurement value: MS[M+1] 585.01)

EXAMPLE 6

Synthesis of Compound A-6

The compound A-6 was synthesized through the following Reaction Scheme 6.

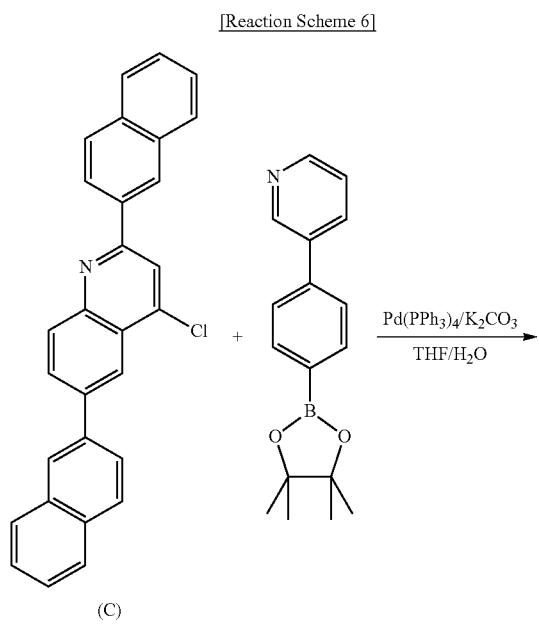

16.0 g (34.3 mmol) of the intermediate product (C), 11.6 g (41.2 mmol) of 3-(4-(4,4,5,5-tetramethyl-1,3,2-dioxaborolan-2-yl)phenyl)pyridine and 1.2 g (1.0 mmol) of tetrakis (triphenylphosphine)palladium [Pd(PPh$_3$)$_4$] were dissolved in 320 ml of tetrahydrofuran (THF) as a solvent, a solution obtained by dissolving 19.0 g (56.5 mmol) of potassium carbonate (K$_2$CO$_3$) in 160 ml of water was added thereto, and the mixture was reacted at 90° C. for 12 hours. Then, a solvent was removed from the obtained reactant under a reduced pressure, and a product therefrom was washed with water and methanol. The residue was recrystallized with toluene, and a precipitate therefrom was separated through a filter and washed with toluene and then, dried, obtaining 15.0 g of a white solid compound (a yield: 82%). (calculation value: 534.65, measurement value: MS[M+1] 534.95)

EXAMPLE 7

Synthesis of Compound A-7

The compound A-7 was synthesized through the following Reaction Scheme 7.

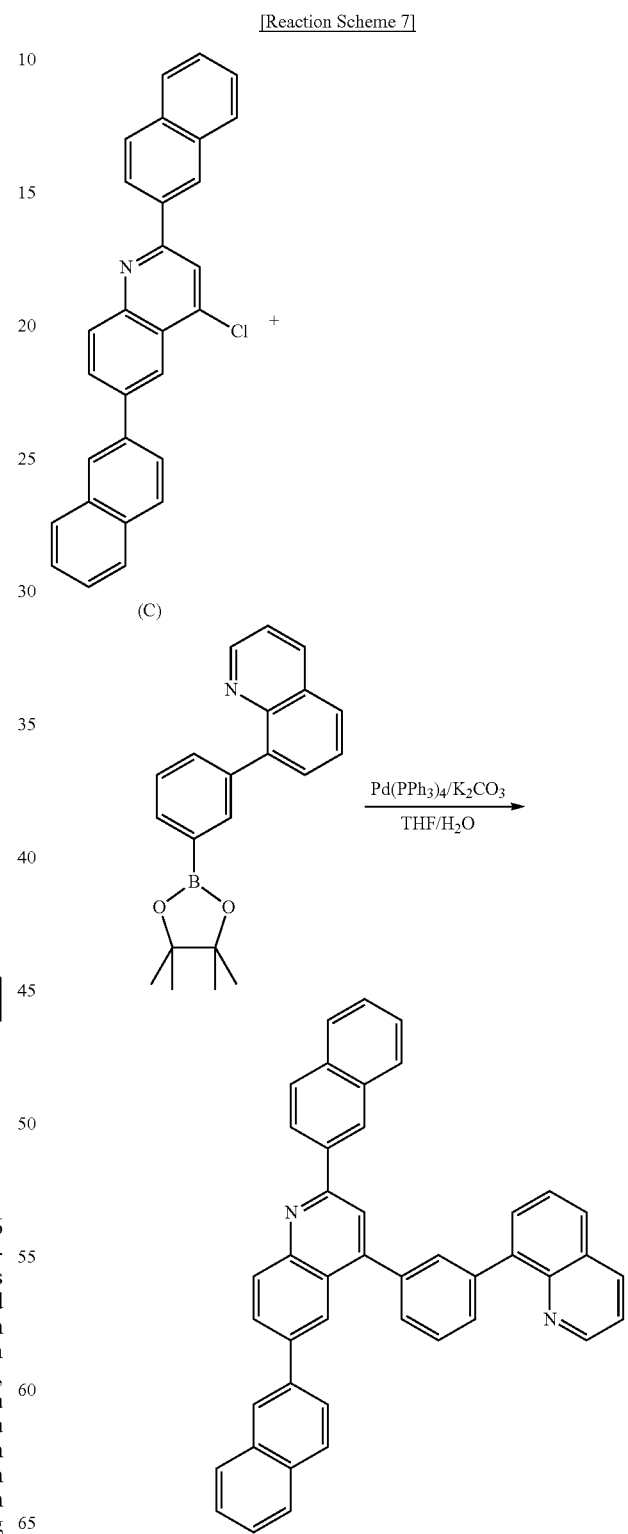

16.0 g (38.5 mmol) of the intermediate product (C), 15.3 g (46.2 mmol) of 8-(3-(4,4,5,5-tetramethyl-1,3,2-dioxaborolan-2-yl)phenyl)quinoline and 1.3 g (1.2 mmol) of tetrakis(triphenylphosphine)palladium [Pd(PPh₃)₄] were dissolved in 320 ml of tetrahydrofuran (THF) as a solvent, a solution obtained by dissolving 21.3 g (153.9 mmol) of potassium carbonate (K₂CO₃) in 160 ml of water, and the mixture was reacted at 90° C. for 12 hours. Then, a solvent was removed from the obtained reactant under a reduced pressure, and a product therefrom was washed with water and methanol. The residue was recrystallized with toluene, and a precipitate therefrom was separated through a filter and washed with toluene and then, dried, obtaining 15.8 g of a white solid compound (a yield: 70%). (calculation value: 584.71, measurement value: MS[M+1] 585.01)

EXAMPLE 8

Synthesis of Compound A-8

The compound A-8 was synthesized through the following Reaction Scheme 8.

[Reaction Scheme 8]

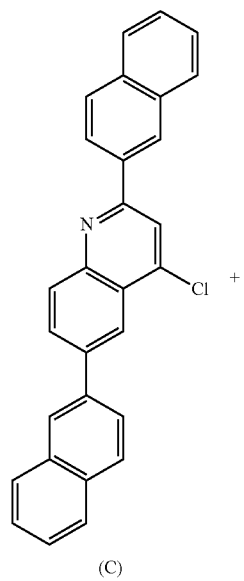

(C)

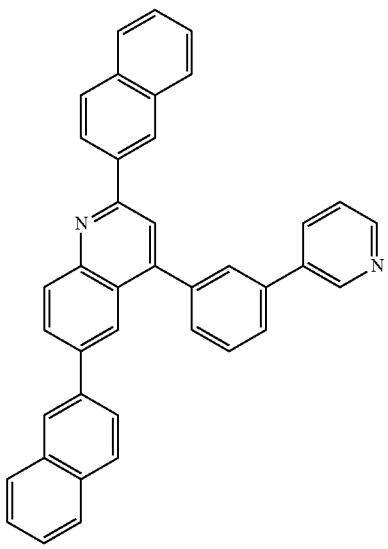

10.0 g (21.5 mmol) of the intermediate product (C), 7.2 g (25.8 mmol) of 3-(4-(4,4,5,5-tetramethyl-1,3,2-dioxaborolan-2-yl)phenyl)pyridine and 0.7 g (0.6 mmol) of tetrakis(triphenylphosphine)palladium [Pd(PPh₃)₄] were dissolved in 200 ml of tetrahydrofuran (THF) as a solvent, a solution obtained by dissolving 11.9 g (85.8 mmol) of potassium carbonate (K₂CO₃) in 100 ml of water was added thereto, and the mixture was reacted at 90° C. for 12 hours. Then, a solvent was removed from the obtained reactant under a reduced pressure, and a product therefrom was washed with water and methanol. The residue was recrystallized with toluene, and a precipitate therefrom was separated through a filter and washed with toluene and then, dried, obtaining 9.5 g of a white solid compound (a yield: 83%). (calculation value: 534.65, measurement value: MS[M+1] 534.95)

EXAMPLE 9

Synthesis of Compound A-281

The compound A-281 was synthesized through 4 steps provided in the following Reaction Scheme 9.

[Reaction Scheme 9]

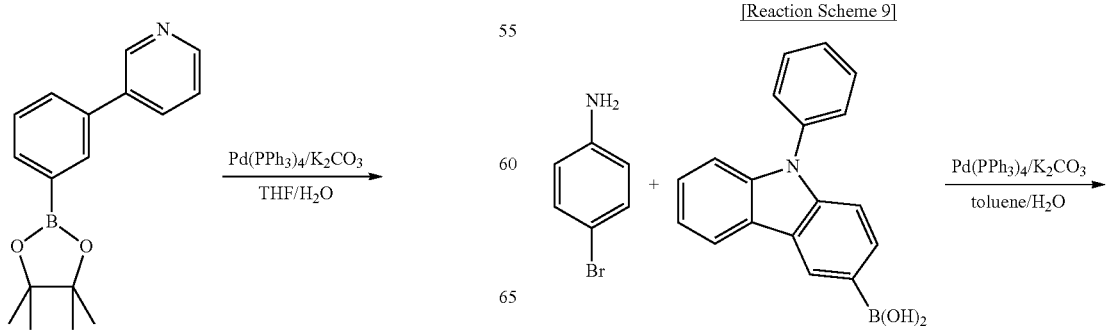

163
-continued
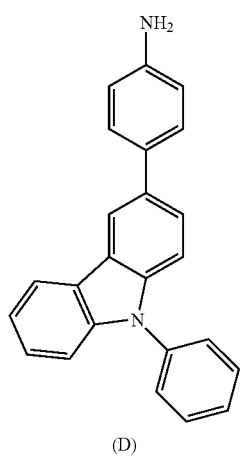
(D)
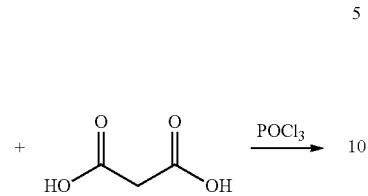
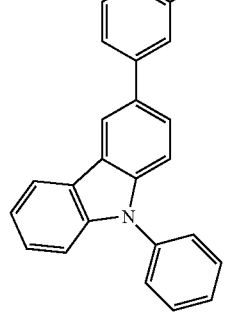
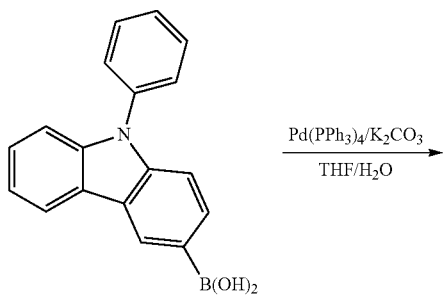
(E)
164
-continued
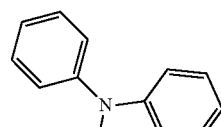
(F)
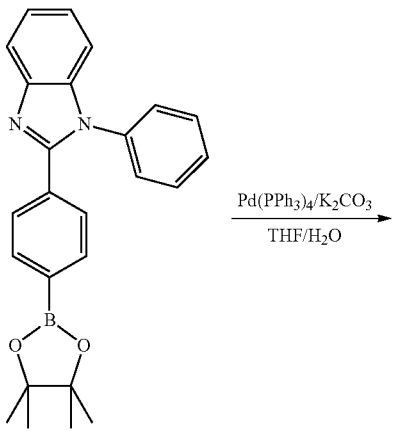

-continued

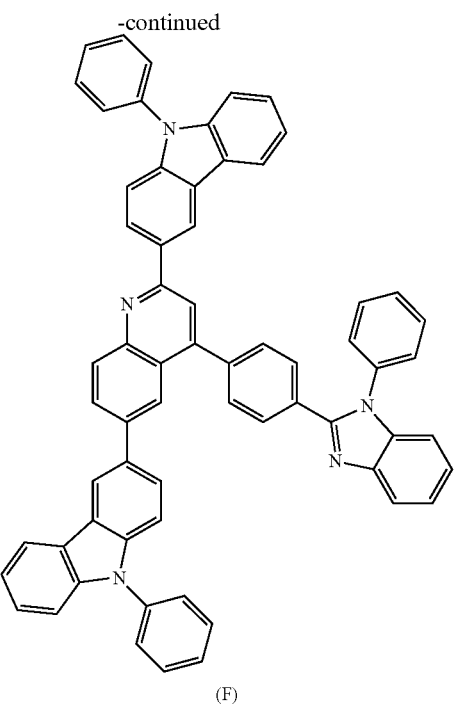

(F)

First Step; Synthesis of Intermediate Product (D)

70.0 g (406.9 mmol) of 4-bromoaniline, 114.5 g (398.8 mmol) of (9-phenyl-9H-carbazol-3-yl)boronic acid and 11.8 g (10.2 mmol) of tetrakis(triphenylphosphine)palladium [Pd(PPh$_3$)$_4$] were dissolved in 1050 ml of toluene as a solvent, a solvent obtained by dissolving 112.5 g (813.9 mmol) of potassium carbonate (K$_2$CO$_3$) in 490 ml of water was added thereto, and the mixture was reacted at 100° C. for 12 hours. Then, an aqueous layer was removed from the reactant, a solvent was removed therefrom under a reduced pressure, and a product therefrom was washed with water and methanol. The obtained solid mixture was separated through column and dried, obtaining 90.0 g of a yellow solid intermediate product (D) (a yield: 66%).

Second Step; Synthesis of Intermediate Product (E)

60.0 g (179.4 mmol) of the intermediate product (D) and 28.0 g (269.1 mmol) of malonic acid were dissolved in 164 ml of phosphorusoxychloride (POCl$_3$) as a solvent, and the solution was reacted at 140° C. for 4 hours. The obtained reactant was poured into ice water, and a solid formed therein was filtered and washed with water and sodium bicarbonate-saturated aqueous solution. The obtained solid mixture was washed with methanol and dried, obtaining 28.0 g of a light yellow solid intermediate product (E) (a yield: 35%).

Third Step: Synthesis of Intermediate Product (F)

20.0 g (45.5 mmol) of the intermediate product (E), 13.1 g (45.5 mmol) of (9-phenyl-9H-carbazol-3-yl)boronic acid and 1.6 g (1.4 mmol) of tetrakis(triphenylphosphine)palladium [Pd(PPh$_3$)$_4$] were dissolved in 400 ml of tetrahydrofuran (THF) as a solvent, a solution obtained by dissolving 12.6 g (91.1 mmol) of potassium carbonate (K$_2$CO$_3$) in 200 ml of water was added thereto, and the mixture was reacted at 70° C. for 12 hours. The resultant was cooled down to room temperature, and a solid mixture formed therein was filtered through a glass filter. The residue was recrystallized with toluene, and a precipitate therefrom was separated through a filter and washed with toluene and then, dried, obtaining 23.0 g of a white solid intermediate product (F) (a yield: 78%).

Fourth Step: Synthesis of Compound A-281

15.0 g (23.2 mmol) of the intermediate product (F), 11.0 g (27.9 mmol) of 1-phenyl-2-(4-(4,4,5,5-tetramethyl-1,3,2-dioxaborolan-2-yl)phenyl)-1H-benzoimidazole and 0.8 g (0.7 mmol) of tetrakis(triphenylphosphine)palladium were dissolved in 300 ml of tetrahydrofuran (THF) as a solvent, a solution obtained by dissolving 12.8 g (92.9 mmol) of potassium carbonate (K$_2$CO$_3$) was dissolved in 150 ml of water was added thereto, and the mixture was reacted at 90° C. for 12 hours. Then, a solvent was removed from the obtained reactant under a reduced pressure, and a product therefrom was washed with water and methanol. The residue was recrystallized with toluene, and a precipitate therefrom was separated through a filter and washed with toluene and then, dried, obtaining 16.0 g of a white solid compound (a yield: 78%). (calculation value: 880.04, measurement value: MS[M+1] 880.34)

(Manufacture of Organic Light Emitting Diode)

EXAMPLE 10

As for an anode, 1000 Å-thick ITO was used, and as for a cathode, 1000 Å-thick aluminum (Al) was used.

Specifically, illustrating a method of manufacturing an organic light emitting diode, the anode is manufactured by cutting an ITO glass substrate having 15 Ω/cm² of sheet resistance into a size of 50 mm×50 mm×0.7 mm, ultrasonic wave-cleaning them in acetone, isopropylalcohol, and pure water for 5 minutes respectively, and UV ozone cleaning them for 30 minutes.

On the glass substrate, a 65 nm-thick hole injection layer (HIL) was formed by depositing N1,N1'-(biphenyl-4,4'-diyl)bis(N1-(naphthalen-2-yl)-N4,N4-diphenylbenzene-1,4-diamine), and then subsequently a 40 nm-thick hole transport layer (HTL) was formed by depositing N,N'-di(1-naphthyl)-N,N'-diphenylbenzidine.

A 25 nm-thick emission layer was formed by depositing 4% of N,N,N',N'-tetrakis (3,4-dimethylphenyl)chrysene-6,12-diamine and 96% of 9-(3-(naphthalen-1-yl)phenyl)-10-(naphthalene-2-yl)anthracene.

Subsequently, a 30 nm-thick electron transport layer (ETL) was formed by depositing the compound prepared in Example 1.

On the electron transport layer (ETL), an Liq/Al electrode was formed by vacuum-depositing Liq in a thickness of 0.5 nm as an electron injection layer (EIL), and then vacuum-depositing Al in a thickness of 100 nm.

EXAMPLE 11

An organic light emitting diode was manufactured according to the same method as Example 10 except for using the compound of Example 3 instead of the compound of Example 1 as an electron transport layer (ETL).

EXAMPLE 12

An organic light emitting diode was manufactured according to the same method as Example 10 except for using the compound of Example 1 and Liq at a 1:1 ratio instead of the compound of Example 1 as an electron transport layer (ETL).

EXAMPLE 13

An organic light emitting diode was manufactured according to the same method as Example 10 except for using the compound of Example 3 and Liq at a 1:1 ratio instead of the compound of Example 1 as an electron transport layer (ETL).

EXAMPLE 14

An organic light emitting diode was manufactured according to the same method as Example 10 except for using the compound of Example 4 and Liq at a 1:1 ratio instead of the compound of Example 1 as an electron transport layer (ETL).

COMPARATIVE EXAMPLE 1

An organic light emitting diode was manufactured according to the same method as Example 10 except for using the compound of Chemical Formula R-1 and Liq at a 1:1 ratio instead of the compound of Example 1 as an electron transport layer (ETL).

[Chemical Formula R-1]

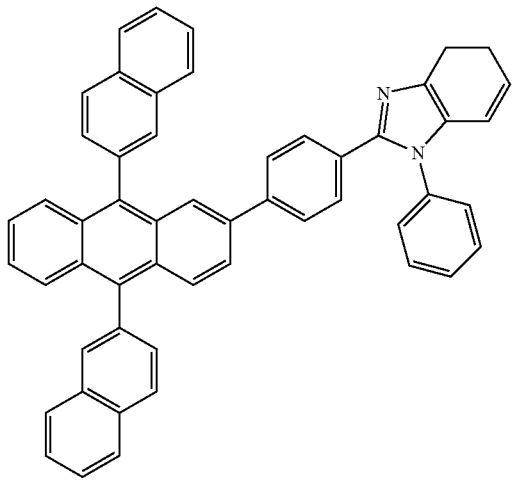

COMPARATIVE EXAMPLE 2

An organic light emitting diode was manufactured according to the same method as Example 13 except for using the compound of Chemical Formula R-1 and Liq at a 1:1 ratio instead of the compound of Example 1 as an electron transport layer (ETL).

(Performance Measurement of Organic Light Emitting Diode)

Current density and luminance changes depending on a voltage and luminous efficiency of each organic light emitting diode according to Examples 10 to 14 and Comparative Examples 1 and 2 were measured. The measurements were specifically performed in the following method, and the results were provided in the following Table 1.

1) Measurement of Current Density Change Depending on Voltage Change

Current values flowing in the unit device of the organic light emitting diodes according to Examples 10 to 14, Comparative Examples 1 and 2 were measured for, while increasing the voltage using a current-voltage meter (Keithley 2400), and the measured current values were divided by an area to provide the results.

2) Measurement of Luminance Change Depending on Voltage Change

Luminance of the organic light emitting diodes according to Examples 10 to 14, Comparative Examples 1 and 2 was measured for luminance, while increasing the voltage using a luminance meter (Minolta Cs-1000A).

3) Measurement of Luminous Efficiency and Power Efficiency

Current efficiency (cd/A) at the same current density (10 mA/cm$^2$) were calculated by using the luminance, current density, and voltages (V) from the items 1) Measurement of Current Density Change Depending on Voltage Change and 2) Measurement of Luminance Change Depending on Voltage Change, and the results are shown in Table 1.

4) Color Coordinate

The color coordinate of each organic light emitting diode according to Examples 10 to 14 and Comparative Examples 1 and 2 was measured at 6000 cd/m$^2$ by using a luminance meter (Keithley 2635B).

TABLE 1

| | Luminance 500 cd/m$^2$ | | | | |
| | Driving voltage | Luminous efficiency | Power efficiency | CIE | |
| | (V) | (cd/A) | (lm/W) | x | y |
| Example 10 | 5.1 | 4.3 | 2.6 | 0.14 | 0.06 |
| Example 11 | 4.4 | 4.6 | 3.3 | 0.14 | 0.05 |
| Comparative Example 1 | 5.1 | 3.7 | 2.3 | 0.14 | 0.05 |
| Example 12 | 3.8 | 6.2 | 5.1 | 0.14 | 0.05 |
| Example 13 | 3.9 | 5.3 | 4.3 | 0.14 | 0.05 |
| Example 14 | 3.8 | 6.0 | 5.0 | 0.15 | 0.06 |
| Comparative Example 2 | 4.2 | 5.4 | 4.1 | 0.14 | 0.05 |

As shown in Table 1, the organic light emitting diodes according to Examples 10 to 14 showed improved characteristics in terms of a driving voltage, luminous efficiency and/or power efficiency compared with the organic light emitting diodes according to Comparative Examples 1 and 2.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectric device, the compound being represented by Chemical Formula 1:

[Chemical Formula 1]

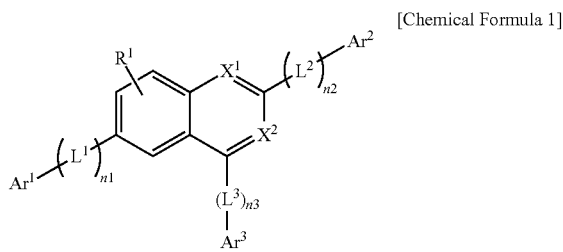

wherein, in Chemical Formula 1, $X^1$ is N, $X^2$ is CR',

Ar$^1$ and Ar$^2$ are each independently a substituted or unsubstituted C6 to C30 aryl group, or a substituted or unsubstituted C2 to C30 heteroaryl group, $L^1$ to $L^3$ are each independently a substituted or unsubstituted C6 to C30 arylene group or a substituted or unsubstituted C2 to C30 heteroarylene group, n1 to n3 are independently 0 or 1, $R^1$ and R' are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group or a substituted or unsubstituted silyl group, and Ar$^3$ is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, or a substituent represented by Chemical Formula 2 or Chemical Formula A,

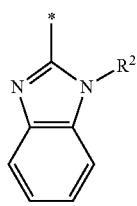

[Chemical Formula 2]

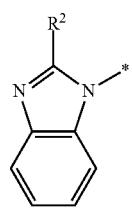

[Chemical Formula A]

wherein, in Chemical Formula 2 and A, $R^2$ is hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group.

2. The compound for an organic optoelectric device of claim 1, wherein the Ar$^1$ and Ar$^2$ are each independently a substituted or unsubstituted C6 to C30 aryl group.

3. The compound for an organic optoelectric device of claim 1, wherein the Ar$^1$ and Ar$^2$ are each independently a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

4. The compound for an organic optoelectric device of claim 1, wherein at least one of the Ar$^1$ and Ar$^2$ is a substituent represented by Chemical Formula 3 or 4 :

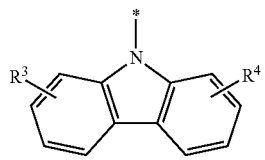

[Chemical Formula 3]

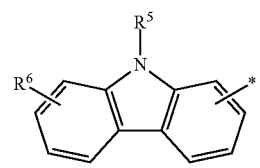

[Chemical Formula 4]

wherein, in Chemical Formula 3 and 4, $R^3$ to $R^6$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group.

5. The compound for an organic optoelectric device of claim 1, wherein n3 is 1 and the $L^3$ is a substituted or unsubstituted C2 to C30 heteroarylene group.

6. The compound for an organic optoelectric device of claim 1, wherein n3 is 1 and the $L^3$ is a substituted or unsubstituted pyridinylene group, a substituted or unsubstituted pyrimidinylene group, or a substituted or unsubstituted triazinylene group.

7. An organic light emitting diode, comprising:
an anode, a cathode, and an organic thin layer between the anode and the cathode,
wherein the organic thin layer includes at least one layer that includes the compound of claim 1.

8. The organic light emitting diode of claim 7, wherein the organic thin layer includes an electron injection layer (EIL), an electron transport layer (ETL), a hole injection layer (HIL), a hole transport layer (HTL), or an emission layer.

9. The organic light emitting diode of claim 7, wherein the organic thin layer is an electron injection layer (EIL) or an electron transport layer (ETL).

10. The organic light emitting diode of claim 7, wherein the organic thin layer is an emission layer.

11. The organic light emitting diode of claim 7, wherein the organic thin layer includes and emission layer and the compound is used as a host in the emission layer.

12. A display device comprising the organic light emitting diode of claim 7.

* * * * *